(12) United States Patent
Zhang et al.

(10) Patent No.: US 10,294,260 B2
(45) Date of Patent: *May 21, 2019

(54) TETRACYCLIC ANTHRAQUINONE DERIVATIVES

(71) Applicant: TIANJIN HEMAY ONCOLOGY PHARMACEUTICAL CO., LTD., Tianjin (CN)

(72) Inventors: Hesheng Zhang, Tianjin (CN); Aihong Huo, Tianjin (CN); Zhenzhong Li, Tianjin (CN)

(73) Assignee: TIANJIN HEMAY ONCOLOGY PHARMACEUTICAL CO., LTD., Tianjin (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/587,884

(22) Filed: May 5, 2017

(65) Prior Publication Data

US 2017/0247403 A1 Aug. 31, 2017

Related U.S. Application Data

(63) Continuation of application No. 14/383,523, filed as application No. PCT/CN2013/000233 on Mar. 6, 2013, now Pat. No. 9,670,242.

(30) Foreign Application Priority Data

Mar. 6, 2012 (CN) .......................... 2012 1 0055298

(51) Int. Cl.
*C07H 1/00* (2006.01)
*C07H 19/044* (2006.01)

(52) U.S. Cl.
CPC ............. *C07H 19/044* (2013.01); *C07H 1/00* (2013.01)

(58) Field of Classification Search
CPC .................................................. C07H 19/044
See application file for complete search history.

(56) References Cited

U.S. PATENT DOCUMENTS

| | | | |
|---|---|---|---|
| 3,590,028 | A | 6/1971 | Arcamone et al. |
| 4,012,448 | A | 3/1977 | Smith et al. |
| 5,304,687 | A | 4/1994 | Bargiotti et al. |
| 8,877,720 | B2 | 11/2014 | Zhang |
| 9,115,165 | B2 | 8/2015 | Zhang |
| 9,670,242 | B2 * | 6/2017 | Zhang .................. C07H 19/044 |
| 2009/0325894 | A1 | 12/2009 | Zhang |
| 2012/0308646 | A1 | 12/2012 | Zhang |

FOREIGN PATENT DOCUMENTS

| | | |
|---|---|---|
| CN | 101555264 A | 10/2009 |
| JP | H06-172312 A | 6/1994 |
| JP | H07-82291 A | 3/1995 |
| JP | H0782291 A | 3/1995 |
| JP | 2011-516507 A | 5/2011 |
| JP | 2011516507 A | 5/2011 |
| JP | 2015509511 A | 3/2015 |
| WO | 2009/099741 A1 | 8/2009 |

OTHER PUBLICATIONS

Engel et al., "Targeted Therapy of Breast and Gynecological Cancers with Cytotoxic Analogues of Peptide Hormones," Molecular Pharmaceuticals, vol. 4, No. 5, pp. 652-658.
European Application No. 13 847 102.4, Office Action dated May 27, 2016.
International Search Report for International Application No. PCT/CN2013/000233 dated Jun. 13, 2013.
Office Action in JP2016-243879, dated Jun. 20, 2017.
Chhikara et al., "Synthesis, Anticancer Activities, and CellularUptake Studies of Lipophilic Derivatives of Doxorubicin Succinate," Journal of Medicinal Chemistry, 2012, 55, 1500-1510.

\* cited by examiner

*Primary Examiner* — Lawrence E Crane
(74) *Attorney, Agent, or Firm* — Kilpatrick Townsend & Stockton LLP

(57) ABSTRACT

Disclosed are a compound represented by formula (I) and a pharmaceutically acceptable salt thereof, Formula (I)

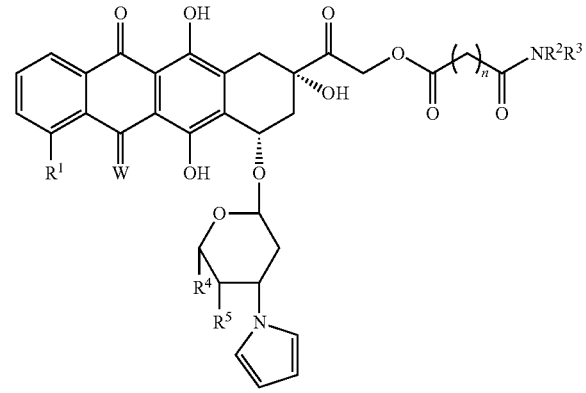

wherein $R^1$, $R^2$, $R^3$, $R^4$, $R^5$, W, n are defined as in the present application. Also disclosed is a method for treating cancer, comprising administering to a subject in need thereof a therapeutically effective amount of the compound represented by formula (I) or a pharmaceutically acceptable salt thereof. The compound and a salt thereof according to the present application possess good anticancer and/or antitumor activity, and good water solubility and stability, as well as good tolerance in animal bodies. Also disclosed is a process for preparing a compound represented by formula (I) of the present application.

10 Claims, 2 Drawing Sheets

TETRACYCLIC ANTHRAQUINONE DERIVATIVES

CROSS REFERENCE TO RELATED APPLICATIONS

This application is a Continuation of U.S. application Ser. No. 14/383,523, filed Sep. 5, 2014, which is a U.S. National Phase Application of PCT/CN2013/000233, filed Mar. 6, 2013, which claims priority to Chinese Application No. 201210055298.7, filed Mar. 6, 2012, the disclosures of which are incorporated herein by reference.

FIELD

The present application relates to the field of organic compounds and medicinal chemistry. In particular, the present application relates to tetracyclic anthraquinone derivatives, preparation processes and applications thereof.

BACKGROUND

Tetracyclic anthraquinone antibiotics, in particular doxorubicin and daunorubicin, are widely used anticancer drugs. Doxorubicin has significant curative effects on lots of solid tumors including liver cancer, gastric cancer, breast cancer, lung cancer, ovary cancer and various leukemias. Daunorubicin is one of the most effective drugs for treating leukemia. However, due to their side effects such as severe myelosuppression, cardiac toxicity, adverse responses in digestive tracts and the like, their clinical applications are somewhat restricted. Up to now, lots of derivatives of tetracyclic anthraquinones have already been separated from the nature or artificially synthesized.

SUMMARY

One aspect of the present application relates to a compound represented by formula (I) and a pharmaceutically acceptable salt thereof,

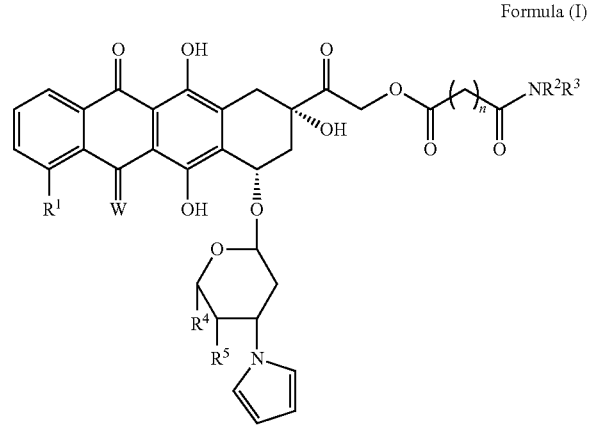

Formula (I)

wherein:
$R^1$ is selected from the group consisting of H, optionally substituted alkyl, and optionally substituted alkoxy;

$R^2$ is selected from the group consisting of H, optionally substituted aryl, optionally substituted heteroaryl, optionally substituted (alkyleneoxy)$_m$alkyl, optionally substituted heterocyclyl, optionally substituted alkyl, and optionally substituted sulfonyl;

$R^3$ is selected from the group consisting of H, optionally substituted aryl, optionally substituted heteroaryl, optionally substituted (alkyleneoxy)$_m$alkyl, optionally substituted heterocyclyl, optionally substituted alkyl, and optionally substituted sulfonyl;

or $NR^2R^3$ represents optionally substituted heterocyclyl;

m is selected from the group consisting of 0, 1, 2, 3, 4, 5, 6, 7, 8, 9, 10, and 11;

W is selected from the group consisting of O and NH;

$R^4$ is selected from the group consisting of H, F, and optionally substituted alkyl;

$R^5$ is selected from the group consisting of H, F, optionally substituted alkyl and $OR^6$, wherein $R^6$ is selected from the group consisting of H and tetrahydropyran-2-yl;

n is selected from the group consisting of 1, 2 and 3.

Another aspect of the present application relates to a compound represented by formula (I) and a pharmaceutically acceptable salt thereof,

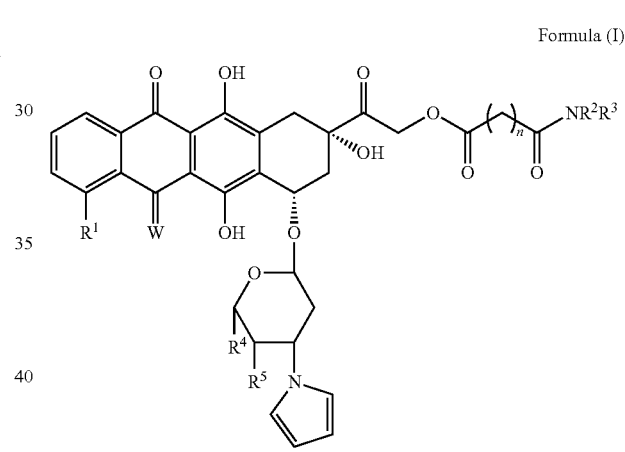

Formula (I)

wherein:
$R^1$ is selected from the group consisting of H, $C_{1-4}$alkyl, and $C_{1-4}$alkoxy;

$R^2$ is selected from the group consisting of H, aryl, heteroaryl, $(C_{1-4}alkyleneoxy)_mC_{1-4}$alkyl, heterocyclyl, $C_{1-4}$alkyl, and sulfonyl;

$R^3$ is selected from the group consisting of H, aryl, heteroaryl, $(C_{1-4}alkyleneoxy)_mC_{1-4}$alkyl, heterocyclyl, $C_{1-4}$alkyl, and sulfonyl;

or $NR^2R^3$ represents heterocyclyl;

m is selected from the group consisting of 0, 1, 2, 3, 4, 5, 6, 7, 8, 9, 10, and 11;

W is selected from the group consisting of O and NH;

$R^4$ is selected from the group consisting of H, F and $C_{1-4}$alkyl;

$R^5$ is selected from the group consisting of H, F, $C_{1-4}$alkyl and $OR^6$, wherein $R^6$ is selected from the group consisting of H and tetrahydropyran-2-yl; and n is selected from the group consisting of 1, 2 and 3.

Yet another aspect of the present application relates to a compound selected from the group consisting of:

| 3 | 4 -continued |
|---|---|
| 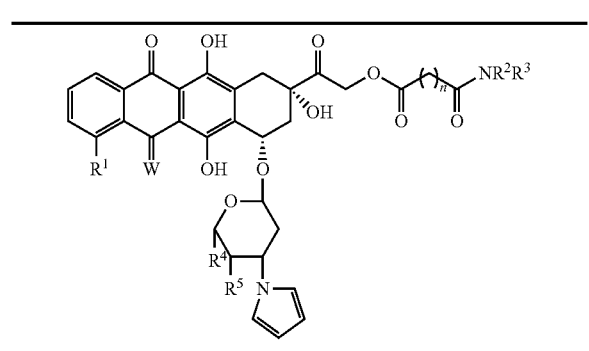 | 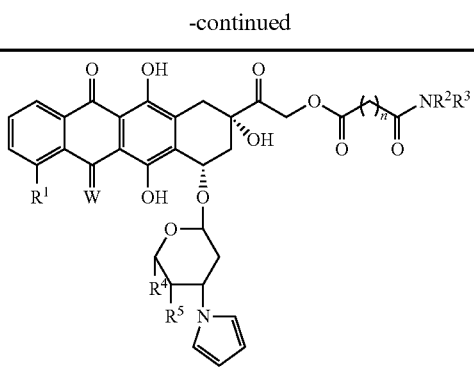 |
| No. n  NR²R³ | No. n  NR²R³ |
| 1  3  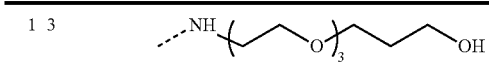 | 12  2  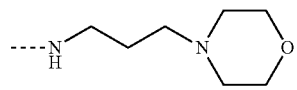 |
| 2  2  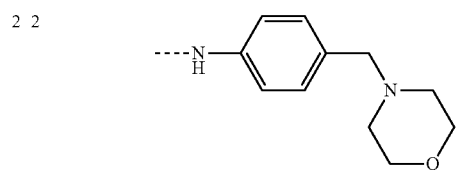 | 13  3  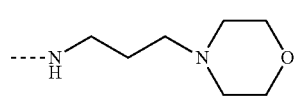 |
| 3  3  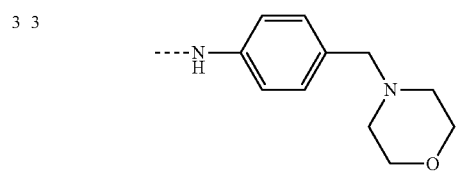 | 14  2  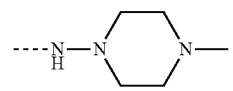 |
| 4  2  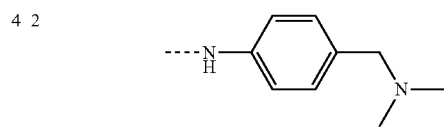 | 15  3  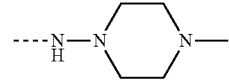 |
| 5  3  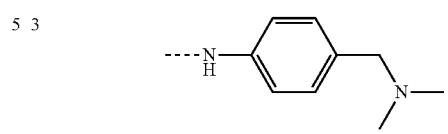 | 16  2  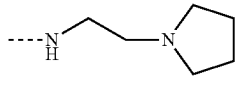 |
| 6  2  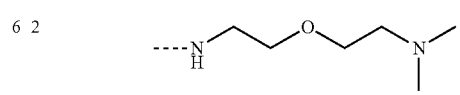 | 17  3  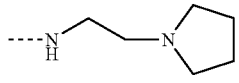 |
| 7  3  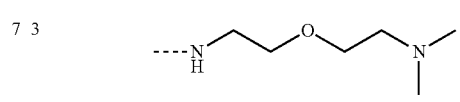 | 18  2  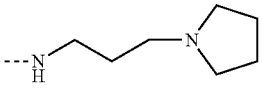 |
| 8  2  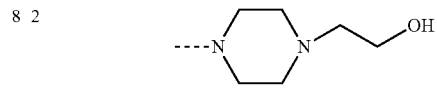 | 19  3  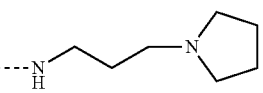 |
| 9  3  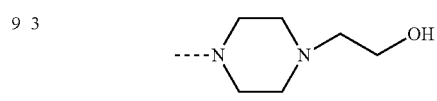 | 20  2  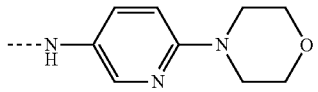 |
| 10  2   | 21  3  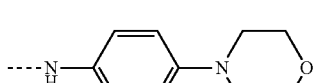 |
| 11  3   | 22  2  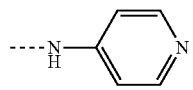 |
|  | 23  3  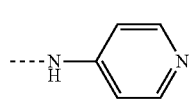 |

-continued

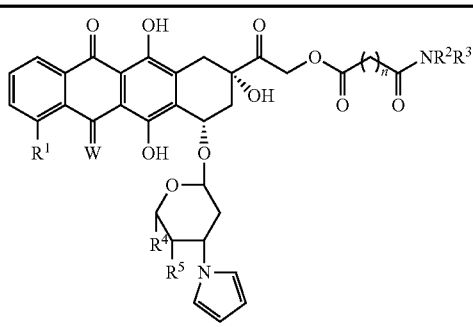

| No. | n | NR²R³ |
|---|---|---|
| 24 | 2 | ----NH-(3-pyridyl) |
| 25 | 3 | ----NH-(3-pyridyl) |
| 26 | 2 | ----NH-CH₂-(4-pyridyl) |
| 27 | 3 | ----NH-CH₂-(4-pyridyl) |
| 28 | 2 | ----NH-CH₂-(3-pyridyl) |
| 29 | 3 | ----NH-CH₂-(3-pyridyl) |
| 30 | 2 | ----HN-CH₂-(2-pyridyl) |
| 31 | 3 | ----HN-CH₂-(2-pyridyl) |
| 32 | 2 | ----NH-CH₂CH₂-(4-pyridyl) |
| 33 | 3 | ----NH-CH₂CH₂-(4-pyridyl) |
| 34 | 2 | ----NH-CH₂CH₂-(2-pyridyl) |

-continued

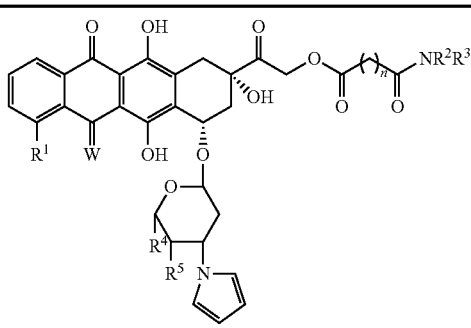

| No. | n | NR²R³ |
|---|---|---|
| 35 | 3 | ----NH-CH₂CH₂-(2-pyridyl) |
| 36 | 2 | ----NH-CH₂CH₂-(3-pyridyl) |
| 37 | 3 | ----NH-CH₂CH₂-(3-pyridyl) |
| 38 | 2 | ----NH-CH₂CH₂-C₆H₄-SO₂NH₂ |
| 39 | 3 | ----NH-CH₂CH₂-C₆H₄-SO₂NH₂ |
| 40 | 2 | ----N(piperazinyl)-ethyl |
| 41 | 3 | ----N(piperazinyl)-ethyl |
| 42 | 2 | ----NH-(6-purinyl) |
| 43 | 3 | ----NH-(6-purinyl) |
| 44 | 2 | ----N(piperazinyl)-CH₂CH₂CH₂-N(CH₃)₂ |

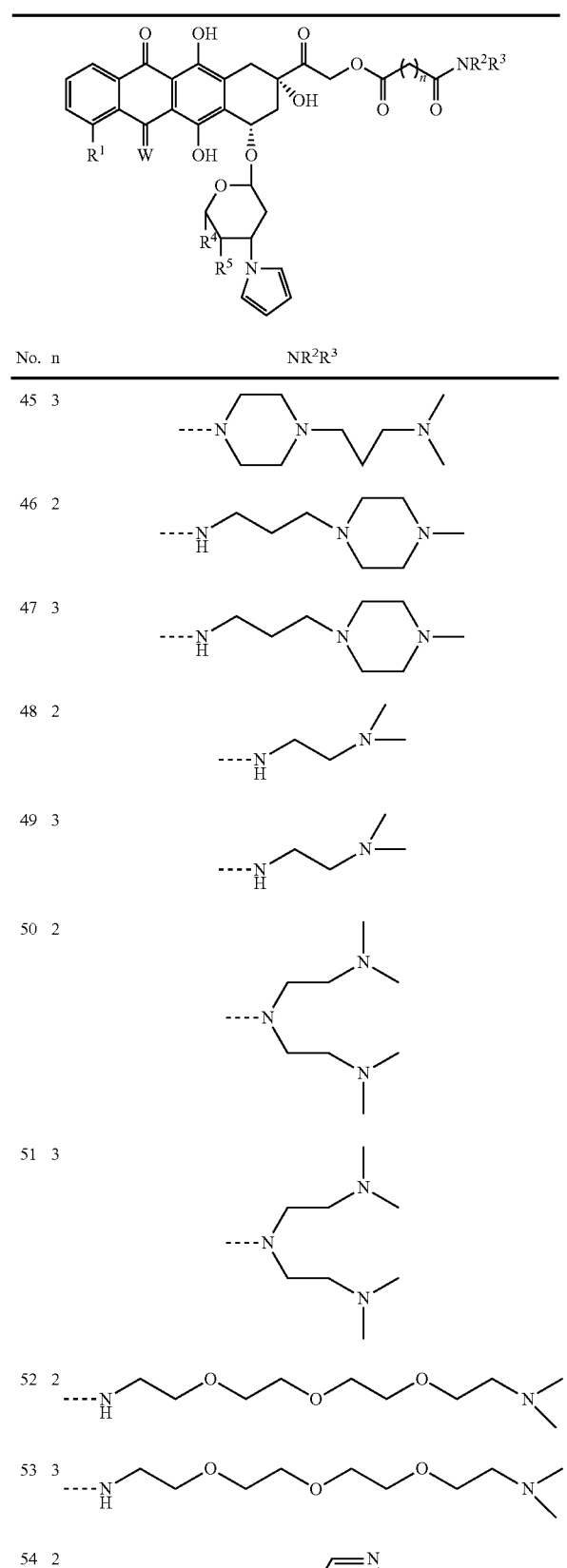
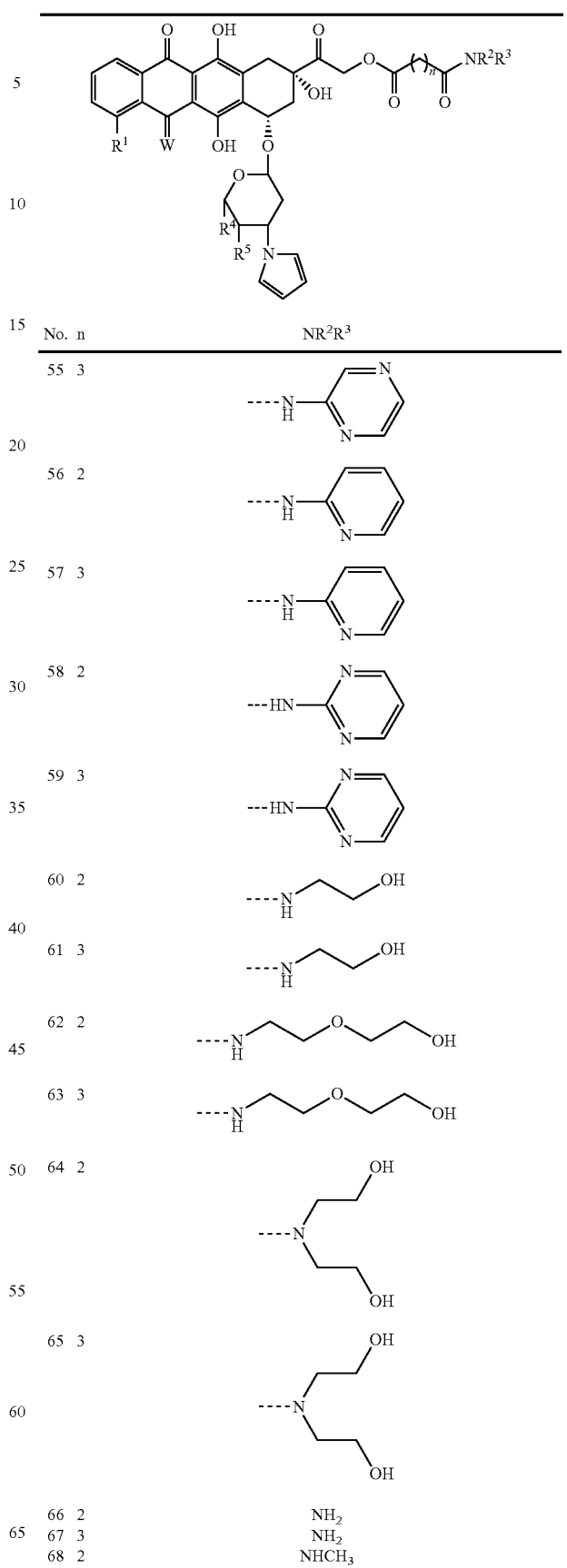

-continued

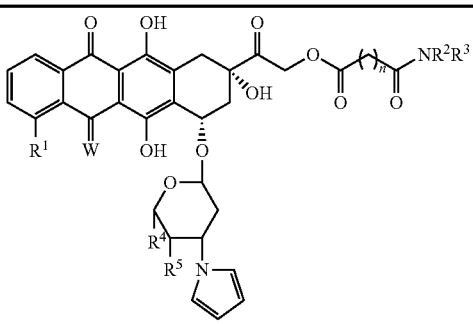

| No. | n | NR²R³ |
|---|---|---|
| 69 | 3 | NHCH₃ |
| 70 | 2 | N(CH₃)₂ |
| 71 | 3 | N(CH₃)₂ |
| 72 | 2 | ----N(morpholine) |
| 73 | 3 | ----N(morpholine) |
| 74 | 2 | ----N(piperidine) |
| 75 | 2 | ----N(pyrrolidine) |
| 88 | 2 | ----NH-CH₂CH₂-N(morpholine) |
| 90 | 2 | ----NH-(CH₂CH₂O)₇-OH |
| 91 | 2 | ----NH-(CH₂CH₂O)₈-OH |
| 92 | 2 | ----NH-(CH₂CH₂O)₁₁-OH |
| 93 | 2 | ----NH-(CH₂CH₂O)₈-OCH₃ |
| 94 | 2 | ----NH-SO₂-CH₃ |
| 95 | 2 | ----NH-SO₂-phenyl |

77) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((4-(2-hydroxy)ethyl)piperazin-1-yl)-4-oxo-butyrato)-1-methoxy-5,12-naphthalenedione acetate;

78) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((3-(morpholin-1-yl)propyl)amino)-4-oxo-butyrato)-1-methoxy-5,12-naphthalenedione acetate;

79) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((4-methyl)piperazin-1-yl)amino)-4-oxo-butyrato)-1-methoxy-5,12-naphthalenedione acetate;

80) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(4-ethylpiperazin-1-yl)-4-oxo-butyrato)-1-methoxy-5,12-naphthalenedione acetate;

81) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((3-(4-methylpiperazin-1-yl)propyl)amino)-4-oxo-butyrato)-1-methoxy-5,12-naphthalenedione acetate;

82) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((pyridin-4-yl)methyl)amino)-4-oxo-butyrato)-1-methoxy-5,12-naphthalenedione acetate;

83) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((pyridin-3-yl)methyl)amino)-4-oxo-butyrato)-1-methoxy-5,12-naphthalenedione acetate;

84) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-2-yl)ethyl)amino)-4-oxo-butyrato)-1-methoxy-5,12-naphthalenedione acetate;

85) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-3-yl)ethyl)amino)-4-oxo-butyrato)-1-methoxy-5,12-naphthalenedione acetate;

86) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-4-yl)ethyl)amino)-4-oxo-butyrato)-1-methoxy-5,12-naphthalenedione acetate;

87) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(4-(3-(dimethylamino)propyl)piperazin-1-yl)-4-oxo-butyrato)-1-methoxy-5,12-naphthalenedione acetate;

89) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione acetate;

96) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione phosphate; and 99) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione hydrochloride.

Still another aspect of the present application relates to a process for preparing a compound represented by formula (I), comprising:

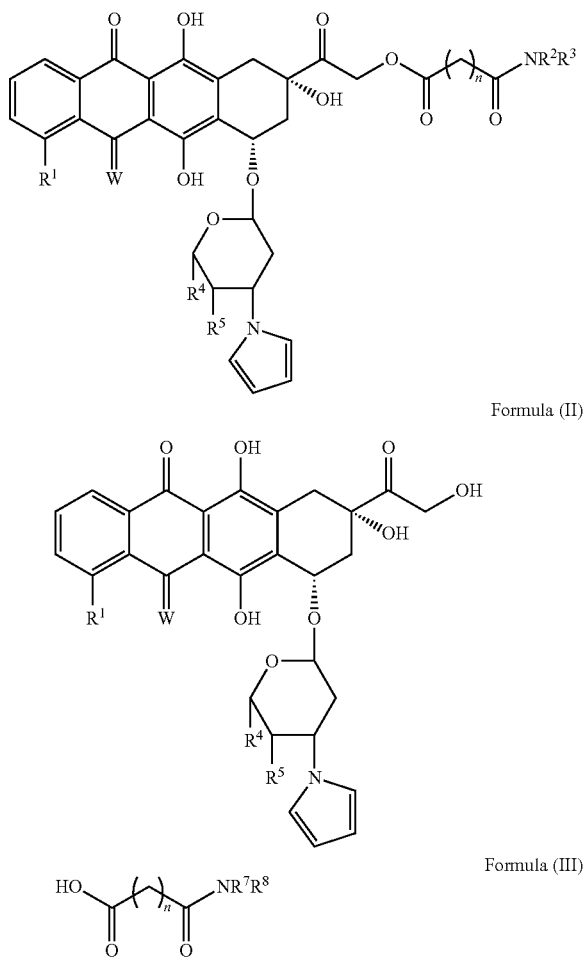

Formula (I)

Formula (II)

Formula (III)

reacting a compound represented by formula (II) with a compound represented by formula (III) in the presence of a condensation agent to obtain the compound represented by formula (I), wherein:

in the compound represented by formula (I), $R^1$ is selected from the group consisting of H, $C_{1-4}$alkyl, and $C_{1-4}$alkoxy; $R^2$ is selected from the group consisting of H, aryl, heteroaryl, $(C_{1-4}\text{alkyleneoxy})_m C_{1-4}$alkyl, heterocyclyl, $C_{1-4}$alkyl, and sulfonyl; $R^3$ is selected from the group consisting of H, aryl, heteroaryl, $(C_{1-4}\text{alkyleneoxy})_m C_{1-4}$alkyl, heterocyclyl, $C_{1-4}$alkyl, and sulfonyl; or $NR^2R^3$ represents heterocyclyl; m is selected from the group consisting of 0, 1, 2, 3, 4, 5, 6, 7, 8, 9, 10, and 11; W is selected from the group consisting of O and NH; $R^4$ is selected from the group consisting of H, F and $C_{1-4}$alkyl; $R^5$ is selected from the group consisting of H, F, $C_{1-4}$alkyl and $OR^6$, wherein $R^6$ is selected from the group consisting of H and tetrahydropyran-2-yl; and n is selected from the group consisting of 1, 2 and 3;

groups represented by $R^1$, W, $R^4$, $R^5$ in the compound represented by formula (II) are the same as groups represented by $R^1$, W, $R^4$, $R^5$ in the compound represented by formula (I);

n in the compound represented by formula (III) has the same meanings as n in the compound represented by formula (I); groups represented by $R^7$ and $R^8$ in the compound represented by formula (III) are the same as groups represented by $R^2$ and $R^3$ in the compound represented by formula (I), provided that groups represented by $R^7$ and $R^8$ do not comprise NH or $NH_2$; when groups represented by $R^7$ and $R^8$ comprise NH or $NH_2$, the compound represented by formula (III) has an amino-protecting group at N-terminus, and is subject to a deprotection reaction to obtain the compound represented by formula (I).

Yet another aspect of the present application relates to a pharmaceutical composition comprising a compound represented by formula (I) or a pharmaceutically acceptable salt thereof, and a pharmaceutically acceptable carrier.

Still another aspect of the present application relates to a formulation comprising a compound represented by formula (I) or a pharmaceutically acceptable salt thereof, and a pharmaceutically acceptable carrier.

Yet another aspect of the present application relates to a method for treating and/or preventing tumor and/or cancer, comprising administering to a subject in need thereof a therapeutically effective amount of a compound represented by formula (I) or a pharmaceutically acceptable salt thereof, or administering a therapeutically effective amount of a pharmaceutical composition comprising a compound represented by formula (I) or a pharmaceutically acceptable salt and a pharmaceutically acceptable carrier, or administering a therapeutically effective amount of a formulation comprising a compound represented by formula (I) or a pharmaceutically acceptable salt and a pharmaceutically acceptable carrier.

The compound and a salt thereof according to the present application possess good anticancer and/or antitumor activities, and good water solubility and stability, as well as good tolerance in animal bodies. Therefore, they are prone to being developed as clinical drugs.

DETAILED DESCRIPTION

Figure 1:
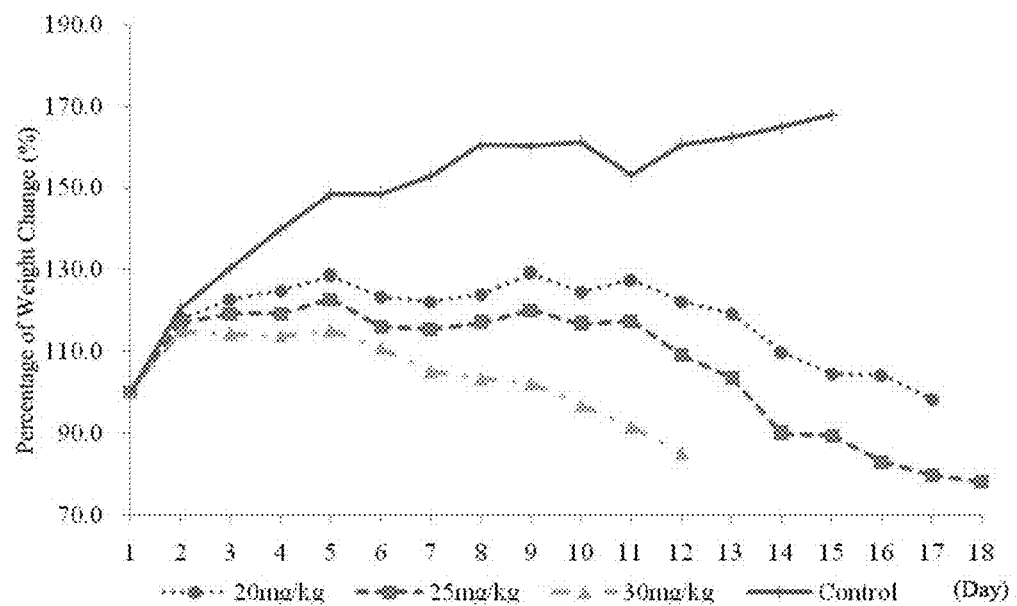
FIG. 1 shows effects of 3'-pyrrolyldoxorubicin on the body weight of experimental animals.

In the following description, certain specific details are included to provide a thorough understanding of various disclosed embodiments. One of ordinary skill in the relevant art, however, will recognize that the embodiments may be practiced without one or more of these specific details, or with other methods, components, materials etc.

Unless the context required otherwise, throughout the specification and claims which follows, the term "comprise" and variations thereof, such as "comprises" and "comprising" are to be construed in an open, inclusive sense, which is as "include, but not limited to".

Reference throughout this specification to "one embodiment", or "an embodiment", or "in another embodiment", or "in some embodiments" means that a particular referent feature, structure or characteristics described in connection with the embodiment is included in at least one embodiment. Therefore, the appearance of the phrases "in one embodiment" or "in the embodiment" or "in another embodiment" or "in some embodiments" in various places throughout this specification are not necessarily all referring to the same embodiment. Moreover, the particular features, structures or characteristics may be combined in any suitable manner in one or more embodiments.

It should be noted that, as used in this specification and the appended claims, the singular forms "a", "an" and "the" include plural referents unless the context clearly stated otherwise. Therefore, for example, a reaction comprising "a catalyst" comprises one catalyst, two or more catalysts. It should be also noted that the use of "or" means "and/or" unless stated otherwise.

DEFINITIONS

Certain chemical groups named herein are preceded by a shorthand notation indicating the total number of carbon atoms that are to be found in the indicated chemical group. For example, $C_7$-$C_{12}$alkyl describes an alkyl group, as defined below, having a total of 7 to 12 carbon atoms, and $C_4$-$C_{12}$ cyclohydrocarbylalkyl describes a cyclohydrocarbylalkyl group, as defined below, having a total of 4 to 12 carbon atoms. The total number of carbon atoms in the shorthand notation does not include the carbons that may exist in the substituents of the groups described.

Accordingly, as used in the specification and appended claims, unless specified to the contrary, the following terms have the meanings indicated:

The term "alkyl", as used herein, refers to a straight or branched hydrocarbon chain group consisting solely of carbon and hydrogen, containing no unsaturated bond, having from one to twelve carbon atoms, preferably one to eight or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (tert-butyl), 3-methylhexyl, 2-methylhexyl, and the like.

Alkyl group may have one to twelve carbon atoms (whenever it appears in the present application, a numerical range such as "one to twelve" refers to each integer in the given number range; e.g. "one to twelve carbon atoms" means that the alkyl group may consist of one carbon atom, two carbon atoms, three carbon atoms, etc., up to and including twelve carbon atoms, although the present definition also covers the occurrence of term "alkyl" where no numerical range is designated). Alkyl group may also be a medium sized alkyl having one to ten carbon atoms. Alkyl group may also be a lower alkyl having one to five carbon atoms. Alkyl group of compounds of the present application may be designated as "$C_{1-4}$ alkyl" or similar designations. By way of example only, "$C_{1-4}$ alkyl" indicates that there are one to four carbon atoms in the alkyl chain, i.e. the alkyl chain is selected from the group consisting of methyl, ethyl, propyl, isopropyl, n-butyl, iso-butyl, sec-butyl, or t-butyl.

Alkyl group may be optionally substituted, i.e. substituted or unsubstituted. When substituted, the substituted group(s) is(are) individually and independently selected from the group consisting of cyclohydrocarbyl, aryl, heteroaryl, heteroalicyclyl, hydroxy, alkoxy, aryloxy, mercapto, allkylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof. Typical hydrocarbyl groups include, but are not limited to, methyl, ethyl, propyl, isopropyl, butyl, isobutyl, t-butyl, pentyl, hexyl, ethenyl, propenyl, buenyl, cyclopropyl, cyclobutyl, cyclopentyl, cyclohexyl, and the like. Whenever a substituent is described as being "optionally substituted", that substituent may be substituted with one of the above substituents.

"$C_{1-4}$ alkyl" refers to an alkyl group as defined above containing one to four carbon atoms. $C_{1-4}$ alkyl group may be optionally substituted as defined for alkyl group.

"$C_{1-6}$ alkyl" refers to an alkyl group as defined above containing one to six carbon atoms. $C_{1-6}$ alkyl group may be optionally substituted as defined for alkyl group.

"$C_{1-12}$ alkyl" refers to an alkyl group as defined above containing one to twelve carbon atoms. $C_{1-12}$ alkyl group may be optionally substituted as defined for alkyl group.

"$C_{2-6}$ alkyl" refers to an alkyl group as defined above containing two to six carbon atoms. $C_{2-6}$ alkyl group may be optionally substituted as defined for alkyl group.

"$C_{3-6}$ alkyl" refers to an alkyl as defined above containing three to six carbon atoms. $C_{3-6}$ alkyl group may be optionally substituted as defined for alkyl group.

"$C_{3-12}$ alkyl" refers to an alkyl as defined above containing three to twelve carbon atoms. $C_{3-12}$ alkyl group may be optionally substituted as defined for alkyl group.

"$C_{6-12}$ alkyl" refers to an alkyl as defined above containing six to twelve carbon atoms. $C_{6-12}$ alkyl group may be optionally substituted as defined for alkyl group.

"$C_{7-12}$ alkyl" refers to an alkyl as defined above containing seven to twelve carbon atoms. $C_{7-12}$ alkyl group may be optionally substituted as defined for alkyl group.

In some embodiments, the alkyl group is $C_{1-12}$ alkyl.
In some embodiments, the alkyl group is $C_{1-8}$ alkyl.
In some embodiments, the alkyl group is $C_{1-6}$ alkyl.
In some embodiments, the alkyl group is $C_{1-4}$ alkyl.

"Alkoxy", as used herein, refers to the formula —OR, wherein R is an alkyl group defined as above, e.g. methoxy, ethoxy, n-propoxy, 1-methyl ethoxy (isopropoxy), n-butoxy, isobutoxy, sec-butoxy, t-butoxy, amoxy, t-amoxy, and the like.

In some embodiments, the alkoxy group is $C_{1-12}$ alkoxy.
In some embodiments, the alkoxy group is $C_{1-8}$ alkoxy.
In some embodiments, the alkoxy group is $C_{1-6}$ alkoxy.
In some embodiments, the alkoxy group is $C_{1-4}$ alkoxy.

"Alkylene", as used herein, refers to a straight or branched divalent hydrocarbon chain group consisting solely of carbon and hydrogen and having from one to eight carbon atoms, which is linked with the other moiety of the molecule and a residual group, e.g. methylene, ethylene, propylene, n-butylene. Alkylene chain can be linked with the other moiety of the molecule and the residual group via one carbon atom in the chain or any two carbon atoms in the chain.

In some embodiments, the alkylene group is $C_{1-12}$ alkylene.
In some embodiments, the alkylene group is $C_{1-8}$ alkylene.
In some embodiments, the alkylene group is $C_{1-6}$ alkylene.
In some embodiments, the alkylene group is $C_{1-4}$ alkylene.

"Alkyleneoxy", as used herein, refers to the formula —OR, wherein R is an alkylene group defined as above, e.g. methyleneoxy, ethyleneoxy, n-propyleneoxy, isopropyleneoxy, n-butyleneoxy, isobutyleneoxy, sec-butyleneoxy, t-butyleneoxy, amyleneoxy, t-amyleneoxy, and the like.

In some embodiments, the alkyleneoxy group is $O(C_{1-12})$ alkylene.
In some embodiments, the alkyleneoxy group is $O(C_{1-8})$ alkylene.

In some embodiments, the alkyleneoxy group is O($C_{1-6}$) alkylene.

In some embodiments, the alkyleneoxy group is O($C_{1-4}$) alkylene.

"Aryl", as used herein, refers to a carbocycle (full carbon) or two or more fused rings (rings sharing with two adjacent carbon atoms), having completely delocalized π electron system. Examples of aryl group include, but are not limited to, fluorenyl, phenyl and naphthyl. The aryl group may have, for example, five to twelve carbon atoms. The aryl group of the present application may be substituted or unsubstituted. Where substituted, hydrogen atom(s) is(are) substituted with one or more substituents independently selected from the group consisting of alkyl, cyclohydrocarbyl, aryl, heteroaryl, heteroalicyclyl, hydroxy, protected hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, protected C-carboxyl, O-carboxyl, isocyanato, thiocyano, isothiocyanato, nitro, silyl, trihalomethanesulfonyl, —NR'R" (R' and R" are alkyl groups defined herein) and protected amino.

In some embodiments, the aryl group is $C_6$-$C_{18}$ aryl.
In some embodiments, the aryl group is $C_6$-$C_{12}$ aryl.
In some embodiments, the aryl group is $C_6$-$C_{10}$ aryl.

"Heteroaryl (aromatic heterocyclyl)" refers to a five- to eighteen-membered aromatic ring group, containing one to seventeen carbon atoms and one to ten heteroatoms selected from the group consisting of nitrogen, oxygen and sulphur. For the purpose of the present invention, the heteroaryl may be monocyclic, bicyclic, tricyclic or tetracyclic ring system, which may comprise fused or bridged ring system. Moreover, nitrogen, carbon or sulphur atom in the heteroaryl group may be optionally oxidized, and the nitrogen atom may be optionally quaternized. The examples include, but are not limited to, azepinyl, acridinyl, benzimidazolyl, benzothiazolyl, benzoindolyl, benzodioxolanyl, benzofuranyl, benzoxazolyl, benzothiazolyl, benzothiadiazolyl, benzo[b][1,4]dioxepanyl, 1,4-benzodioxanyl, benzonaphthofuranyl, benzodioxolanyl, benzodioxadienyl, benzopyranyl, benzopyronyl, benzofuranyl, benzofuranonyl, benzothienyl, benzotriazolyl, benzo[4,6]imidazo[1,2-a]pyridyl, carbazolyl, cinnolinyl, dibenzofuranyl, dibenzothienyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, 2,3-naphthyridinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolyl, quinuclidinyl, isoquinolyl, tetrahydroquinolyl, thiazolyl, thiadiazolyl, triazolyl, tetrazolyl, triazinyl and thiophenyl. Unless stated otherwise specifically in the specification, the term "heteroaryl" is meant to include the heteroaryl groups which may be optionally substituted with one or more substituents independently selected from the group consisting of alkyl, cyclohydrocarbyl, aryl, heteroaryl, heteroalicyclyl, hydroxy, protected hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, protected C-carboxyl, O-carboxyl, isocyanato, thiocyano, isothiocyanato, nitro, silyl, trihalomethanesulfonyl, —NR'R" (R' and R" are alkyl groups defined herein) and protected amino.

In some embodiments, the heteroaryl group is $C_{5-18}$ heteroaryl.

In some embodiments, the heteroaryl group is $C_{5-12}$ heteroaryl.

In some embodiments, the heteroaryl group is $C_{5-18}$ heteroaryl.

The term "heterocyclyl", as used herein, refers to a stable three- to twelve-membered non-aromatic ring group which consists of carbon atoms and from one to five heteroatoms selected from the group consisting of nitrogen, oxygen and sulphur. Examples of such heterocyclyl groups include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxothiomorpholinyl and 1,1-dioxo-thiomorpholinyl. Unless stated otherwise specifically in the specification, the term "heterocyclyl" is meant to include the heterocyclyl groups as defined above, which may be optionally substituted with one or more substituents selected from the group consisting of cyclohydrocarbyl, aryl, heteroaryl, heteroalicyclyl, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, O-carboxyl, isocyanato, thiocyanato, isothiocyanato, nitro, silyl, trihalomethanesulfonyl, —NR'R" (R' and R" are alkyl groups as defined in the present application) or amino including mono- and di-substituted amino group, and the protected derivatives thereof.

In some embodiments, the heterocyclyl group is $C_{3-18}$ heterocyclyl.

In some embodiments, the heterocyclyl group is $C_{3-12}$ heterocyclyl.

In some embodiments, the heterocyclyl group is $C_{3-10}$ heterocyclyl.

"Sulfonyl" refers to —S(=O)$_2$R group, in which R may be alkyl, cyclohydrocarbyl, heterocyclyl, aryl, heteroaryl, etc, as defined above. The examples of sulfonyl groups include, but are not limited to, —S(=O)$_2$CH$_3$ (mesyl), —S(=O)$_2$CF$_3$, —S(=O)$_2$CH$_2$CH$_3$ and 4-methylbenzenesulfonyl (tosyl).

"Optional" or "optionally" means that the subsequently described circumstances may or may not occur, and that the specification includes instances where said event or circumstance occurs and instances in which it does not. For example, "optionally substituted aryl" means that the aryl group may or may not be substituted and that the specification includes the substituted aryl group and the aryl group which is not substituted.

"Pharmaceutically acceptable carriers" include without limitation to any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which have been approved by the United States Food and Drug Administration as being acceptable for use in humans or animals and have no side effects for constituting a pharmaceutical composition.

"Pharmaceutically acceptable salts" include both "pharmaceutically acceptable acid addition salts" and "pharmaceutically acceptable base addition salts".

"Pharmaceutically acceptable acid addition salt" refers to those salts which retain the biological effectiveness and properties of free bases, which are biologically or otherwise desirable, and which are formed with inorganic acids such as, but not limited to hydrochloric acid, hydrobromic acid, sulfuric acid, nitric acid, phosphoric acid and the like; and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are biologically or otherwise desirable. These salts are prepared from addition of an inorganic base or an organic base into the free acid. Salts derived from inorganic bases include, but are not limited to, sodium, potassium, lithium, ammonium, calcium, magnesium, iron, zinc, copper, manganese, aluminum slats, and the like. Preferred inorganic salts are the ammonium, sodium, potassium, calcium, and magnesium salts. Salts derived from organic bases include, but are not limited to, slats of primary, secondary and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminethanol, dicyclohexylamine, lysine, arginine, histidine, caffeine, procaine, hydrabamine, choline, betaine, benzylamine, phenylethylenediamine, ethylenediamine, glucosamine, methylglucosamine, theobromine, triethanolamine, trometamol, purine, piperazine, piperidine, N-ethyl piperidine, polyamine resin and the like. Particularly preferred organic bases are isopropylamine, diethylamine, ethanolamine, trimethylamine, dicyclohexylamine, choline and caffeine.

"Pharmaceutical composition" refers to a formulation formed with a compound of the invention and a medium generally acceptable in the art for the delivery of the biologically active compound to a mammal e.g. humans. Such a medium includes all pharmaceutically acceptable carriers, diluents or excipients.

"Therapeutically effective amount" refers to an amount of a compound of the invention which, when administered to a mammal, preferably a human, is sufficient to effect treatment (as defined below) of the tumor and/or cancer in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment", as used herein, covers the treatment of relevant disease or condition in a mammal, preferably a human, having the relevant disease or disorder, and includes:

(i) preventing the disease or condition from occurring in a mammal, in particular, when such mammal is predisposed to the condition but has not yet been diagnosed as having it;

(ii) inhibiting the disease or condition, i.e. arresting its development; or (iii) relieving the disease or condition, i.e. causing regression of the disease or condition.

Throughout the treatment course, the administration in vivo can be carried out by means of a single administration, a continuous administration or an intermittent administration (such as the administration is carried out by divided dose at appropriate intervals). The method for determining the most effective administration mode and dose would have been well-known for one of ordinary skill in the art, and vary depending on the formulation to be used in the treatment, the object of the treatment, the targeted cell to be treated and the subject to be treated. A single or a multiple administration can be carried out, and the level of dose and the mode can be selected by an attending doctor.

SPECIFIC EMBODIMENTS

In one aspect, the present application relates to a compound represented by formula (I) and a pharmaceutically acceptable salt thereof,

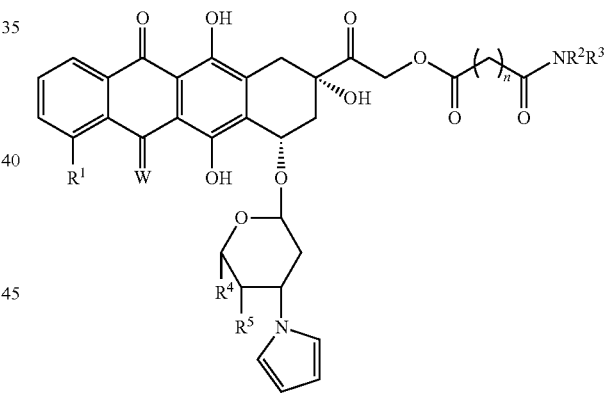

Formula (I)

wherein:

$R^1$ is selected from the group consisting of H, optionally substituted alkyl, and optionally substituted alkoxy;

$R^2$ is selected from the group consisting of H, optionally substituted aryl, optionally substituted heteroaryl, optionally substituted (alkyleneoxy)$_m$alkyl, optionally substituted heterocyclyl, optionally substituted alkyl, and optionally substituted sulfonyl;

$R^3$ is selected from the group consisting of H, optionally substituted aryl, optionally substituted heteroaryl, optionally substituted (alkyleneoxy)$_m$alkyl, optionally substituted heterocyclyl, optionally substituted alkyl, and optionally substituted sulfonyl;

or $NR^2R^3$ represents optionally substituted heterocyclyl;

m is selected from the group consisting of 0, 1, 2, 3, 4, 5, 6, 7, 8, 9, 10, and 11;

W is selected from the group consisting of O and NH;

19

R$^4$ is selected from the group consisting of H, F, and optionally substituted alkyl;

R$^5$ is selected from the group consisting of H, F, optionally substituted alkyl and OR$^6$, wherein R$^6$ is selected from the group consisting of H and tetrahydropyran-2-yl; and n is selected from the group consisting of 1, 2 and 3.

In another aspect, the present application relates to a compound represented by formula (I) and a pharmaceutically acceptable salt thereof,

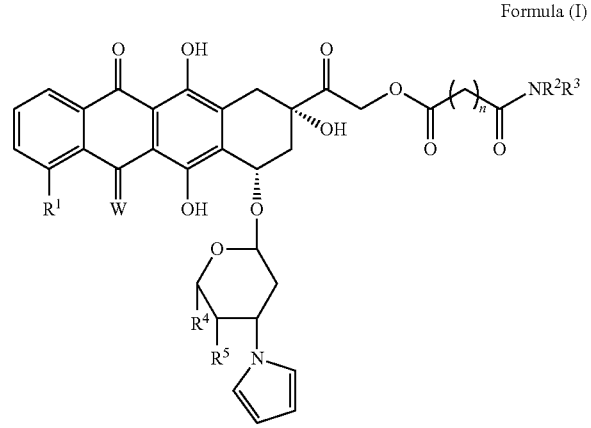

Formula (I)

wherein:

R$^1$ is selected from the group consisting of H, C$_{1-4}$alkyl, and C$_{1-4}$alkoxy;

R$^2$ is selected from the group consisting of H, aryl, heteroaryl, (C$_{1-4}$alkyleneoxy)$_m$C$_{1-4}$alkyl, heterocyclyl, C$_{1-4}$alkyl, and sulfonyl;

R$^3$ is selected from the group consisting of H, aryl, heteroaryl, (C$_{1-4}$alkyleneoxy)$_m$C$_{1-4}$alkyl, heterocyclyl, C$_{1-4}$alkyl, and sulfonyl;

or NR$^2$R$^3$ represents heterocyclyl;

m is selected from the group consisting of 0, 1, 2, 3, 4, 5, 6, 7, 8, 9, 10, and 11;

W is selected from the group consisting of O and NH;

R$^4$ is selected from the group consisting of H, F and C$_{1-4}$alkyl;

R$^5$ is selected from the group consisting of H, F, C$_{1-4}$alkyl and OR$^6$, wherein R$^6$ is selected from the group consisting of H and tetrahydropyran-2-yl; and n is selected from the group consisting of 1, 2 and 3.

In some embodiments, R$^1$ in the compound represented by formula (I) is selected from the group consisting of H and OCH$_3$.

In some embodiments, W in the compound represented by formula (I) is O.

In some embodiments, R$^4$ in the compound represented by formula (I) is CH$_3$.

In some embodiments, R$^5$ in the compound represented by formula (I) is selected from the group consisting of OH and (tetrahydropyran-2-yl)oxy.

In some embodiments, R$^2$ in the compound represented by formula (I) is selected from the group consisting of H, methyl, ethyl, (morpholinylmethyl)phenyl, 4-((morpholin-1-yl)methyl)phenyl, (dimethylaminomethyl)phenyl, 4-((dimethylamino)methyl)phenyl, 2-(2-(dimethylamino)ethoxy)ethyl, morpholin-1-yl, piperidin-1-yl, tetrahydropyrrol-1-yl, 4-(2-hydroxyethyl)piperazin-1-yl, (4-methylpiperazin)-1-yl, (4-ethylpiperazin)-1-yl, 2-(tetrahydropyrrol-1-yl)ethyl, 3-(tetrahydropyrrol-1-yl)propyl, (2-(morpholin-1-yl)pyridin)-4-yl, (2-(morpholin-1-yl)pyridin)-5-yl, pyridin-2-yl, pyridin-3-yl, pyridin-4-yl, (pyridin-4-yl)methyl, (pyridin-3-yl)methyl, (pyridin-2-yl)methyl, 2-(pyridin-4-yl)ethyl, 2-(pyridin-3-yl)ethyl, 2-(pyridin-2-yl)ethyl, 2-(pyridin-4-yl) propyl, 2-(pyridin-3-yl)propyl, 2-(pyridin-2-yl)propyl, 2-((4-sulfamido)phenyl)ethyl, (3-(dimethylamino)propyl) piperazin-1-yl, 3-((4-sulfamido)phenyl)propyl, 3-((4-methyl)piperazin-1-yl)propyl, 3-((4-ethyl)piperazin-1-yl) propyl, 3-((4-propyl)piperazin-1-yl)propyl, 2-((4-methyl) piperazin-1-yl)ethyl, 2-((4-ethyl)piperazin-1-yl)ethyl, 2-((4-propyl)piperazin-1-yl)ethyl, 2-(dimethylamino)ethyl, 2-(diethylamino)ethyl$_2$, 2-(dipropylamino)ethyl, 2-(piperidin-1-yl)ethyl, 2-(morpholin-1-yl)ethyl, 2-(tetrahydropyrrol-1-yl)ethyl, 3-(dimethylamino)propyl, 3-(diethylamino) propyl, 3-(dipropylamino)propyl, 3-(piperidin-1-yl)propyl, 3-(morpholin-1-yl)propyl, 3-(tetrahydropyrrol-1-yl)propyl, 4-(dimethylamino)butyl, 4-(diethylamino)butyl, 4-(dipropylamino)butyl, 4-(piperidin-1-yl)butyl, 4-(morpholin-1-yl)butyl, 4-(tetrahydropyrrol-1-yl)butyl, 2-(2-(2-(2-(dimethylamino)ethoxy)ethoxy)ethoxy)ethyl, 2-(2-(2-(2-(diethylamino)ethoxy)ethoxy)ethoxy)ethyl, 2-(2-(2-(2-(dipropylamino)ethoxy)ethoxy)ethoxy)ethyl, 2-(2-(2-(2-(piperidin-1-yl)ethoxy)ethoxy)ethoxy)ethyl, 2-(2-(2-(2-(morpholin-1-yl)ethoxy)ethoxy)ethoxy)ethyl, 2-(2-(2-(2-(tetrahydropyrrol-1-yl)ethoxy)ethoxy)ethoxy)ethyl, 2-(2-(2-(dimethylamino)ethoxy)ethoxy)ethyl, 2-(2-(2-(diethylamino)ethoxy)ethoxy)ethyl, 2-(2-(2-(dipropylamino)ethoxy)ethoxy)ethyl, 2-(2-(2-(piperidin-1-yl)ethoxy)ethoxy)ethyl, 2-(2-(2-(morpholin-1-yl)ethoxy) ethoxy)ethyl, 2-(2-(2-(tetrahydropyrrol-1-yl)ethoxy)ethoxy) ethyl, 6-purinyl, mesyl, benzenesulfonyl, pyrazin-2-yl, pyrimidin-2-yl, 2-hydroxyethyl, 2-(2-hydroxyethoxy)ethyl, 2-(2-(2-(2-(2-(2-(2-(2-(2-(2- hydroxyethoxy)ethoxy) ethoxy)ethoxy)ethoxy)ethoxy)ethoxy)ethoxy)ethoxy) ethoxy)ethoxy)ethyl, 2-(2-(2-(2-(2-(2-(2-(2-(2-hydroxyethoxy)ethoxy)ethoxy)ethoxy)ethoxy)ethoxy) ethoxy)ethyl, 2-(2-(2-(2-(2-(2-(2-(2-hydroxyethoxy)ethoxy) ethoxy)ethoxy)ethoxy)ethoxy)ethoxy)ethyl, 2-(2-(2-(2-(2-(2-(2-methoxy)ethoxy)ethoxy)ethoxy)ethoxy)ethoxy) ethoxy)ethoxy)ethyl, and 2-(2-(2-(2-hydroxyethoxy) ethoxy)ethoxy)ethyl.

In some embodiments, R$^3$ in the compound represented by formula (I) is selected from the group consisting of H, methyl, ethyl, (morpholinylmethyl)phenyl, 4-((morpholin-1-yl)methyl)phenyl, (dimethylaminomethyl)phenyl, 4-((dimethylamino)methyl)phenyl, 2-(2-(dimethylamino)ethoxy) ethyl, morpholin-1-yl, piperidin-1-yl, tetrahydropyrrol-1-yl, 4-(2-hydroxyethyl)piperazin-1-yl, (4-methylpiperazin)-1-yl, (4-ethylpiperazin)-1-yl, 2-(tetrahydropyrrol-1-yl)ethyl, 3-(tetrahydropyrrol-1-yl)propyl, (2-(morpholin-1-yl)pyridin)-4-yl, (2-(morpholin-1-yl)pyridin)-5-yl, pyridin-2-yl, pyridin-3-yl, pyridin-4-yl, (pyridin-4-yl)methyl, (pyridin-3-yl)methyl, (pyridin-2-yl)methyl, 2-(pyridin-4-yl)ethyl, 2-(pyridin-3-yl)ethyl, 2-(pyridin-2-yl)ethyl, 2-(pyridin-4-yl) propyl, 2-(pyridin-3-yl)propyl, 2-(pyridin-2-yl)propyl, 2-((4-sulfamido)phenyl)ethyl, (3-(dimethylamino)propyl) piperazin-1-yl, 3-((4-sulfamido)phenyl)propyl, 3-((4-methyl)piperazin-1-yl)propyl, 3-((4-ethyl)piperazin-1-yl) propyl, 3-((4-propyl)piperazin-1-yl)propyl, 2-((4-methyl) piperazin-1-yl)ethyl, 2-((4-ethyl)piperazin-1-yl)ethyl, 2-((4-propyl)piperazin-1-yl)ethyl, 2-(dimethylamino)ethyl, 2-(diethylamino)ethyl$_2$, 2-(dipropylamino)ethyl, 2-(piperidin-1-yl)ethyl, 2-(morpholin-1-yl)ethyl, 2-(tetrahydropyrrol-1-yl)ethyl, 3-(dimethylamino)propyl, 3-(diethylamino) propyl, 3-(dipropylamino)propyl, 3-(piperidin-1-yl)propyl, 3-(morpholin-1-yl)propyl, 3-(tetrahydropyrrol-1-yl)propyl, 4-(dimethylamino)butyl, 4-(diethylamino)butyl, 4-(dipropyl amino)butyl, 4-(piperidin-1-yl)butyl, 4-(morpholin-1-yl)butyl, 4-(tetrahydropyrrol-1-yl)butyl, 2-(2-(2-(2-(dimethylamino)ethoxy)ethoxy)ethoxy)ethyl, 2-(2-(2-(2-(diethylamino)ethoxy)ethoxy)ethoxy)ethyl, 2-(2-(2-(2-(dipropylamino)ethoxy)ethoxy)ethoxy)ethyl, 2-(2-(2-(2-(piperidin-1-yl)ethoxy)ethoxy)ethoxy)ethyl, 2-(2-(2-(2-(morpholin-1-yl)ethoxy)ethoxy)ethoxy)ethyl, 2-(2-(2-(2-(tetrahydropyrrol-1-yl)ethoxy)ethoxy)ethoxy)ethyl, 2-(2-(2-(dimethylamino)ethoxy)ethoxy)ethyl, 2-(2-(2-(diethylamino)ethoxy)ethoxy)ethyl, 2-(2-(2-(dipropylamino)ethoxy)ethoxy)ethyl, 2-(2-(2-(piperidin-1-yl)ethoxy)ethoxy)ethyl, 2-(2-(2-(morpholin-1-yl)ethoxy)ethoxy)ethyl, 2-(2-(2-(tetrahydropyrrol-1-yl)ethoxy)ethoxy)ethyl, 6-purinyl, mesyl, benzenesulfonyl, pyrazin-2-yl, pyrimidin-2-yl, 2-hydroxyethyl, 2-(2-hydroxyethoxy)ethyl, 2-(2-(2-(2-(2-(2-(2-(2-(2-(2- hydroxyethoxy)ethoxy)ethoxy)ethoxy)ethoxy)ethoxy)ethoxy)ethoxy)ethoxy)ethyl, 2-(2-(2-(2-(2-(2-(2-(2-(2-hydroxyethoxy)ethoxy)ethoxy)ethoxy)ethoxy)ethoxy)ethoxy)ethoxy)ethyl, 2-(2-(2-(2-(2-(2-(2-(2-hydroxyethoxy)ethoxy)ethoxy)ethoxy)ethoxy)ethoxy)ethoxy)ethyl, 2-(2-(2-(2-(2-(2-(2-methoxy)ethoxy)ethoxy)ethoxy)ethoxy)ethoxy)ethoxy)ethoxy)ethyl, and 2-(2-(2-(2-hydroxyethoxy)ethoxy)ethoxy)ethyl.

In some embodiments, $NR^2R^3$ in the compound represented by formula (I) is selected from the group consisting of piperidin-1-yl, morpholin-1-yl, tetrahydropyrrol-1-yl, (4-(2-hydroxyethyl))piperazin-1-yl, (4-methyl)piperazin-1-yl, (4-ethyl)piperazin-1-yl, (4-propyl)piperazin-1-yl, 4-(3-hydroxypropyl)piperazin-1-yl, 3-(morpholin-1-yl)propyl, adenine-1-yl, (4-(3-(dimethylamino)propyl)piperazin)-1-yl, (4-(2-(dimethylamino)ethyl)piperazin)-1-yl, (4-(3-(diethylamino)propyl)piperazin)-1-yl, (4-(2-(diethylamino)ethyl)piperazin)-1-yl, (4-(2-(piperidin-1-yl)ethyl)piperazin)-1-yl, (4-(3-(piperidin-1-yl)propyl)piperazin)-1-yl, (4-(2-(morpholin-1-yl)ethyl)piperazin)-1-yl, (4-(3-(morpholin-1-yl)propyl)piperazin)-1-yl, (4-(2-(tetrahydropyrrol-1-yl)ethyl)piperazin)-1-yl, and (4-(3-(tetrahydropyrrol-1-yl)propyl)piperazin)-1-yl.

In still another aspect, the present application relates to compounds selected from the group consisting of:

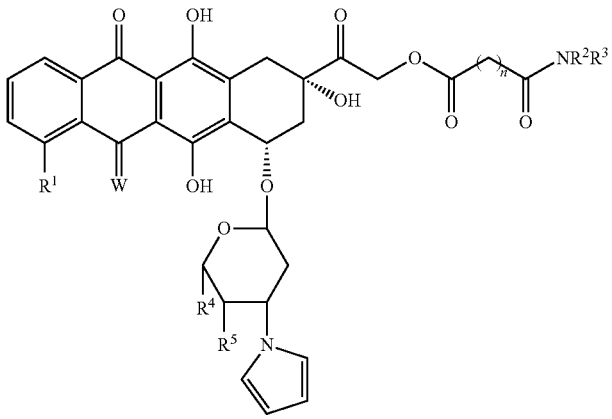

| No. | n | $NR^2R^3$ |
|---|---|---|
| 1 | 3 | 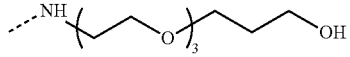 |
| 2 | 2 | 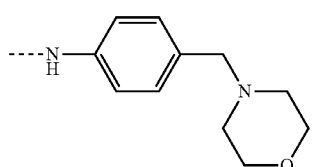 |
| 3 | 3 | 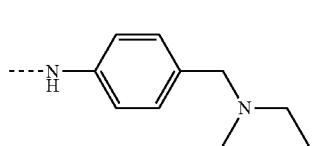 |
| 4 | 2 | 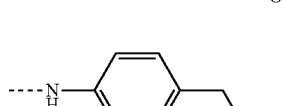 |

-continued
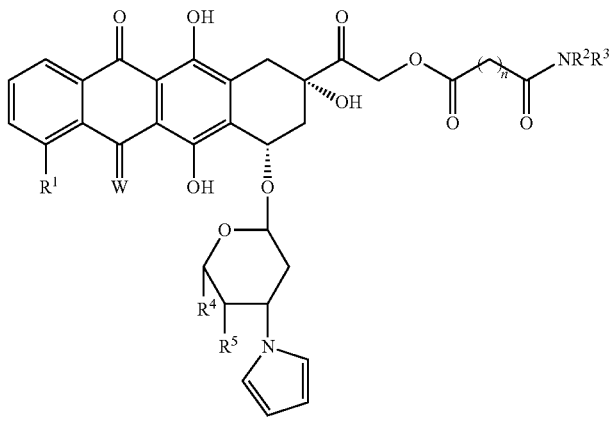
| No. | n | NR²R³ |
|---|---|---|
| 5 | 3 | ----NH—⟨C₆H₄⟩—CH₂—N(CH₃)₂ |
| 6 | 2 | ----NH—CH₂CH₂—O—CH₂CH₂—N(CH₃)₂ |
| 7 | 3 | ----NH—CH₂CH₂—O—CH₂CH₂—N(CH₃)₂ |
| 8 | 2 | ----N(piperazine)—CH₂CH₂OH |
| 9 | 3 | ----N(piperazine)—CH₂CH₂OH |
| 10 | 2 | ----NH—N(morpholine) |
| 11 | 3 | ----NH—N(morpholine) |
| 12 | 2 | ----NH—CH₂CH₂CH₂—N(morpholine) |
| 13 | 3 | ----NH—CH₂CH₂CH₂—N(morpholine) |
| 14 | 2 | ----NH—N(4-methylpiperazine) |
| 15 | 3 | ----NH—N(4-methylpiperazine) |

-continued
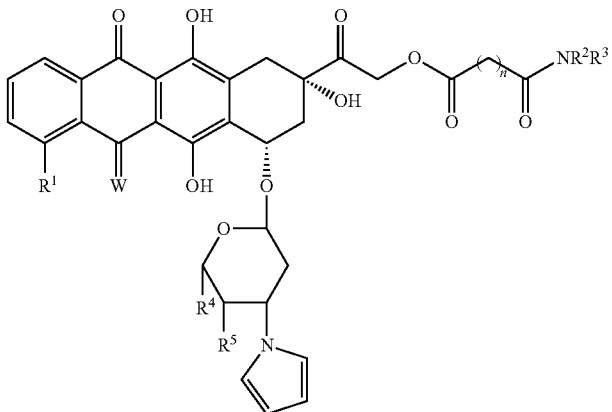
| No. | n | NR²R³ |
|---|---|---|
| 16 | 2 | ----NH-CH₂CH₂-pyrrolidine |
| 17 | 3 | ----NH-CH₂CH₂-pyrrolidine |
| 18 | 2 | ----NH-(CH₂)₃-pyrrolidine |
| 19 | 3 | ----NH-(CH₂)₃-pyrrolidine |
| 20 | 2 | ----NH-(5-pyridyl)-2-morpholino |
| 21 | 3 | ----NH-(5-pyridyl)-2-morpholino |
| 22 | 2 | ----NH-(4-pyridyl) |
| 23 | 3 | ----NH-(4-pyridyl) |
| 24 | 2 | ----NH-(3-pyridyl) |
| 25 | 3 | ----NH-(3-pyridyl) |
| 26 | 2 | ----NH-CH₂-(4-pyridyl) |

-continued
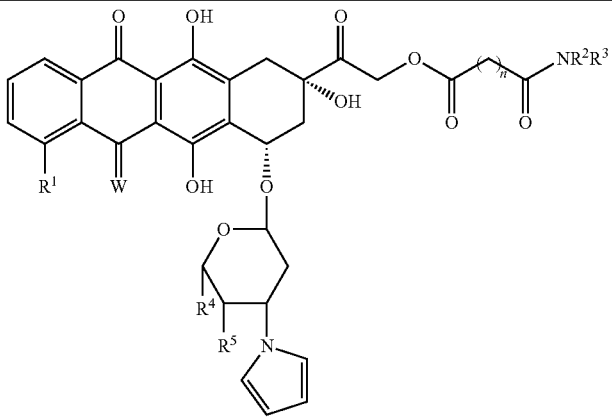
| No. | n | NR²R³ |
|---|---|---|
| 27 | 3 | ----NH-CH₂-(4-pyridyl) |
| 28 | 2 | ----NH-CH₂-(3-pyridyl) |
| 29 | 3 | ----NH-CH₂-(3-pyridyl) |
| 30 | 2 | ----HN-CH₂-(2-pyridyl) |
| 31 | 3 | ----HN-CH₂-(2-pyridyl) |
| 32 | 2 | ----NH-CH₂CH₂-(4-pyridyl) |
| 33 | 3 | ----NH-CH₂CH₂-(4-pyridyl) |
| 34 | 2 | ----NH-CH₂CH₂-(2-pyridyl) |
| 35 | 3 | ----NH-CH₂CH₂-(2-pyridyl) |
| 36 | 2 | ----NH-CH₂CH₂-(3-pyridyl) |
| 37 | 3 | ----NH-CH₂CH₂-(3-pyridyl) |

-continued
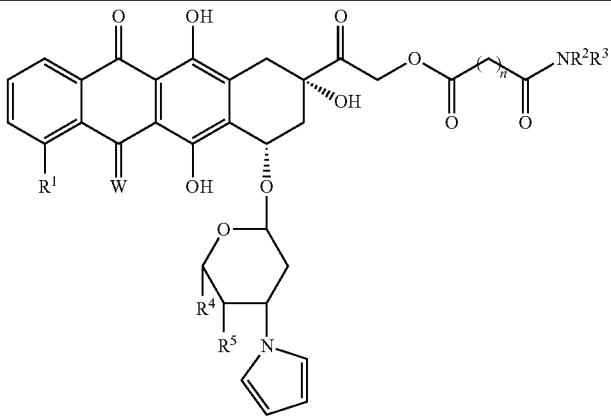
| No. | n | NR²R³ |
|-----|---|-------|
| 38 | 2 | —NH—CH₂CH₂—C₆H₄—SO₂NH₂ |
| 39 | 3 | —NH—CH₂CH₂—C₆H₄—SO₂NH₂ |
| 40 | 2 | 4-ethylpiperazin-1-yl |
| 41 | 3 | 4-ethylpiperazin-1-yl |
| 42 | 2 | 6-aminopurin-6-yl (NH-adenine) |
| 43 | 3 | 6-aminopurin-6-yl (NH-adenine) |
| 44 | 2 | 4-(3-dimethylaminopropyl)piperazin-1-yl |
| 45 | 3 | 4-(3-dimethylaminopropyl)piperazin-1-yl |
| 46 | 2 | —NH—(CH₂)₃—(4-methylpiperazin-1-yl) |
| 47 | 3 | —NH—(CH₂)₃—(4-methylpiperazin-1-yl) |

-continued
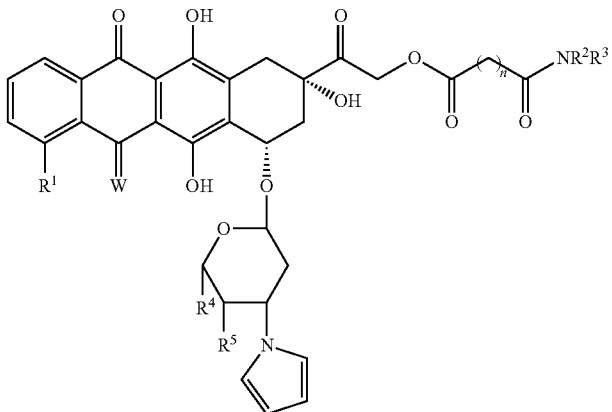
| No. | n | NR²R³ |
|---|---|---|
| 48 | 2 | ----NH-CH₂CH₂-N(CH₃)₂ |
| 49 | 3 | ----NH-CH₂CH₂-N(CH₃)₂ |
| 50 | 2 | ----N(CH₂CH₂N(CH₃)₂)₂ |
| 51 | 3 | ----N(CH₂CH₂N(CH₃)₂)₂ |
| 52 | 2 | ----NH-CH₂CH₂-O-CH₂CH₂-O-CH₂CH₂-O-CH₂CH₂-N(CH₃)₂ |
| 53 | 3 | ----NH-CH₂CH₂-O-CH₂CH₂-O-CH₂CH₂-O-CH₂CH₂-N(CH₃)₂ |
| 54 | 2 | ----NH-pyrazinyl |
| 55 | 3 | ----NH-pyrazinyl |
| 56 | 2 | ----NH-pyridin-2-yl |

-continued
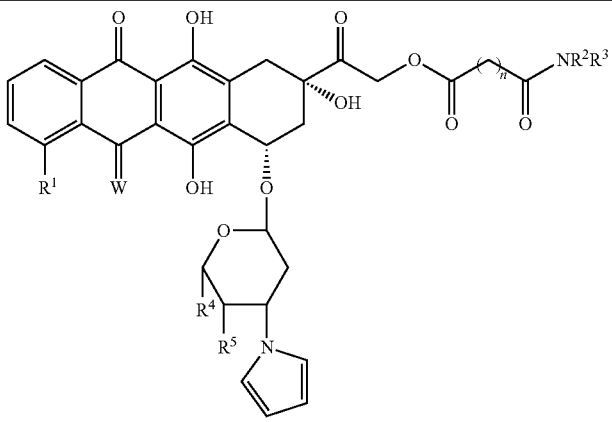
| No. | n | NR²R³ |
|---|---|---|
| 57 | 3 | ----NH-(2-pyridyl) |
| 58 | 2 | ----HN-(2-pyrimidinyl) |
| 59 | 3 | ----HN-(2-pyrimidinyl) |
| 60 | 2 | ----NH-CH₂CH₂OH |
| 61 | 3 | ----NH-CH₂CH₂OH |
| 62 | 2 | ----NH-CH₂CH₂-O-CH₂CH₂-OH |
| 63 | 3 | ----NH-CH₂CH₂-O-CH₂CH₂-OH |
| 64 | 2 | ----N(CH₂CH₂OH)₂ |
| 65 | 3 | ----N(CH₂CH₂OH)₂ |
| 66 | 2 | NH₂ |
| 67 | 3 | NH₂ |
| 68 | 2 | NHCH₃ |
| 69 | 3 | NHCH₃ |
| 70 | 2 | N(CH₃)₂ |
| 71 | 3 | N(CH₃)₂ |

-continued
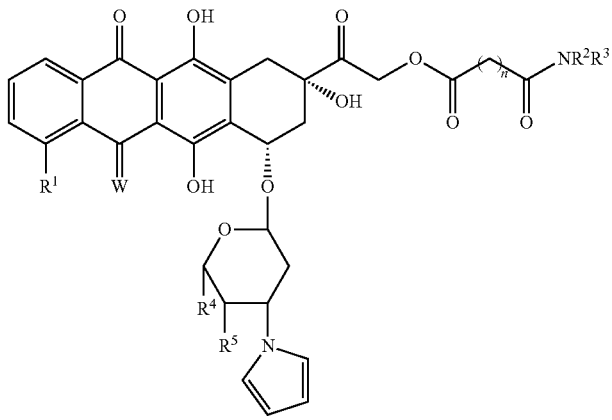
| No. | n | NR²R³ |
|---|---|---|
| 72 | 2 | morpholine (N-linked) |
| 73 | 3 | morpholine (N-linked) |
| 74 | 2 | piperidine (N-linked) |
| 75 | 2 | pyrrolidine (N-linked) |
| 88 | 2 | —NH—CH₂CH₂—morpholine |
| 90 | 2 | —NH—(CH₂CH₂O)₇—OH |
| 91 | 2 | —NH—(CH₂CH₂O)₈—OH |
| 92 | 2 | —NH—(CH₂CH₂O)₁₁—OH |
| 93 | 2 | —NH—(CH₂CH₂O)₈—OCH₃ |
| 94 | 2 | —NH—S(O)₂—CH₃ |
| 95 | 2 | —NH—S(O)₂—C₆H₅ |

77) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((4-(2-hydroxy)ethyl)piperazin-1-yl)-4-oxo-butyrato)-1-methoxy-5,12-naphthalenedione acetate;

78) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((3-(morpholin-1-yl)propyl)amino)-4-oxo-butyrato)-1-methoxy-5,12-naphthalenedione acetate;

79) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((4-methyl)piperazin-1-yl)amino)-4-oxo-butyrato)-1-methoxy-5,12-naphthalenedione acetate;

80) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(4-ethylpiperazin-1-yl)-4-oxo-butyrato)-1-methoxy-5,12-naphthalenedione acetate;

81) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((3-(4-methylpiperazin-1-yl)propyl)amino)-4-oxo-butyrato)-1-methoxy-5,12-naphthalenedione acetate;

82) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((pyridin-4-yl)methyl)amino)-4-oxo-butyrato)-1-methoxy-5,12-naphthalenedione acetate;

83) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((pyridin-3-yl)methyl)amino)-4-oxo-butyrato)-1-methoxy-5,12-naphthalenedione acetate;

84) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-2-yl)ethyl)amino)-4-oxo-butyrato)-1-methoxy-5,12-naphthalenedione acetate;

85) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-3-yl)ethyl)amino)-4-oxo-butyrato)-1-methoxy-5,12-naphthalenedione acetate;

86) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-4-yl)ethyl)amino)-4-oxo-butyrato)-1-methoxy-5,12-naphthalenedione acetate;

87) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(4-(3-(dimethyl amino)propyl)piperazin-1-yl)-4-oxo-butyrato)-1-methoxy-5,12-naphthalenedione acetate;

89) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione acetate;

96) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione phosphate; and 99) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione hydrochloride.

In yet still another aspect, the present application relates to a process for preparing a compound represented by formula (I), comprising:

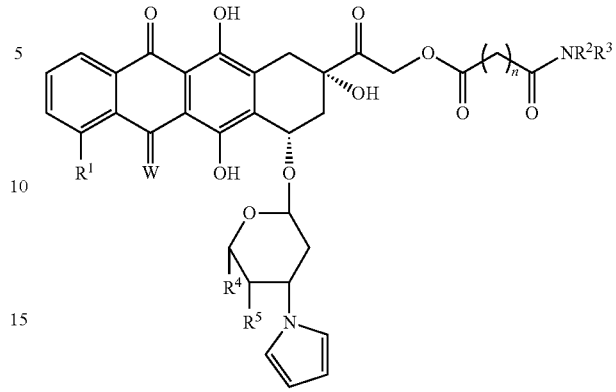

Formula (I)

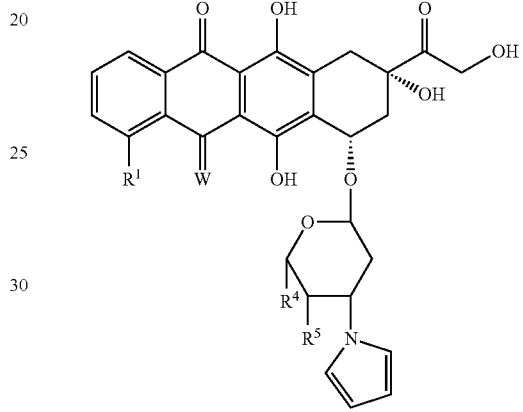

Formula (II)

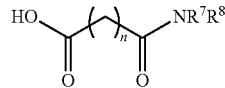

Formula (III)

reacting a compound represented by formula (II) with a compound represented by formula (III) in the presence of a condensation agent to obtain the compound represented by formula (I), wherein:

in the compound represented by formula (I), $R^1$ is selected from the group consisting of H, $C_{1-4}$alkyl, and $C_{1-4}$alkoxy; $R^2$ is selected from the group consisting of H, aryl, heteroaryl, $(C_{1-4}alkyleneoxy)_m C_{1-4}$alkyl, heterocyclyl, $C_{1-4}$alkyl, and sulfonyl; $R^3$ is selected from the group consisting of H, aryl, heteroaryl, $(C_{1-4}alkyleneoxy)_m C_{1-4}$alkyl, heterocyclyl, $C_{1-4}$alkyl, and sulfonyl; or $NR^2R^3$ represents heterocyclyl; m is selected from the group consisting of 0, 1, 2, 3, 4, 5, 6, 7, 8, 9, 10, and 11; W is selected from the group consisting of O and NH; $R^4$ is selected from the group consisting of H, F and $C_{1-4}$alkyl; $R^5$ is selected from the group consisting of H, F, $C_{1-4}$alkyl and $OR^6$, in which $R^6$ is selected from the group consisting of H and tetrahydropyran-2-yl; n is selected from the group consisting of 1, 2 and 3;

groups represented by $R^1$, W, $R^4$, $R^5$ in the compound represented by formula (II) are the same as groups represented by $R^1$, W, $R^4$, $R^5$ in the compound represented by formula (I);

n in the compound represented by formula (III) has the same meanings as n in the compound represented by formula (I); groups represented by $R^7$ and $R^8$ in the compound represented by formula (III) are the same as groups represented by R² and R³ in the compound represented by formula (I), provided that groups represented by R⁷ and R⁸ do not comprise NH or NH₂; when groups represented by R⁷ and R⁸ comprise NH or NH₂, the compound represented by formula (III) has an amino-protecting group at N-terminus, and is subject to a deprotection reaction to obtain the compound represented by formula (I).

In some embodiments, the process for preparing a compound represented by formula (I) further comprises adding an activator.

Exemplary examples of activators that can be used in the process for preparing a compound represented by formula (I) according to the present application include, but are not limited to, N-hydroxysuccinimide (HOSu), 1-hydroxy-7-azobenzotriazole (HOAt), 1-hydroxybenzotriazole (HOBt), N-hydroxyphthalimide (NHPI), N-hydroxy-1,8-naphthalimide (NHNI), pentafluorophenol (PFPOH), 2-(7-azobenzotriazole)-N,N,N',N'-tetramethyluronium hexafluorophosphate (HATU), benzotriazole-N,N,N',N'-tetramethyluronium hexafluorophosphate (HBTU), 6-chlorobenzotriazole-1,1,3,3-tetramethyluronium hexafluorophosphate (HCTU), O-(7-azabenzotriazole-1-yl)-di(tetrahydropyrrolyl)carbenium hexafluophosphate (HAPyU), O-(benzotriazole-1-yl)-di(tetrahydropyrrolyl)carbenium hexafluophosphate (HBPyU), O-benzotriazole-N,N,N',N'-tetramethyluronium tetrafluoroborate (TBTU), 2-succinimido-1,1,3,3-tetramethyluronium tetrafluoroborate (TSTU), 2-(5-norbornen-2,3-dicarboximido)-1,1,3,3-tetramethyluronium tetrafluoroborate quaternary ammonium salt (TNTU), benzotriazole-1-yloxytri(dimethylamino)phosphonium hexafluorophosphate (BOP), benzotriazol-1-yl-oxytripyrrolidino-phosphonium hexafluorophosphate (PyBOP), (3H-1,2,3-triazolo[4,5-b]pyridin-3-oxy)tri-1-pyrrolidinylphosphonium hexafluorophosphate (PyAOP), diphenylphosphinyl chloride (DPP-Cl), diphenyl phosphoryl azide (DPPA), cyanodiethylphosphate (DECP), bis(2-oxo-3-oxazolidinyl)phosphinyl chloride (BOP-Cl) and a mixture thereof.

Exemplary examples of condensation agents that can be used in the process for preparing a compound represented by formula (I) according to the present application include, but are not limited to, dicyclohexylcarbodiimide (DCC), diisopropylcarbodiimide (DIC), 1-(3-dimethylaminopropyl)-3-ethylcarbodiimide (EDCI), 2-(7-azobenzotriazole)-N,N,N',N'-tetramethyluronium hexafluorophosphate (HATU), benzotriazol-N,N,N',N'-tetramethyluronium hexafluorophosphate (HBTU), 6-chlorobenzotriazol-1,1,3,3-tetramethyluronium hexafluorophosphate (HCTU), O-(7-azabenzotriazol-1-yl)-di(tetrahydropyrrolyl)carbenium hexafluophosphate (HAPyU), O-(benzotriazol-1-yl)-di(tetrahydropyrrolyl)carbenium hexafluophosphate (HBPyU), O-benzotriazol-N,N,N',N'-tetramethyluronium tetrafluoroborate (TBTU), 2-succinimido-1,1,3,3-tetramethyluronium tetrafluoroborate (TSTU), 2-(5-norbornen-2,3-dicarboximido)-1,1,3,3-tetramethyluronium tetrafluoroborate quaternary ammonium salt (TNTU), benzotriazol-1-yloxytri(dimethylamino)phosphonium hexafluorophosphate (BOP), benzotriazol-1-yl-oxytripyrrolidino-phosphonium hexafluorophosphate (PyBOP), (3H-1,2,3-triazolo[4,5-b]pyridin-3-oxy)tri-1-pyrrolidinylphosphonium hexafluorophosphate (PyAOP), diphenylphosphinyl chloride (DPP-Cl), diphenyl phosphoryl azide (DPPA), cyanodiethylphosphate (DECP), bis(2-oxo-3-oxazolidinyl)phosphinyl chloride (BOP-Cl) and a mixture thereof.

In some embodiments, the process for preparing a compound represented by formula (I) further comprises adding a catalyst.

Exemplary examples of catalysts that can be used in the process for preparing a compound represented by formula (I) according to the present application include, but are not limited to, 4-dimethylaminopyridine, 4-pyrrolidinylpyridine and a mixture thereof.

Exemplary examples of nitrogen-protecting groups that can be used in the process for preparing a compound represented by formula (I) according to the present application include, but are not limited to, Fmoc (fluorenylmethoxycarbony), Boc (t-butyloxycarboryl), CBZ (carbobenzoxy), Tr (trityl) or Alloc (allyloxycarbonyl), Teoc (trimethylsilylethoxycarbonyl), methoxycarbonyl, ethoxycarbonyl, Pht (phthaloyl), Tos (tosyl), Ns (o/p-nitrobenzenesulfonyl), Tfa (trifluoroacetyl), pivaloyl, benzoyl, Trt (trityl), Dmb (2,4-dimethoxybenzyl), PMB (p-methoxybenzyl), and Bn (benzyl).

Exemplary examples of deprotection reactants that can be used in the process for preparing a compound represented by formula (I) according to the present application include, but are not limited to, hydrogen gas, NH₃, aminoethanol, dimethylamine, diethylamine, piperidine, piperazine, DBU, hydrochloric acid, phosphoric acid, acetic acid, formic acid, trifluoroacetic acid, methanesulfonic acid, benzenesulfonic acid, p-toluenesulfonic acid and a mixture thereof.

In some embodiments, the compound represented by formula (III) in the process for preparing a compound represented by formula (I) is obtained by a reaction of a compound represented by formula (IV) with HNR⁷R⁸,

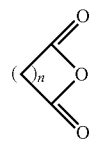

Formula (IV)

wherein:

n in the compound represented by formula (IV) has the same meanings as n in the compound represented by formula (I);

groups represented by R² and R³ in HNR⁷R⁸ are the same as groups represented by R² and R³ in the compound represented by formula (I).

In some embodiments, the process for preparing a compound represented by formula (III) further comprises adding an alkaline compound.

Exemplary examples of alkaline compounds that can be used in the process for preparing a compound represented by formula (III) according to the present application include, but are not limited to, triethylamine, pyridine, diisopropylethylamine, trimethylamine, N-methylpyrrolidine, N-methylpiperidine, N-methylmorpholine, N-ethylpyrrolidine, N-ethylpiperidine, N-ethylmorpholine and a mixture thereof.

In yet another aspect, the present application relates to a pharmaceutical composition comprising a compound represented by formula (I) or a pharmaceutically acceptable salt thereof, and a pharmaceutically acceptable carrier, Formula (I)

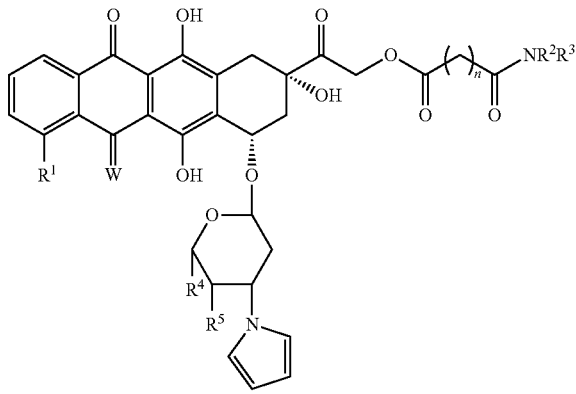

wherein:
R¹ is selected from the group consisting of H, $C_{1-4}$alkyl, and $C_{1-4}$alkoxy;
R² is selected from the group consisting of H, aryl, heteroaryl, $(C_{1-4}\text{alkyleneoxy})_m C_{1-4}$alkyl, heterocyclyl, $C_{1-4}$alkyl, and sulfonyl;
R³ is selected from the group consisting of H, aryl, heteroaryl, $(C_{1-4}\text{alkyleneoxy})_m C_{1-4}$alkyl, heterocyclyl, $C_{1-4}$alkyl, and sulfonyl;
or $NR^2R^3$ represents heterocyclyl;
m is selected from the group consisting of 0, 1, 2, 3, 4, 5, 6, 7, 8, 9, 10, and 11;
W is selected from the group consisting of O and NH;
R⁴ is selected from the group consisting of H, F and $C_{1-4}$alkyl;
R⁵ is selected from the group consisting of H, F, $C_{1-4}$alkyl and $OR^6$, wherein R⁶ is selected from the group consisting of H and tetrahydropyran-2-yl; and
n is selected from the group consisting of 1, 2 and 3.

In another aspect, the present application relates to a formulation comprising a compound represented by formula (I) or a pharmaceutically acceptable salt thereof, and a pharmaceutically acceptable carrier, Formula (I)

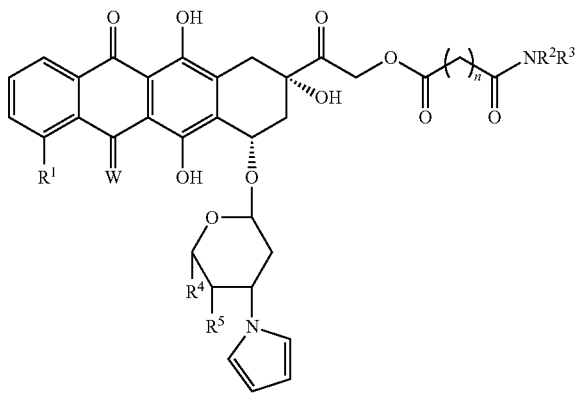

wherein:
R¹ is selected from the group consisting of H, $C_{1-4}$alkyl, and $C_{1-4}$alkoxy;
R² is selected from the group consisting of H, aryl, heteroaryl, $(C_{1-4}\text{alkyleneoxy})_m C_{1-4}$alkyl, heterocyclyl, $C_{1-4}$alkyl, and sulfonyl;

R³ is selected from the group consisting of H, aryl, heteroaryl, $(C_{1-4}\text{alkyleneoxy})_m C_{1-4}$alkyl, heterocyclyl, $C_{1-4}$alkyl, and sulfonyl;
or $NR^2R^3$ represents heterocyclyl;
m is selected from the group consisting of 0, 1, 2, 3, 4, 5, 6, 7, 8, 9, 10, and 11;
W is selected from the group consisting of O and NH;
R⁴ is selected from the group consisting of H, F and $C_{1-4}$alkyl;
R⁵ is selected from the group consisting of H, F, $C_{1-4}$alkyl and $OR^6$, wherein R⁶ is selected from the group consisting of H and tetrahydropyran-2-yl; and
n is selected from the group consisting of 1, 2 and 3.

In some embodiments, the formulation comprising a compound represented by formula (I) or a pharmaceutically acceptable salt thereof and a pharmaceutically acceptable carrier is a formulation for injection.

Exemplary examples that can be used in the formulation according to the present application include, but are not limited to, a conventional powder injection, a freeze-dried powder injection, a hydro-injection, an emulsion, a solution and a suspension.

In still another aspect, the present application relates to a method for treating and/or preventing tumor and/or cancer, comprising administering to a subject in need thereof a therapeutically effective amount of a compound represented by formula (I) or a pharmaceutically acceptable salt thereof, or administering a therapeutically effective amount of a pharmaceutical composition comprising a compound represented by formula (I) or a pharmaceutically acceptable salt and a pharmaceutically acceptable carrier, or administering a therapeutically effective amount of a formulation comprising a compound represented by formula (I) or a pharmaceutically acceptable salt and a pharmaceutically acceptable carrier, Formula (I)

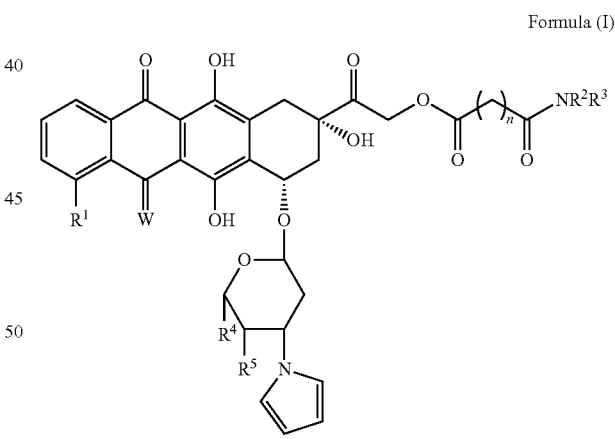

wherein:
R¹ is selected from the group consisting of H, $C_{1-4}$alkyl, and $C_{1-4}$alkoxy;
R² is selected from the group consisting of H, aryl, heteroaryl, $(C_{1-4}\text{alkyleneoxy})_m C_{1-4}$alkyl, heterocyclyl, $C_{1-4}$alkyl, and sulfonyl;
R³ is selected from the group consisting of H, aryl, heteroaryl, $(C_{1-4}\text{alkyleneoxy})_m C_{1-4}$alkyl, heterocyclyl, $C_{1-4}$alkyl, and sulfonyl;
or $NR^2R^3$ represents heterocyclyl;
m is selected from the group consisting of 0, 1, 2, 3, 4, 5, 6, 7, 8, 9, 10, and 11;

W is selected from the group consisting of O and NH;

R⁴ is selected from the group consisting of H, F and $C_{1-4}$alkyl;

R⁵ is selected from the group consisting of H, F, $C_{1-4}$alkyl and OR⁶, wherein R⁶ is selected from the group consisting of H and tetrahydropyran-2-yl; and n is selected from the group consisting of 1, 2 and 3.

Exemplary examples of tumors and/or cancers that can be treated and/or prevented by the method according to the present application include, but are not limited to, liver cancer, gastric cancer, breast cancer, lung cancer, intestine cancer, ovarian cancer, pancreatic cancer, head and neck cancer, cervical cancer, renal cancer, melanoma, prostatic cancer, brain glioma, various leukemia, lymphoma, and multiple bone marrow cancer.

The compound and a salt thereof according to the present application possess good anticancer and/or antitumor activity, and good water solubility and stability, as well as good tolerance in animal bodies. Therefore, they are prone to being developed as clinical drugs.

EXAMPLES

Although any one skilled in the art is capable of preparing the compounds of the present application according to the general techniques disclosed herein above, more specific details on synthetic techniques for the compound of the present application are provided elsewhere in this specification for conveniences. In addition, all reagents and reaction conditions employed in synthesis are known to those skilled in the art and are available from ordinary commercial sources.

Abbreviations

Su: succinimide; Bt: benzotrazol-1-yl; At: 7-azobenzotrazol-1-yl; Fmoc: fluorenylmethoxycarbonyl; Boc: t-butoxycarbonyl; CBZ: carbobenzoxy; Tr: trimethylphenyl; Alloc: allyloxycarbonyl; DBU: 1,8-diazacyclo[5,4,0]hendecene-7; DIEA: diisopropylethylamine; DMAP: 4-dimethylaminopyridine; EDC-HCl: 1-(3-dimethyl aminopropyl)-3-ethylcarbodiimide hydrochloride; HOAt: N-hydroxy-7-azobenzotriazole; DCC: dicyclohexylcarbodiimide; DIC: N,N-diisopropylcarbodiimide. NCI-H446: human small cell lung cancer cell line; BxPC-3: human pancreatic cancer cell line; SK-OV-3: human ovarian cancer cell line; MDA-MB-453: human breast cancer cell line; 22Rv1: human prostate cancer cell line; A375: human cutaneous melanoma cell line; A431: human epidermal carcinoma cell line; MCF-7: human breast cancer cell line; NCI-446: human small cell lung cancer cell line; NCI-H460: human large cell lung cancer cell line; B16: mouse melanoma cell line; 786-O: human kidney clear cell adenocarcinoma cell line; DU-145: prostate cancer cell line; Hep3B: liver cancer cell line; SK-Br-3: human breast cancer cell line; MTT: nitroblue tetrazolium; McCoy's 5A: McCoy's 5A Medium; FBS: fetal calf serum; PBS: phosphate buffer, pH 7.4; EDTA: ethylenediamine tetraacetic acid; DMSO: dimethyl sulfoxide; RPMI-1640: RPMI-1640 Medium; SRB: sulforhodamine; TCA: trichloroacetic acid; ddH₂O: double distilled water; Tris: trihydroxymethylaminomethane; L15: Leibovitz's L-15 Medium; compound A: 3'-pyrrolyldoxorubicin-14-oxo-succinic acid monoester.

The numberings of the substituents in the present application are indicated as follows.

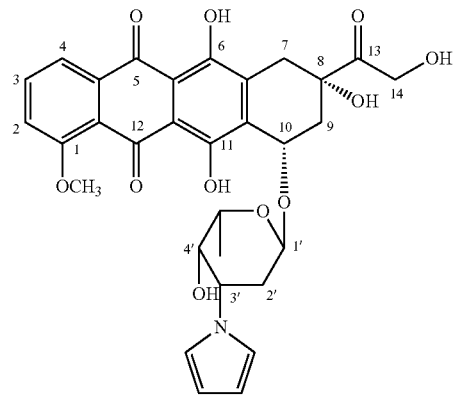

Preparation 1

3'-Pyrrolyldoxorubicin 10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-8-Hydroxyacetyl-1-Methoxy-5,12-Naphthalenedione To a three-neck flask (1 L) were added doxorubicin hydrochloride (3.076 g), distilled water (300 mL) and 1,2-dichloroethane (300 mL), 2,5-dimethoxytetrahydrofuran (30 mL) and glacial acetic acid (6 mL). The mixture was heated and refluxed for 45 min under the protection of argon gas until the reaction was completed. The reaction was cooled to the room temperature. The reaction solution was poured into ice water (200 mL), and then stood to separate. The organic phase was washed with saturated saline (200 mL) once, dried over anhydrous magnesium sulfate, filtered and rotary-evaporated to dryness. To the aqueous phase was added 5% sodium bicarbonate aqueous solution (100 mL) while being stirred in an ice bath, and then extracted with chloroform (50 mL×3). The chloroform layers were combined and washed with saturated saline (100 mL) once, filtered and rotary-evaporated to remove the solvent. The resultant crude was combined with the crude obtained above. The resultant mixture was purified with column chromatography, eluting with chloroform:methanol=35:1, to give the product (2.91 g). MS: 592 (M-1)

Preparation 2

4-(4-Nitrobenzyl)Morpholine

To a reaction flask was added p-nitrobenzyl bromide (72.084 g). Dichloromethane (470 mL, dried via molecular sieve) was added to dissolve p-nitrobenzyl bromide. Anhydrous potassium carbonate (91.909 g) was added. The mixture was cooled in an ice bath under the protection of argon gas. After 20 min, to the reaction flask was dropwise added morpholine (over about 30 min). After the addition was completed, the ice bath was removed. The resultant mixture was stirred overnight at the room temperature. After the reaction was completed, water (150 mL) was added. The pH of the mixture was adjusted with 5% citric acid aqueous solution to 4-5 under stirring. After standing to separate, the organic phase was washed with water (260 mL×1), dried over anhydrous MgSO₄ for half an hour, and then filtered. The filtrate was concentrated, and dried under reduced pressure by oil pump, to give the target compound (71.9 g, yield 97.16%).

Preparation 3

4-(Morpholinylmethyl)Aniline

To a reaction flask were added 4-(4-nitrobenzyl)morpholine (37.4 g) and absolute ethanol (520 mL). The mixture was mechanically stirred, and then acetic acid (34 mL) was added. The resultant mixture was warmed in an oil bath. The solution became clear at 40° C. To 1 N hydrochloric acid (HCl) (84 mL) was added iron powders (48.002 g), and stirred for 10 min, filtered by suction. The filter cake was washed with absolute ethanol, and then added into the reaction flask. The mixture was warmed in an oil bath to reflux, and maintained under reflux until the reaction was completed (about 3 hr). After the reaction was completed, the reaction solution was filtered by suction. The filtrate was concentrated, and then dissolved in ethyl acetate (400 mL) and water (400 mL). The mixture was mixed and then stood to separate. The organic layer was discarded. The aqueous phase was washed with dichloromethane (100 mL×3). The pH was adjusted with NaOH solids to 9. Lots of brown solids precipitated from the solution, The solids were filtered by suction. The filter cake was washed with distilled water (20 mL×2) and then discarded. The pH of the filtrate was adjusted with sodium hydroxide (NaOH) to 13. The resultant solution was extracted with dichloromethane (100 mL×2). The organic phase was directly concentrated to give the target compound.

Preparation 4

5-(4-(Morpholinylmethyl)Phenylamino)-5-Oxopentanoic Acid

To a reaction flask was added 4-(morpholinylmethyl) aniline (960 mg). Dichloromethane (7.6 mL, dried via molecular sieve) was added to dissolve 4-(morpholinylmethyl)aniline. The solution was stirred under the protection of argon gas. To the reaction flask were added glutaric anhydride (741 mg), DIEA (1.1 mL) and DMAP (62 mg). The mixture was stirred overnight at the room temperature. After the reaction was completed, dichloromethane (50 mL) and distilled water (30 mL) were added. The pH of the resultant mixture was adjusted with NaOH solids to 13. The resultant solution was mixed homogeneously again, and stood to separate. The pH of the aqueous phase was adjusted with HCl to 3. The solution was frozen to dry. The resultant solids were washed with absolute ethanol (50 mL) and filtered. The resultant filtrate was concentrated and redissolved in dichloromethane. The resultant solution was concentrated again to remove the residual absolute ethanol. The resultant product was directly dried under reduced pressure to give the target compound.

Preparation 5

N,N-Dimethyl(4-Nitrophenyl)Methylamine

To a reaction flask were added nitrobenzyl bromide (6.291 g) and dichloromethane (50 mL). Anhydrous potassium carbonate (12.423 g) and dimethylamine hydrochloride (4.891 g) were successively added to the reaction flask. The mixture was stirred overnight at the room temperature. After the reaction was completed, the reaction solution was filtered by suction. The filter cake was washed with dichloromethane (10 mL). The filtrate was washed three times with distilled water (50 mL×1, 30 mL×2). The organic phase was directly concentrated and dried under reduced pressure by oil pump to give an oil (4.553 g).

Preparation 6

4-((Dimethylamino)Methyl)Aniline

To a reaction flask was added N,N-dimethyl(4-nitrophenyl)methyamine (4.553 g). Anhydrous ethanol was added to dissolve N,N-dimethyl(4-nitrophenyl)methyamine. After adding acetic acid (5.2 mL), the mixture was mechanically stirred. To 1 N HCl (40 mL) was added iron powders (11.339 g). The iron powders were immersed for 10 min and filtered by suction. The filter cake was washed with absolute ethanol and then added into the reaction flask. The mixture was warmed in an oil bath to reflux, and maintained under reflux until the reaction was completed (about 35 min). After the reaction was completed, the reaction solution was filtered by suction. The filter cake was washed with absolute ethanol. The filtrate was concentrated and then added into distilled water (100 mL). The pH of the mixture was adjusted with NaOH to 14. Lots of solids were precipitated. The solids were filtered by suction. The filtrate was extracted with dichloromethane (100 mL×1), and the aqueous phase was discarded. To the organic phase was added distilled water (60 mL). The pH was adjusted with 2 N HCl to 2. The resultant product was mixed and stood to separate. The organic phase was discarded. The pH of the aqueous phase was adjusted with NaOH to 7. The mixture was extracted with dichloromethane (40 mL×2) and the aqueous phase was discarded. The organic phase was washed with distilled water (40 mL×1) once and the aqueous phase was discarded. The organic phase was directly concentrated to give the target compound.

Preparation 7

T-Butyl 2-(2-Hydroxyethoxy)Ethylcarbamate

To a single-neck flask was added 2-(2-aminoethoxy) ethanol (10.500 g). Tetrahydrofuran (25 mL) was added to dissolve 2-(2-aminoethoxy)ethanol. Anhydrous sodium carbonate (5.300 g) was dissolved in distilled water (30 mL). The solution was added into the single-neck flask and cooled in an ice bath. Di-t-butyl dicarbonate (28.340 g) was dissolved in tetrahydrofuran (70 mL). The resultant solution was slowly dropwise added in the reaction system (for about 1 hr). After the addition, the mixture was stirred for 1.5 hr. After the reaction was completed, the reaction solution was filtered by suction. The filter cake was washed with tetrahydrofuran twice and then discarded. The filtrate was concentrated, then dissolved in ethyl acetate (150 mL) and distilled water (100 mL). The solution was mixed and then stood to separate. The aqueous phase was washed again with ethyl acetate (100 mL×2) twice. All the organic phases were combined, dried over $MgSO_4$, filtered and concentrated to give the target compound.

Preparation 8

2-(2-T-Butoxycarbonylamino)Ethoxy)Ethyl-4-Methylbenzenesulfonate

To a single-neck flask (250 mL) were added t-butyl 2-(2-hydroxyethoxy)ethylcarbamate (20.5 g) and p-toluenesulfonyl chloride (28.575 g). Tetrahydrofuran (50 mL) was added to dissolve the mixture. The resultant solution was cooled in an ice bath. Sodium hydroxide (8.000 g) was dissolved in distilled water (32 g). The solution was dropwise added in the reaction flask. The mixture was stirred overnight. After the reaction was completed, the reaction solution was concentrated (to remove tetrahydrofuran). To the resultant product were added ethyl acetate (150 mL) and distilled water (100 mL). The solution was mixed homogeneously and stood to separate. The organic phase was washed with saturated NaCl once, dried over $MgSO_4$ for 30 min, filtered and concentrated to give an oil. After standing overnight, solids were precipitated. The solids were filtered by suction. The filter cake was eluted with ethyl acetate twice to give the target compound.

Preparation 9

T-Butyl 2-(2-(Dimethylamino)Ethoxy)Ethylcarbamate

To a reaction flask was added dimethylamine hydrochloride (30.922 g). Distilled water (50 mL) was added to dissolve dimethylamine hydrochloride. The mixture was cooled in an ice bath. To the reaction flask was added 20% sodium hydroxide aqueous solution (76.885 g). After stirring for 20 min, 2-(2-t-butoxycarbonylamino)ethoxy)ethyl 4-methylbenzenesulfonate (13.621 g) was dissolved in absolute ethanol (50 mL) and tetrahydrofuran (30 mL). To the reaction flask was added the resultant solution. The mixture reacted overnight. The reaction flask was moved to an oil bath at 40° C. The mixture was stirred for 2.5 hr. After the reaction was completed, the organic solvent was removed by concentration. The crude product was extracted with ethyl acetate (150 mL×1) once. The pH of the aqueous phase was adjusted with NaOH to 9. The aqueous phase was extracted with ethyl acetate (100 mL×1) once. The organic phases were combined, dried over $MgSO_4$ for 30 min, then filtered and concentrated to give the target compound.

Preparation 10

2-(2-(Dimethylamino)Ethoxy)Ethylamine

In a reaction flask t-butyl 2-(2-(dimethylamino)ethoxy) ethylcarbamate was dissolved in dichloromethane (70 mL). The mixture was cooled in an ice bath under the protection of argon gas. To the reaction flask was dropwise added trifluoroacetic acid (17 mL). The mixture reacted overnight. After the reaction was completed, the reaction solution was extracted with distilled water (100 mL) once. The organic phase was discarded. The pH of the aqueous phase was adjusted with NaOH to 13. The aqueous phase was extracted with dichloromethane (150 mL×3) three times. The resultant organic phase was directly concentrated to give the target compound.

Preparation 11

T-Butyl-Di(2-Hydroxyethyl)Carbamate

To a reaction flask was added dihydroxyethylamine (31.5 g). Tetrahydrofuran (50 mL) and distilled water (50 mL) were added to dissolve dihydroxyethylamine. Di-t-butyl dicarbonate (85.0 g) was dissolved in tetrahydrofuran (80 mL). The resultant solution was dropwise added into the reaction flask in an ice bath (over 2 hr). After the addition was completed, the mixture was stirred until the reaction was completed (for about 1.5 hr). The reaction solution was concentrated, then dissolved in dichloromethane (200 mL) and distilled water (150 mL), mixed and stood to separate. The aqueous layer was extracted with dichloromethane (100 mL×4) four times. All the organic phases were combined and concentrated to directly use in the subsequent reaction.

Preparation 12

T-Butyl-Di(2-P-Toluene Sulfonatoethyl)Carbamate

To a reaction flask were added t-butyl-di(2-hydroxyethyl) carbamate (61.5 g) and p-toluenesulfonyl chloride (137.2 g). Tetrahydrofuran (200 mL) was added to dissolve t-butyl-di (2-hydroxyethyl)carbamate and p-toluenesulfonyl chloride. The solution was cooled in an ice bath. 20% sodium hydroxide aqueous solution (216 g) was dropwise added into the reaction flask (over 70 min). The resultant mixture was stirred overnight in an ice bath. After the reaction was completed, the pH of the reaction solution was adjusted with 20% NaOH aqueous solution to 13. The solution was stirred for 2 hr in an oil bath at 40° C. The reaction solution was concentrated. Dichloromethane (250 mL) was added to dissolve the concentrated reaction solution. The resultant solution was washed with distilled water (100 mL) once. The organic phase was directly concentrated to give the crude target compound.

Preparation 13

T-Butyl Di(2-(Dimethylamino)Ethyl)Carbamate

To a reaction flask was added dimethylamine hydrochloride (116.1 g). Distilled water (60 mL) was added to dissolve dimethylamine hydrochloride. The solution was cooled in an ice bath. 20% sodium hydroxide aqueous solution (284.8 g) was added into the reaction flask (over 70 min). After the addition was completed, the mixture was stirred for 20 min. T-butyl-di(2-p-toluenesulfonatoethyl)carbamate (73.2 g) was dissolved in tetrahydrofuran (200 mL). The resultant mixture was added to the reaction flask and stirred in an oil bath at 40° C. until the reaction was completed. The reaction solution was concentrated and washed with ethyl acetate (250 mL) once. The organic phase was re-extracted with distilled water (150 mL×2) twice. All the aqueous phases were combined. The pH of the aqueous phase was adjusted with NaOH to 14. The resultant solution was extracted with dichloromethane (200 mL×1, 150 mL×6) seven times. The seven fractions of dichloromethane were combined, dried over anhydrous $MgSO_4$ for 30 min, filtered and concentrated. The resultant crude product was purified by column chromatography (developing solvent was $CHCl_3$: $CH_3OH=15:1$) to give the target compound.

Preparation 14

Di(2-(Dimethylamino)Ethyl)Amine

To a reaction flask were added t-butyl-di(2-(dimethylamino)ethyl)carbamate (3.000 g) and tetrahydrofuran (20 mL). The mixture was cooled in an ice bath. To the reaction flask was dropwise added concentrated hydrochloric acid (9.6 mL) (over 15 min). The mixture was stirred in an ice bath until the reaction was completed. After the reaction solution was concentrated to remove tetrahydrofuran, the resultant solution was washed with dichloromethane (50 mL) once. The organic phase was discarded. The pH of the aqueous phase was adjusted with $K_2CO_3$ to 10. The aqueous solution was extracted with dichloromethane (50 mL×4) four times. The four fractions of dichloromethane were combined, dried over anhydrous MgSO$_4$ for 30 min, filtered and concentrated to give the target compound.

Preparation 15

2-(2-(2-(2-T-Butoxyethoxy)Ethoxy)Ethoxy)Ethanol

To a reaction flask which was pre-protected with argon gas were added tetraethylene glycol (191.2 mL) and DIEA (300 mL). Dichloromethane (80 mL, dried via molecular sieves) was added to the reaction flask. The mixture was dissolved with stirring at the room temperature, and then cooled in an ice bath. Triphenylchloromethane (205.9 g) was dissolved in dichloromethane (400 mL, dried via molecular sieves) (over 4 hr). The resultant mixture was added to the reaction flask and reacted overnight. After the reaction was completed, the reaction solution was successively washed with 5% citric acid aqueous solution (500 mL×4) four times and with NaCl aqueous solution (250 mL×1) once, dried over anhydrous MgSO$_4$ for 30 min, filtered and concentrated to give the target compound.

Preparation 16

2-(2-(2-(2-T-Butoxyethoxy)Ethoxy)Ethoxy)Ethyl-4-Methylbenzenesulfonate

To a reaction flask were added 2-(2-(2-(2-t-butoxyethoxy)ethoxy)ethoxy)ethanol (347.5 g) and p-toluenesulfonyl chloride (227.7 g). Tetrahydrofuran (200 mL) was added to dissolve 2-(2-(2-(2-t-butoxyethoxy)ethoxy)ethoxy)ethanol and p-toluenesulfonyl chloride. To the reaction flask was added 20% sodium hydroxide aqueous solution (318.8 g) in an ice bath (over 2 hr). The mixture reacted overnight. After the reaction was completed, the reaction solution was concentrated to remove tetrahydrofuran. To the resultant crude product were added ethyl acetate (300 mL) and distilled water (50 mL). The solution was mixed homogeneously and stood to separate. The organic phase was washed with saturated NaCl aqueous solution (200 mL) once, dried over anhydrous MgSO$_4$ for 30 min, filtered and concentrated to give the target compound.

Preparation 17

2-(2-(2-(2-(2-T-Butoxyethoxy)Ethoxy)Ethoxy)Ethyl) Isoindol-1,3-Dione

To a reaction flask were added 2-(2-(2-(2-t-butoxyethoxy)ethoxy)ethoxy)ethyl 4-methylbenzenesulfonate (373.7 g) and potassium phthalimide (175.7 g). DMF (350 mL, dried over molecular sieves) was added to dissolve the mixture. The resultant solution was warmed and maintained at 65° C. in an oil bath until the reaction was completed (for about 8 hr). After the reaction solution was concentrated, ethyl acetate (250 mL) and distilled water (200 mL) were added. The resultant solution was mixed homogeneously and stood to separate. The organic phase was washed with saturated NaCl aqueous solution (150 mL) once, dried over anhydrous MgSO$_4$ for 30 min, filtered and concentrated to give a crude product. The crude product was re-crystallized from anhydrous ethanol to give the target compound.

Preparation 18

2-(2-(2-(2-T-Butoxyetoxy)Ethoxy)Ethoxy)Ethylamine

To a reaction flask was added 2-(2-(2-(2-(2-t-butoxyethoxy)ethoxy)ethoxy)ethyl)isoindol-1,3-dione (193.515 g). Tetrahydrofuran (350 mL) was added to dissolve 2-(2-(2-(2-(2-t-butoxyethoxy)ethoxy)ethoxy)ethyl)isoindol-1,3-dione. After 25% methylamine aqueous solution (127.410 g) was added, the resultant solution became clear by mechanically stirring at the room temperature. The mixture reacted overnight. After the reaction was stirred for 30 min in an oil bath at 40° C., the reaction solution was concentrated to give white solids. These solids were dissolved in ethyl acetate (300 mL) and distilled water (250 mL). The resultant was mixed homogeneously and stood to separate. The organic phase was washed with saturated NaCl aqueous solution (200 mL) once, dried over anhydrous MgSO$_4$ for 30 min, filtered and concentrated to give the target compound.

Preparation 19

2-(2-(2-(-Aminoethoxy)Ethoxy)Ethoxy)Ethanol Hydrochloride

To a reaction flask was added concentrated hydrochloric acid (100.5 mL). The flask was cooled in an ice bath. 2-(2-(2-(2-t-butoxyethoxy)ethoxy)ethoxy)ethylamine (123.7 g) was dissolved in tetrahydrofuran (170 mL) (over about 2 hr). The resultant mixture was dropwise added to the reaction flask and reacted overnight. After the reaction was completed, the reaction solution was concentrated to remove tetrahydrofuran. The resultant crude product was dissolved in chloroform (150 mL) and distilled water (100 mL). The resultant solution was mixed homogeneously and stood to separate. The aqueous phase was directly concentrated to give the target compound.

Preparation 20

T-Butyl-2-(2-(2-(2-Hydroxyethoxy)Ethoxy)Ethoxy) Ethylcarbamate

To a reaction flask was added 2-(2-(2-(-aminoethoxy)ethoxy)ethanol hydrochloride (41.6 g). Distilled water (80 mL) was added to dissolve 2-(2-(2-(-aminoethoxy)ethoxy)ethanol hydrochloride. The solution was cooled in an ice bath. Anhydrous sodium carbonate (38.414 g) was dissolved in distilled water (200 mL) (over 1 hr). The mixture was dropwise added to the reaction flask. Di-t-butyl dicarbonate (51.370 g) was dissolved in tetrahydrofuran (120 mL). The mixture was dropwise added (over 160 min) to the reaction flask. The resultant mixture reacted overnight. After the reaction was completed, the reaction solution was concentrated and then extracted with ethyl acetate (150 mL) once, extracted with dichloromethane (150 mL) once. Two organic phases were combined, dried over anhydrous MgSO$_4$ for 30 min, filtered and concentrated to give the target compound.

Preparation 21

T-Butyl-2-(2-(2-(2-(P-Methylphenoxy)Ethoxy) Ethoxy)Ethoxy)Ethyl Carbamate

To a reaction flask was added t-butyl-2-(2-(2-(2-hydroxyethoxy)ethoxy)ethoxy)ethylcarbamate (14.650 g). Tetrahydrofuran (75 mL) was added to dissolve t-butyl-2-(2-(2-(2-hydroxyethoxy)ethoxy)ethoxy)ethylcarbamate. To the reaction flask was added p-toluenesulfonyl chloride (11.439 g). The mixture was cooled in an ice bath. To the reaction flask was dropwise added 20% sodium hydroxide aqueous solution (18.684 g) (over 15 min). The ice bath was removed when the addition was completed. The resultant mixture was stirred at the room temperature until the reaction was completed (for about 5 hr). To the reaction flask was again added 20% sodium hydroxide aqueous solution (8.715 g). The mixture was stirred for 2 hr in an oil bath at 40° C. The resultant solution was directly used in the subsequent reaction.

Preparation 22

T-Butyl-2-(2-(2-(2-(Dimethylamino)Ethoxy)Ethoxy)Ethoxy)Ethylcarbamate

To a reaction flask was added dimethylamine hydrochloride (40.766 g). Distilled water (60 mL) was added to dissolve dimethylamine hydrochloride. The solution was cooled in an ice bath. To the reaction flask was added 20% sodium hydroxide aqueous solution (101.464 g). To the reaction flask was added the solution obtained in Preparation 22. The mixture was stirred in an oil bath at 40° C. until the reaction was completed. After the reaction solution was concentrated to remove tetrahydrofuran, dichloromethane (200 mL) was added. The mixture was mixed homogeneously and stood to separate. The aqueous phase was discarded. The organic phase was added into distilled water (100 mL). The pH of the mixture was adjusted with 2 N HCl to 3. The solution was mixed homogeneously and stood to separate. The aqueous phase was directly concentrated to give the target compound.

Preparation 23

2-(2-(2-(2-(Dimethylamino)Ethoxy)Ethoxy)Ethoxy)Ethylamine Hydrochloride

To a reaction flask was added t-butyl-2-(2-(2-(2-(dimethylamino)ethoxy)ethoxy)ethoxy)ethylcarbamate (8.629 g). Tetrahydrofuran was added to dissolve t-butyl-2-(2-(2-(2-(dimethylamino)ethoxy)ethoxy)ethoxy)ethylcarbamate. The resultant solution was cooled in an ice bath. To the reaction flask was added concentrated hydrochloric acid (20 mL) (over 20 min). After the reaction was completed, the reaction solution was concentrated to remove tetrahydrofuran, and distilled water (50 mL) and dichloromethane (50 mL) were added. The resultant mixture was mixed homogeneously and stood to separate. The aqueous phase was directly concentrated to give the target compound.

The target compounds in Preparation 24 to 104 were prepared according to the preparation process in Preparation 4.

Preparation 24

4-(4-(Methylsulfonyl)Amino)-4-Oxobutanoic Acid

Preparation 25

4-(4-(Phenyllsulfonyl)Amino)-4-Oxobutanoic Acid

Preparation 26

4-(4-(Morpholinylmethyl)Phenylamino)-4-Oxobutanoic Acid

Preparation 27

4-(4-((Dimethylamino)Methyl)Phenylamino)-4-Oxobutanoic Acid

Preparation 28

5-(4-((Dimethylamino)Methyl)Phenylamino)-5-Oxopentanoic Acid

Preparation 29

4-(2-(2-(Dimethylamino)Ethoxy)Ethylamino)-4-Oxobutanoic Acid

Preparation 30

5-(2-(2-(Dimethylamino)Ethoxy)Ethylamino)-5-Oxopentanoic Acid

Preparation 31

4-(4-(Hydroxyethyl)Piperazin-1-yl)-4-Oxobutanoic Acid

Preparation 32

5-(4-(Hydroxyethyl)Piperazin-1-yl)-5-Oxopentanoic Acid

Preparation 33

4-((Morpholin-1-yl)Amino)-4-Oxobutanoic Acid

Preparation 34

5-((Morpholin-1-yl)Amino)-5-Oxopentanoic Acid

Preparation 35

4-(3-(Morpholin-1-yl)Propylamino)-4-Oxobutanoic Acid

Preparation 36

5-(3-(Morpholin-1-yl)Propylamino)-5-Oxopentanoic Acid

Preparation 37

4-((4-Methylpiperazin-1-yl)Amino)-4-Oxobutanoic Acid

Preparation 38

5-((4-Methylpiperazin-1-yl)Amino)-5-Oxopentanoic Acid

Preparation 39

4-(2-(Tetrahydropyrrol-1-yl)Ethylamino)-4-Oxobutanoic Acid

Preparation 40

5-(2-(Tetrahydropyrrol-1-yl)Ethylamino)-5-Oxopentanoic Acid

Preparation 41

4-(3-(Tetrahydropyrrol-1-yl)Propylamino)-4-Oxobutanoic Acid

Preparation 42

5-(3-(Tetrahydropyrrol-1-yl)Propylamino)-5-Oxopentanoic Acid

Preparation 43

4-((6-(Morpholin-1-yl)Pyridin-3-yl)Amino)-4-Oxobutanoic Acid

Preparation 44

5-((6-(Morpholin-1-yl)Pyridin-3-yl)Amino)-5-Oxopentanoic Acid

Preparation 45

4-((Pyridin-4-yl)Amino)-4-Oxobutanoic Acid

Preparation 46

5-((Pyridin-4-yl)Amino)-5-Oxopentanoic Acid

Preparation 47

4-((Pyridin-3-yl)Amino)-4-Oxobutanoic Acid

Preparation 48

4-((Pyridin-3-yl)Amino)-4-Oxopentanoic Acid

Preparation 49

4-((Pyridin-4-yl)Methylamino)-4-Oxobutanoic Acid

Preparation 50

5-((Pyridin-4-yl)Methylamino)-5-Oxopentanoic Acid

Preparation 51

4-((Pyridin-3-yl)Methylamino)-4-Oxobutanoic Acid

Preparation 52

5-((Pyridin-3-yl)Methylamino)-5-Oxopentanoic Acid

Preparation 53

4-((Pyridin-2-yl)Methylamino)-4-Oxobutanoic Acid

Preparation 54

5-((Pyridin-2-yl)Methylamino)-5-Oxopentanoic Acid

Preparation 55

4-(2-(Pyridin-4-yl)Ethylamino)-4-Oxobutanoic Acid

Preparation 56

5-(2-(Pyridin-4-yl)Ethylamino)-5-Oxopentanoic Acid

Preparation 57

4-(2-(Pyridin-2-yl)Ethylamino)-4-Oxobutanoic Acid

Preparation 58

5-(2-(Pyridin-2-yl)Ethylamino)-5-Oxopentanoic Acid

Preparation 59

4-(2-(Pyridin-3-yl)Ethylamino)-4-Oxobutanoic Acid

Preparation 60

5-(2-(Pyridin-3-yl)Ethylamino)-5-Oxopentanoic Acid

Preparation 61

4-(2-(4-(Aminosulfonyl)Phenyl)Ethylamino)-4-Oxobutanoic Acid

Preparation 62

5-(2-(4-(Aminosulfonyl)Phenyl)Ethylamino)-5-Oxopentanoic Acid

Preparation 63

4-(4-Ethylpiperazin-1-yl)-4-Oxobutanoic Acid

Preparation 64

5-(4-Ethylpiperazin-1-yl)-5-Oxopentanoic Acid

Preparation 65

4-(Purineamino)-4-Oxobutanoic Acid

Preparation 66

5-(Purineamino)-5-Oxopentanoic Acid

Preparation 67

4-(4-(3-(Dimethylamino)Propyl)Piperazin-1-yl)-4-Oxobutanoic Acid

Preparation 68

5-(4-(3-(Dimethylamino)Propyl)Piperazin-1-yl)-5-Oxopentanoic Acid

Preparation 69

4-(3-(4-Methylpiperazin-1-yl)Propylamino)-4-Oxobutanoic Acid

Preparation 70

5-(3-(4-Methylpiperazin-1-yl)Propylamino)-5-Oxopentanoic Acid

Preparation 71

4-(2-(Dimethylamino)Ethylamino)-4-Oxobutanoic Acid

Preparation 72

5-(2-(Dimethylamino)Ethylamino)-5-Oxopentanoic Acid

Preparation 73

4-(Di(2-(Dimethylamino)Ethyl)Amino)-4-Oxobutanoic Acid

Preparation 74

5-(Di(2-(Dimethylamino)Ethyl)Amino)-5-Oxopentanoic Acid

Preparation 75

4-(2-(2-(2-(2-(Dimethylamino)Ethoxy)Ethoxy)Ethoxy)Ethylamino)-4-Oxobutanoic Acid

Preparation 76

5-(2-(2-(2-(2-(Dimethylamino)Ethoxy)Ethoxy)Ethoxy)Ethylamino)-5-Oxopentanoic Acid

Preparation 77

4-((Pyrazin-2-yl)Amino)-4-Oxobutanoic Acid

Preparation 78

5-((Pyrazin-2-yl)Amino)-5-Oxopentanoic Acid

Preparation 79

4-((Pyridin-2-yl)Amino)-4-Oxobutanoic Acid

Preparation 80

5-((Pyridin-2-yl)Amino)-5-Oxopentanoic Acid

Preparation 81

4-((Pyrimidin2-yl)Amino)-4-Oxobutanoic Acid

Preparation 82

5-((Pyrimidin2-yl)Amino)-5-Oxopentanoic Acid

Preparation 83

4-(2-Hydroxyethylamino)-4-Oxobutanoic Acid

Preparation 84

5-(2-Hydroxyethylamino)-5-Oxopentanoic Acid

Preparation 85

4-(2-(2-Hydroxyethoxy)Ethylamino)-4-Oxobutanoic Acid

Preparation 86

5-(2-(2-Hydroxyethoxy)Ethylamino)-5-Oxopentanoic Acid

Preparation 87

4-(Di(2-(Hydroxy)Ethyl)Amino)-4-Oxobutanoic Acid

Preparation 88

5-(Di(2-(Hydroxy)Ethyl)Amino)-5-Oxopentanoic Acid

Preparation 89

4-Amino-4-Oxobutanoic Acid

Preparation 90

5-Amino-5-Oxopentanoic Acid

Preparation 91

4-Methylamino-4-Oxobutanoic Acid

Preparation 92

5-Methylamino-5-Oxopentanoic Acid

Preparation 93

4-Dimethylamino-4-Oxobutanoic Acid

Preparation 94

5-Dimethylamino-5-Oxopentanoic Acid

Preparation 95

4-(Morpholin-1-yl)-4-Oxobutanoic Acid

Preparation 96

5-(Morpholin-1-yl)-5-Oxopentanoic Acid

Preparation 97

4-(Piperidin-1-yl)-4-Oxobutanoic Acid

Preparation 98

4-(Tetrahydropyrrol-1-yl)-4-Oxobutanoic Acid

Preparation 99

4-(2-(Morpholin-1-yl)Ethylamino)-4-Oxobutanoic Acid

Preparation 100

4-(2-(2-(2-(2-(2-(2-(2-(2-Hydroxyethoxy)Ethoxy)Ethoxy)Ethoxy)Ethoxy)Ethoxy)Ethoxy)Ethylamino)-4-Oxobutanoic Acid

Preparation 101

4-(2-(2-(2-(2-(2-(2-(2-(2-(2-Hydroxyethoxy)Ethoxy)Ethoxy)Ethoxy)Ethoxy)Ethoxy)Ethoxy)Ethoxy)Ethylamino)-4-Oxobutanoic Acid

Preparation 102

4-(2-(2-(2-(2-(2-(2-(2-(2-(2-(2-(2-Hydroxyethoxy)Ethoxy)Ethoxy)Ethoxy)Ethoxy)Ethoxy)Ethoxy)Ethoxy)Ethoxy)Ethoxy)Ethoxy)Ethylamino)-4-Oxobutanoic Acid

Preparation 103

4-(2-(2-(2-(2-(2-(2-(2-(2-(2-(Methoxy)Ethoxy)Ethoxy)Ethoxy)Ethoxy)Ethoxy)Ethoxy)Ethoxy)Ethoxy)Ethylamino)-4-Oxobutanoic Acid

Preparation 104

4-(2-(2-(2-(2-Hydroxyethoxy)Ethoxy)Ethoxy)Ethylamino)-4-Oxobutanoic Acid

Example 1

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-(2-(2-(2-(2-Hydr Oxy-ethoxy)Ethoxy)Ethoxy)Ethylamino)-4-Oxo-Butyrato)-1-Methoxy-5,12-Naphthalenedione To a reaction flask was added the compound (99 mg) obtained in Preparation 1. Dichloromethane (5 mL, dried via molecular sieves) was added to dissolve the compound. To the resultant solution were added the compound (82 mg) obtained in Preparation 104 and DMAP (8 mg). The mixture was stirred under the protection of argon gas. EDC-HCl (50 mg) was added. The mixture reacted overnight at the room temperature. After the reaction was completed, the reaction solution was concentrated and then directly purified by thin layer chromatography (the developing solvent was chloroform ($CHCl_3$): methanol ($CH_3OH$)=95:5, 5 mL, adding one drop of glacial acetic acid), to give the target compound. MS: 867.1 (M-1)

The compounds listed in Table 1 were prepared according to the preparation process in Example 1, in which the dashed line in the substituents represented the linking bond.

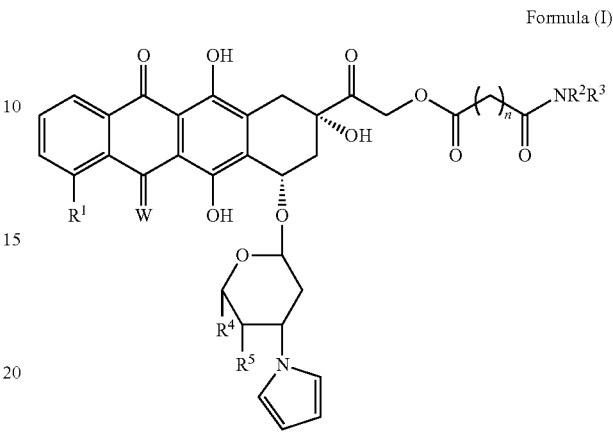

Formula (I)

TABLE 1

| Examples | n | $NR^2R^3$ | Mass Spectra (MS) |
|---|---|---|---|
| 2 | 2 | ----NH-C6H4-CH2-N(morpholine) | MS: 868.1 (M + 1) |
| 3 | 3 | ----NH-C6H4-CH2-N(morpholine) | MS: 882.3 (M + 1) |
| 4 | 2 | ----NH-C6H4-CH2-N(CH3)2 | $MS^+$ 825.9 |
| 5 | 3 | ----NH-C6H4-CH2-N(CH3)2 | MS: 840.3 (M + 1) |
| 6 | 2 | ----NH-CH2CH2-O-CH2CH2-N(CH3)2 | $MS^-$ 806.2 (M − 1)<br>$MS^+$ 808.3 (M + 1)) |
| 7 | 3 | ----NH-CH2CH2-O-CH2CH2-N(CH3)2 | $MS^+$ 822.3 (M + 1) |
| 8 | 2 | ----N(piperazine)-CH2CH2-OH | $MS^+$ 806.1 (M + 1) |

TABLE 1-continued

| Examples | n | NR²R³ | Mass Spectra (MS) |
|---|---|---|---|
| 9 | 3 | —N(piperazine)N-CH₂CH₂OH | MS⁺ 820.1 (M + 1) |
| 10 | 2 | —NH—N(morpholine) | MS⁻: 775.8 (M − 1) |
| 11 | 3 | —NH—N(morpholine) | MS⁺: 791.2 (M + 1) |
| 12 | 2 | —NH—CH₂CH₂CH₂—N(morpholine) | MS⁺: 820.4 (M + 1)<br>MS⁻: 818.6 (M − 1) |
| 13 | 3 | —NH—CH₂CH₂CH₂—N(morpholine) | MS⁺: 834.8 (M + 1) |
| 14 | 2 | —NH—N(4-methylpiperazine) | MS⁻: 788.9 (M − 1) |
| 15 | 3 | —NH—N(4-methylpiperazine) | MS⁺: 805.8 (M + 1) |
| 16 | 2 | —NH—CH₂CH₂—N(pyrrolidine) | MS⁺ 790.3 (M + 1) |
| 17 | 3 | —NH—CH₂CH₂—N(pyrrolidine) | MS⁺ 804.4 (M + 1) |
| 18 | 2 | —NH—CH₂CH₂CH₂—N(pyrrolidine) | MS⁺: 804.1 (M + 1) |
| 19 | 3 | —NH—CH₂CH₂CH₂—N(pyrrolidine) | MS⁺: 817.2 (M + 1) |
| 20 | 2 | —NH-(5-pyridyl-2-morpholine) | MS⁻: 853.3 (M − 1)<br>MS⁺: 855.4 (M + 1) |
| 21 | 3 | —NH-(5-pyridyl-2-morpholine) | MS⁺: 869.3 (M + 1) |
| 22 | 2 | —NH-(4-pyridyl) | MS⁺: 770.0 (M + 1)<br>MS⁻: 767.7 (M − 1) |
| 23 | 3 | —NH-(4-pyridyl) | MS⁺: 784.7 (M + 1) |

TABLE 1-continued

| Examples | n | NR²R³ | Mass Spectra (MS) |
|---|---|---|---|
| 24 | 2 | pyridin-3-ylamino | MS⁺: 770.1 (M + 1) |
| 25 | 3 | pyridin-3-ylamino | MS⁺: 784.6 (M + 1) |
| 26 | 2 | (pyridin-4-ylmethyl)amino | MS⁺: 784.0 (M + 1) |
| 27 | 3 | (pyridin-4-ylmethyl)amino | MS⁺: 798.2 (M + 1) |
| 28 | 2 | (pyridin-3-ylmethyl)amino | MS⁺: 783.9 (M + 1)<br>MS⁻: 781.8 (M − 1) |
| 29 | 3 | (pyridin-3-ylmethyl)amino | MS⁺: 798.9 (M + 1) |
| 30 | 2 | (pyridin-2-ylmethyl)amino | MS⁺: 784.1 (M + 1) |
| 31 | 3 | (pyridin-2-ylmethyl)amino | MS⁺: 798.1 (M + 1) |
| 32 | 2 | (2-(pyridin-4-yl)ethyl)amino | MS⁺: 798.0 (M + 1) |
| 33 | 3 | (2-(pyridin-4-yl)ethyl)amino | MS⁺: 812.1 (M + 1) |
| 34 | 2 | (2-(pyridin-2-yl)ethyl)amino | MS⁺: 798.0 (M + 1) |
| 35 | 3 | (2-(pyridin-2-yl)ethyl)amino | MS⁺: 812.3 (M + 1) |
| 36 | 2 | (2-(pyridin-3-yl)ethyl)amino | MS⁺: 798.0 (M + 1) |
| 37 | 3 | (2-(pyridin-3-yl)ethyl)amino | MS⁺: 812.1 (M + 1) |

TABLE 1-continued
| Examples | n | NR²R³ | Mass Spectra (MS) |
|---|---|---|---|
| 38 | 2 | 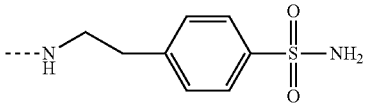 | MS⁻: 873.7 (M − 1) |
| 39 | 3 | 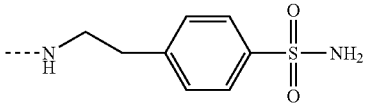 | MS⁻: 888.1 (M − 1) |
| 40 | 2 | 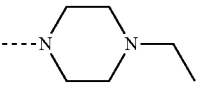 | MS⁺: 790.1 (M + 1) |
| 41 | 3 | 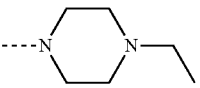 | MS⁺: 804.3 (M + 1) |
| 42 | 2 | 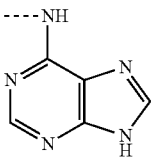 | MS⁺: 811.0 (M + 1)<br>MS⁻: 809.2 (M − 1) |
| 43 | 3 | 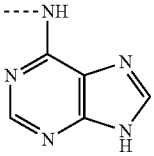 | MS⁺: 825.4 (M + 1) |
| 44 | 2 | 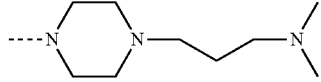 | MS⁺: 847.1 (M + 1)<br>MS⁻: 845.0 (M − 1) |
| 45 | 3 | 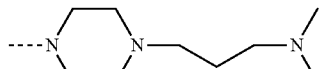 | MS⁺: 860.3 (M + 1) |
| 46 | 2 | 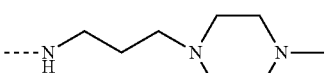 | MS⁺: 833.1 (M + 1) |
| 47 | 3 | 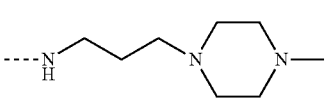 | MS⁺: 847.2 (M + 1) |
| 48 | 2 | 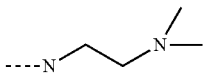 | MS⁺: 764.1 (M + 1) |
| 49 | 3 | 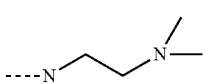 | MS⁺: 778.1 (M + 1) |

TABLE 1-continued

| Examples | n | NR²R³ | Mass Spectra (MS) |
|---|---|---|---|
| 50 | 2 | -N(CH₂CH₂N(CH₃)₂)₂ | MS⁺: 835.2 (M + 1) |
| 51 | 3 | -N(CH₂CH₂N(CH₃)₂)₂ | MS⁺: 849.2 (M + 1) |
| 52 | 2 | -NH-CH₂CH₂-O-CH₂CH₂-O-CH₂CH₂-O-CH₂CH₂-N(CH₃)₂ | MS⁺ 896.1 (M + 1) |
| 53 | 3 | -NH-CH₂CH₂-O-CH₂CH₂-O-CH₂CH₂-O-CH₂CH₂-N(CH₃)₂ | MS⁺ 909.8 (M + 1) |
| 54 | 2 | -NH-(2-pyrazinyl) | MS⁺ 771.2 (M + 1) |
| 55 | 3 | -NH-(2-pyrazinyl) | MS⁺ 784.1 (M + 1) |
| 56 | 2 | -NH-(2-pyridyl) | MS⁺ 770.1 (M + 1) |
| 57 | 3 | -NH-(2-pyridyl) | MS⁺ 784.1 (M + 1) |
| 58 | 2 | -HN-(2-pyrimidinyl) | MS⁺ 770.1 (M + 1) |
| 59 | 3 | -HN-(2-pyrimidinyl) | MS⁺ 784.1 (M + 1) |
| 60 | 2 | -NH-CH₂CH₂CH₂-OH | MS⁻: 735.2 (M − 1)<br>MS⁺: 759.3 (M + Na⁺) |
| 61 | 3 | -NH-CH₂CH₂CH₂-OH | MS⁻: 750.7 (M − 1) |
| 62 | 2 | -NH-CH₂CH₂CH₂-O-CH₂CH₂-OH | MS⁺: 803.3 (M + Na⁺) |
| 63 | 3 | -NH-CH₂CH₂CH₂-O-CH₂CH₂-OH | MS⁻: 793.6 (M − 1) |

TABLE 1-continued

| Examples | n | NR²R³ | Mass Spectra (MS) |
|---|---|---|---|
| 64 | 2 | ----N(CH₂CH₂OH)₂ | MS⁺: 803.2 (M + Na⁺)<br>MS⁻: 799.2 (M − 1) |
| 65 | 3 | ----N(CH₂CH₂OH)₂ | MS⁺: 795.2 (M + 1) |
| 66 | 2 | NH₂ | MS⁺: 693.1 (M + 1) |
| 67 | 3 | NH₂ | MS⁺: 707.2 (M + 1) |
| 68 | 2 | NHCH₃ | MS⁻: 705.6 (M − 1) |
| 69 | 3 | NHCH₃ | MS⁺: 721.1 (M + 1) |
| 70 | 2 | N(CH₃)₂ | MS⁺: 721.1 (M + 1) |
| 71 | 3 | N(CH₃)₂ | MS⁺: 735.6 (M + 1) |
| 72 | 2 | morpholinyl | MS⁺: 763.2 (M + 1) |
| 73 | 3 | morpholinyl | MS⁺: 777.1 (M + 1) |
| 74 | 2 | piperidinyl | MS⁺: 761.3 (M + 1) |
| 75 | 2 | pyrrolidinyl | MS⁺: 746.9 (M + 1) |
| 88 | 2 | ----NH-CH₂CH₂-morpholinyl | MS⁺: 806.2 (M + 1) |
| 90 | 2 | ----NH-(CH₂CH₂O)₇-CH₂CH₂OH | |
| 91 | 2 | ----NH-(CH₂CH₂O)₈-CH₂CH₂OH | |
| 92 | 2 | ----NH-(CH₂CH₂O)₁₁-CH₂CH₂OH | |
| 93 | 2 | ----NH-(CH₂CH₂O)₈-CH₂CH₂-O-CH₃ | |
| 94 | 2 | ----NH-S(O)₂-CH₃ | MS⁺: 771 (M + 1) |
| 95 | 2 | ----NH-S(O)₂-C₆H₅ | MS⁺: 833 (M + 1) |

TABLE 1-continued

| Examples | n | NR²R³ | Mass Spectra (MS) |
|---|---|---|---|
| 97 | 3 | ----NH-CH₂CH₂-N(morpholine) | |
| 98 | 2 | ----NH-CH₂CH₂-(O-CH₂CH₂)₈-OCH₃ | |

The ¹H-NMR spectra data of the compound in Example 28 were:

δ=1.145 ppm (d, 3H), δ=1.664 ppm (m, 1H), δ=2.110 ppm (m, 1H),

δ=2.336 ppm (d, 1H), δ=2.415 ppm (m, 1H), δ=2.505 ppm (m, 2H),

δ=2.675 ppm (t, 2H), δ=2.917 ppm (d, 1H), δ=3.008 ppm (d, 1H),

δ=3.546 ppm (s, 1H), δ=3.943 ppm (s, 4H), δ=4.303 ppm (m, 5H),

δ=4.982 ppm (s, 1H), δ=5.189 ppm (d, 1H), δ=5.253 ppm (d, 1H),

δ=5.349 ppm (s, 1H), δ=5.920 ppm (s, 2H), δ=6.780 ppm (s, 2H),

δ=7.346 ppm (m, 1H), δ=7.609 ppm (d, 1H), δ=7.640 ppm (d, 1H),

δ=7.856 ppm (m, 2H), δ=8.471 ppm (m, 3H), δ=13.219 ppm (s, 1H),

δ=13.982 ppm (s, 1H)

The ¹H-NMR spectra data of the compound in Example 88 were:

δ=1.149 ppm (d, 3H), δ=2.646 ppm (d, 2H), δ=2.409 ppm (t, 2H),

δ=1.375-2.445 ppm (m, 2H), δ=2.795-2.936 ppm (dd, 2H),

δ=2.702 ppm (s, 4H), δ=4.294 ppm (m, 1H), δ=3.869 ppm (s, 3H),

δ=2.632 ppm (d, 2H), δ=3.666 ppm (t, 4H),

δ=5.162-5.236 ppm (dd, 2H), δ=4.282 ppm (m, 1H),

δ=4.897 ppm (s, 1H), δ=3.533 ppm (s, 1H), δ=5.314 ppm (s, 1H),

δ=5.899 ppm (t, 2H), δ=7.729 ppm (d, 1H), δ=6.755 ppm (t, 2H),

δ=7.492 ppm (d, 1H), δ=7.772 ppm (t, 1H), δ=8.070 ppm (t, 1H),

δ=13.097 ppm (bs, 1H), δ=13.871 ppm (s, 1H)

Example 76

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-(2-(2-(Dimethylamino)Ethoxy)Ethylamino)-4-Oxo-Butyrato)-1-Methoxy-5,12-Naphthalenedione Acetate The target compound (10 mg) obtained in Example 6 was dissolved in chloroform (10 mL) with stirring. To a reaction flask was added glacial acetic acid (1 mg) dissolved in chloroform (10 mL). The mixture was continuously stirred for 10 min, and rotary-evaporated to remove the solvent, thereby giving the target compound.

The solubility of the compound in water was more than 9 mg/mL.

The target compounds in Examples 77-87 and 89 were prepared according to the preparation process in Example 76.

Example 77

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((4-(2-Hydroxy)Ethyl)Piperazin-1-yl)-4-Oxo-Butyrato)-1-Methoxy-5,12-Naphthalenedione Acetate The Solubility of the Compound in Water was More than 10.6 mg/ml.

Example 78

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((3-(Morpholin-1-yl)Propyl)Amino)-4-Oxo-Butyrato)-1-Methoxy-5,12-Naphthalenedione Acetate The solubility of the compound in water was more than 22 mg/ml.

Example 79

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((4-Methyl)Piperazin-1-yl)Amino)-4-Oxo-Butyrato)-1-Methoxy-5,12-Naphthalenedione Acetate The solubility of the compound in water was more than 5 mg/ml.

Example 80

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-(4-Ethylpiperazin-1-yl)-4-Oxo-Butyrato)-1-Methoxy-5,12-Naphthalenedione Acetate The solubility of the compound in water was more than 11 mg/ml.

Example 81

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((3-(4-Methylpiperazin-1-yl)Propyl)Amino)-4-Oxo-Butyrato)-1-Methoxy-5,12-Naphthalenedione Acetate The solubility of the compound in water was more than 7 mg/ml.

Example 82

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((Pyridin-4-yl)Methyl)Amino)-4-Oxo-Butyrato)-1-Methoxy-5,12-Naphthalenedione Acetate The solubility of the compound in water was more than 6 mg/ml.

Example 83

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((Pyridin-3-yl)Methyl)Amino)-4-Oxo-Butyrato)-1-Methoxy-5,12-Naphthalenedione Acetate The solubility of the compound in water was more than 1 mg/ml.

Example 84

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-(2-(Pyridin-2-yl)Ethyl)Amino)-4-Oxo-Butyrato)-1-Methoxy-5,12-Naphthalenedione Acetate The solubility of the compound in water was more than 12 mg/ml.

Example 85

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-(2-(Pyridin-3-yl)Ethyl)Amino)-4-Oxo-Butyrato)-1-Methoxy-5,12-Naphthalenedione Acetate The solubility of the compound in water was more than 11 mg/ml.

Example 86

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-(2-(Pyridin-4-yl)Ethyl)Amino)-4-Oxo-Butyrato)-1-Methoxy-5,12-Naphthalenedione Acetate The solubility of the compound in water was more than 3 mg/ml.

Example 87

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-(4-(3-(Dimethylamino)Propyl)Piperazin-1-yl)-4-Oxo-Butyrato)-1-Methoxy-5,12-Naphthalenedione Acetate The solubility of the compound in water was more than 16 mg/ml.

Example 89

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((2-(Morpholin-1-yl)Ethyl)Amino)-4-Oxo-Butyrato)-1-Methoxy-5,12-Naphthalenedione Acetate

Example 96

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((2-(Morpholin-1-yl)Ethyl)Amino)-4-Oxo-Butyrato)-1-Methoxy-5,12-Naphthalenedione Phosphate The solubility of the compound in water was more than 26 mg/ml.

The compound in Example 96 was detected by HPLC after being sealed and stored for 9 months under refrigeration conditions. No obvious degraded product was observed, which indicates good stability of the compound.

Example 99

10-((3'-(Pyrrol-1-yl)-2',3',6'-Trideoxy-Alpha-L-Lyxo-Hexylpyranyl)Oxy)-7,8,9,10-Tetrahydro-6,8,11-Trihydroxy-13-Oxo-14-(4-((2-(Morpholin-1-yl)Ethyl)Amino)-4-Oxo-Butyrato)-1-Methoxy-5,12-Naphthalenedione Hydrochloride

BIOLOGICAL ACTIVITY EXAMPLES

Example 1: SK-OV-3 Cell Growth Inhibition Test (MTT Assay)

I. Assay Materials
Cell strains: SK-OV-3 (human ovarian cancer cell strains); MTT; antitumor compounds; DMSO.
II. Reagents and Consumable Materials
Culture medium: 90% McCoy's 5A+10% FBS; Pancreatin (0.25% (w/v) solution was formulated with PBS, 0.53 mM of EDTA was added in the formulation); PBS; 96-well culture plate.
III. Assay Process
1. A plate (10 cm) of cells in logarithmic growth phase that were normally cultured was collected;
2. The culture solution was sucked out. The plate was washed with 5 mL of PBS once or twice;
3. PBS was sucked out. 1.5 mL of 0.25% pancreatin was added to infiltrate the cells;
4. The pancreatin was sucked out. The culture plate was placed in an incubator. Digestion was carried out for about 5 min at 37° C.;
5. 4.5 mL of complete culture solution was added to the culture plate to stop the digestion. The cells were carefully scoured with micropipette (1 ml) to give a uniform cell suspension. The suspension was implanted into a 96-well cell culture disc by 4000 cells/100 µL per well. The culture plate was incubated overnight under 5% $CO_2$ at 37° C. In day 2, 100 µL of culture solution comprising a compound was added in each well. The plate was further incubated for 69 h under 5% $CO_2$ at 37° C.;

6. The culture solution was sucked out;

7. 100 µL of serum-free culture solution containing 0.5 mg/mL MTT was added in each well. The plate was incubated for 3 h;

8. The culture solution was carefully sucked out;

9. 100 µL of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 2

Growth Inhibition Activity at 667 nM of Some Compounds in Examples on SK-OV-3 Cells

| Compounds | Inhibition Ratio (%) | Compounds | Inhibition Ratio (%) | Compounds | Inhibition Ratio (%) |
|---|---|---|---|---|---|
| Example 1 | 57.3 | Example 3 | 62.5 | Example 8 | 60 |
| Example 10 | 71.5 | Example 12 | 48.8 | Example 14 | 53.6 |
| Example 18 | 47.4 | Example 20 | 62.6 | Example 22 | 60.3 |
| Example 24 | 61.4 | Example 26 | 67.6 | Example 28 | 66.2 |
| Example 30 | 59.9 | Example 32 | 59.7 | Example 34 | 59.4 |
| Example 35 | 57.8 | Example 38 | 67.6 | Example 40 | 47.9 |
| Example 44 | 52.3 | Example 60 | 58.9 | Example 62 | 63.6 |
| Example 64 | 65.9 | Example 66 | 66.5 | Example 76 | 46.4 |
| Example 77 | 60.4 | Example 81 | 56.4 | Example 94 | 71.4 |
| Example 95 | 66.3 | | | | |

Example 2: BxPc-3 Cell Growth Inhibition Test (MTT Assay)

I. Assay Materials:

Cell strains: BxPC-3 (human pancreatic cancer cell strains); MTT; antitumor compounds; DMSO.

II. Reagents and Consumable Materials

Culture medium: 90% RPMI-1640+10% FBS; Pancreatin (0.25% (w/v) solution was formulated with PBS, 0.53 mM of EDTA was added in the formulation); PBS; 96-well culture plate.

III. Assay Process:

1. A plate (10 cm) of cells in logarithmic growth phase that were normally cultured was collected;

2. The culture solution was sucked out. The plate was washed with 5 mL of PBS once or twice;

3. PBS was sucked out. 1.5 mL of 0.25% pancreatin was added to infiltrate the cells;

4. The culture plate was placed in an incubator. Digestion was carried out for about 8 min at 37° C.;

5. 4.5 mL of complete culture solution was added to the culture plate to stop the digestion. The cells were carefully scoured with micropipette (1 ml) to give a uniform cell suspension. The suspension was implanted into a 96-well cell culture disc by 5000 cells/100 µL per well. The culture plate was incubated overnight under 5% $CO_2$ at 37° C. In day 2, 100 µL of culture solution comprising a compound was added in each well. The plate was further incubated for 70 h under 5% $CO_2$ at 37° C.;

6. The culture solution was sucked out;

7. 100 µL of serum-free culture solution containing 0.5 mg/mL MTT was added in each well. The plate was incubated for 3 h;

8. The culture solution was carefully sucked out;

9. 100 µL of DMSO was added into each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 3

Growth Inhibition Activity at 2000 nM of Some Compounds in Examples on BxPc-3 Cells

| Compounds | Inhibition Ratio (%) | Compounds | Inhibition Ratio (%) | Compounds | Inhibition Ratio (%) |
|---|---|---|---|---|---|
| Example 1 | 82.5 | Example 3 | 81.2 | Example 8 | 82.6 |
| Example 10 | 85 | Example 12 | 74.9 | Example 14 | 81.8 |
| Example 18 | 70.7 | Example 20 | 84.1 | Example 22 | 82 |
| Example 24 | 84.7 | Example 26 | 82.7 | Example 28 | 84.7 |
| Example 30 | 85.2 | Example 32 | 83.4 | Example 34 | 84 |
| Example 35 | 81.3 | Example 38 | 82.4 | Example 40 | 76.5 |
| Example 44 | 78.5 | Example 60 | 83.4 | Example 62 | 82.5 |
| Example 64 | 83.7 | Example 66 | 83.1 | Example 76 | 77.1 |
| Example 77 | 83.3 | Example 81 | 80.7 | Example 94 | 84.9 |
| Example 95 | 80.6 | | | | |

Example 3: NCI-H446 Cell Growth Inhibition Test (MTT Assay)

I. Assay Materials

Cell strains: NCI-H446 (human small cell lung cancer cell strains); MTT; antitumor compounds; DMSO.

II. Reagents and Consumable Materials

Culture medium: 90% RPMI-1640+10% FBS; Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. PBS was sucked out. 1.5 mL of 0.25% pancreatin was added to infiltrate the cells;

4. The culture plate was placed in an incubator. Digestion was carried out for about 3 min at 37° C.;

5. 3 mL of complete culture solution was added to the culture plate to stop the digestion. The cells were carefully scoured with micropipette (1 ml) to give a uniform cell suspension. The suspension was implanted into a 96-well cell culture disc by 4000 cells/100 µL per well. The culture plate was incubated overnight under 5% $CO_2$ at 37° C. In day 2, 100 µL of culture solution comprising a compound was added in each well. The plate was further incubated for 70 h under 5% $CO_2$ at 37° C.;

6. The culture solution was sucked out;

7. 100 µL of serum-free culture solution containing 0.5 mg/mL MTT was added in each well. The plate was incubated for 3 h;

8. The culture solution was carefully sucked out;

9. 100 µL of DMSO was added into each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 4

Growth Inhibition Activity at 222 nM of Some Compounds in Examples on NCI-H446 Cells

| Compounds | Inhibition Ratio (%) | Compounds | Inhibition Ratio (%) | Compounds | Inhibition Ratio (%) |
|---|---|---|---|---|---|
| Example 1 | 43.2 | Example 3 | 60.8 | Example 8 | 59.5 |
| Example 10 | 61.1 | Example 12 | 54.6 | Example 20 | 68 |
| Example 22 | 62.1 | Example 24 | 61.8 | Example 26 | 66.9 |
| Example 28 | 65.8 | Example 30 | 61 | Example 32 | 59.3 |
| Example 34 | 60.7 | Example 35 | 57.2 | Example 38 | 62.6 |
| Example 40 | 49 | Example 44 | 46.3 | Example 60 | 52.5 |
| Example 62 | 64.6 | Example 64 | 51.6 | Example 66 | 56.2 |
| Example 76 | 46 | Example 77 | 59.1 | Example 81 | 56.8 |
| Example 94 | 48.4 | | | | |

Example 4: MDA-MB-453 Cell Growth Inhibition Test (SRB Assay)

I. Assay Materials

Cell strains: MDA-MB-453 (human breast cancer cell strains); SRB: 0.4% (w/v) working solution was formulated with 1% glacial acetic acid, reserved at 4° C.; antitumor compounds; DMSO.

II. Reagents and Consumable Materials

Culture medium: 90% L15+10% FBS; pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. 1.5 mL of 0.25% pancreatin was added to the plate to infiltrate the cells;

4. The pancreatin was sucked out. The culture plate was placed in an incubator. Digestion was carried out for about 3 min at 37° C.;

5. 4 mL of complete culture solution was added to the culture plate to stop the digestion. The cells were carefully scoured with micropipette (1 ml) to give a uniform single cell suspension. The suspension was implanted into a 96-well cell culture plate by 7000 cells/100 µL per well. The culture plate was incubated overnight under 5% $CO_2$ at 37° C. In day 2, 100 µL of culture solution comprising a compound was added in each well. The plate was further incubated for 69.5 h under 5% $CO_2$ at 37° C.;

6. The culture solution was sucked out. 100 uL of TCA fixed cells which were diluted to 10% were added to each well. The plate was kept in a refrigerator for 1 h at 4° C.

7. TCA stationary liquid was sucked out. Each well was washed with 150 µL of $ddH_2O$ five times;

8. After the stationary liquid was cleansed, the plate was dried in the air at the room temperature;

9. 60 µL of SRB staining solution was added in each well. The well was stained for 15 min at the room temperature;

10. The SRB staining solution was sucked out. Each well was washed with 150 µL of 1% glacial acetic acid five times;

11. After the SRB staining solution was cleansed, the plate was dried in the air at the room temperature;

12. 100 µL of 10 mM Tris was added in each well. The plate was vibrated to dissolve out SRB;

13. OD values were determined at 570 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 5

Growth Inhibition Activity at 2000 nM of Some Compounds in Examples on MDA-MB-453 Cells

| Compounds | Inhibition Ratio (%) | Compounds | Inhibition Ratio (%) | Compounds | Inhibition Ratio (%) |
|---|---|---|---|---|---|
| Example 1 | 77.7 | Example 3 | 73.9 | Example 8 | 75.3 |
| Example 10 | 78.5 | Example 12 | 73.7 | Example 14 | 74.4 |
| Example 20 | 82.4 | Example 22 | 71.1 | Example 24 | 79.8 |
| Example 26 | 79.9 | Example 28 | 81.9 | Example 30 | 79.9 |
| Example 32 | 78.3 | Example 34 | 80.5 | Example 35 | 77.1 |
| Example 38 | 75.8 | Example 40 | 73 | Example 44 | 68.5 |
| Example 60 | 76.3 | Example 62 | 83.7 | Example 64 | 73.5 |
| Example 66 | 73.9 | Example 76 | 62.7 | Example 77 | 79.7 |
| Example 81 | 72 | Example 94 | 75.8 | Example 95 | 68.2 |

Example 5: 22Rv1 Cell Growth Inhibition Test (SRB Assay)

I. Assay Materials

Cell strains: 22Rv1 (human prostate cancer cell strains); SRB: 0.4% (w/v) working solution was formulated with 1% glacial acetic acid, reserved at 4° C.; antitumor compounds; DMSO.

II. Reagents and Consumable Materials

Culture medium: 90% RPMI-1640+10% FBS; Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. 1.5 mL of 0.25% pancreatin was added to the plate to infiltrate the cells;

4. The pancreatin was sucked out. The culture plate was placed in an incubator. Digestion was carried out for about 3 min at 37° C.;

5. 4 mL of complete culture solution was added to the culture plate to stop the digestion. The cells were carefully scoured with micropipette (1 ml) to give a uniform single cell suspension. The suspension was implanted into a 96-well cell culture plate by 7000 cells/100 µL per well. The culture plate was incubated overnight under 5% $CO_2$ at 37° C. In day 2, 100 µL of culture solution comprising a compound was added in each well. The plate was further incubated for 73 h under 5% $CO_2$ at 37° C.;

6. The culture solution was sucked out. 100 uL of TCA fixed cells which were diluted to 10% were added to each well. The plate was kept in a refrigerator for 1 h at 4° C.

7. TCA stationary liquid was sucked out. Each well was washed with 150 µL of dd$H_2O$ five times;

8. After the stationary liquid was cleansed, the plate was dried in the air at the room temperature;

9. 60 µL of SRB staining solution was added in each well. The well was stained for 15 min at the room temperature;

10. The SRB staining solution was sucked out. Each well was washed with 150 µL of 1% glacial acetic acid five times;

11. After the SRB staining solution was cleansed, the plate was dried in the air at the room temperature;

12. 100 µL of 10 mM Tris was added in each well. The plate was vibrated to dissolve out SRB;

13. OD values were determined at 570 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 6

Growth Inhibition Activity at 222 nM of Some Compounds in Examples on 22Rv1 Cells

| Compounds | Inhibition Ratio (%) | Compounds | Inhibition Ratio (%) | Compounds | Inhibition Ratio (%) |
|---|---|---|---|---|---|
| Example 1 | 52.2 | Example 3 | 61.9 | Example 8 | 56.8 |
| Example 10 | 62.7 | Example 12 | 53.3 | Example 14 | 52.1 |
| Example 20 | 60.9 | Example 22 | 56.3 | Example 24 | 63.6 |
| Example 26 | 60.8 | Example 28 | 63.1 | Example 30 | 62.3 |
| Example 32 | 61.7 | Example 34 | 63.3 | Example 35 | 58.5 |
| Example 38 | 56.3 | Example 40 | 50.5 | Example 44 | 48.5 |
| Example 60 | 52.9 | Example 62 | 57 | Example 64 | 54.8 |

TABLE 6-continued

Growth Inhibition Activity at 222 nM of Some Compounds in Examples on 22Rv1 Cells

| Compounds | Inhibition Ratio (%) | Compounds | Inhibition Ratio (%) | Compounds | Inhibition Ratio (%) |
|---|---|---|---|---|---|
| Example 66 | 59 | Example 76 | 49.2 | Example 77 | 57.9 |
| Example 81 | 56.5 | Example 94 | 60.7 | Example 95 | 51.3 |

Example 6: A375 Cell Growth Inhibition Test (MTT Assay)

I. Assay Materials

Cell strains: A375 (human cutaneous melanoma cell strains); MTT: nitroblue tetrazolium; antitumor compounds; compound A: 3'-pyrrolyldoxorubicin-14-oxo-succinic acid monoester; DMSO.

II. Reagents and Consumable Materials

Culture medium: 90% DMEM+10% FBS (fetal calf serum); Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. PBS was sucked out. 1.5 mL of 0.25% pancreatin was added to the plate to infiltrate the cells for 1 min;

4. The culture plate was placed in an incubator. Digestion was carried out for about 5 min at 37° C.;

5. 3 mL of complete culture solution was added to the culture plate to stop the digestion. The cells were carefully scoured with micropipette (1 ml) to give a uniform cell suspension. The suspension was implanted into a 96-well cell culture disc by 3000 cells/100 µL per well. The culture plate was incubated overnight under 5% $CO_2$ at 37° C. In day 2, 100 µL of culture solution comprising a compound was added in each well. The plate was further incubated for 72 h under 5% $CO_2$ at 37° C.;

6. The culture solution was sucked out;

7. 100 µL of serum-free culture solution containing 0.5 mg/mL MTT was added in each well. The plate was incubated for 3 h;

8. The culture solution was carefully sucked out;

9. 100 µL of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 7

Growth Inhibition Activity of Some Compounds in Examples on A375 Cells

| Compounds | Inhibition Activity (IC$_{50}$/nM) | Compounds | Inhibition Activity (IC$_{50}$/nM) | Compounds | Inhibition Activity (IC$_{50}$/nM) |
|---|---|---|---|---|---|
| Compound A | 207 | Example 6 | 67 | Example 89 | 48 |
| Example 81 | 67 | Example 97 | 28 | Example 99 | 35 |

TABLE 8

Growth Inhibition Activity of Some Compounds in Examples on A431 Cells

| Compounds | Inhibition Activity (IC$_{50}$/nM) | Compound | Inhibition Activity (IC$_{50}$/nM) | Compound | Inhibition Activity (IC$_{50}$/nM) |
|---|---|---|---|---|---|
| Compound A | 68 | Example 81 | 42 | Example 89 | 46 |
| Example 97 | 45 | | | | |

Example 7: A431 Cell Growth Inhibition Test (MTT Assay)

I. Assay Materials

Cell strains: A431 (human epidermal carcinoma cell strains); MTT: nitroblue tetrazolium; antitumor compounds; compound A: 3'-pyrrolyldoxorubicin-14-oxo-succinic acid monoester; DMSO.

II. Reagents and Consumable Materials

Culture medium: 45% DMEM+45% F12+10% FBS (fetal calf serum); Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;
2. The culture solution was sucked out. The plate was washed with 5 mL of PBS once or twice;
3. PBS was sucked out. 1.5 mL of 0.25% pancreatin was added to the plate to infiltrate the cells for 1 min;
4. The culture plate was placed in an incubator. Digestion was carried out for about 5 min at 37° C.;
5. 3 mL of complete culture solution was added to the culture plate to stop the digestion. The cells were carefully scoured with micropipette (1 mL) to give a uniform cell suspension. The suspension was implanted into a 96-well cell culture disc by 2500 cells/100 µL per well. The culture plate was incubated overnight under 5% CO$_2$ at 37° C. In day 2, 100 µL of culture solution comprising a compound was added in each well. The plate was further incubated for 72 h under 5% CO$_2$ at 37° C.;
6. The culture solution was sucked out;
7. 100 µL of serum-free culture solution containing 0.5 mg/mL MTT was added in each well. The plate was incubated for 3 h;
8. The culture solution was carefully sucked out;
9. 100 µL of DMSO was added in each well and vibrated to dissolve;
10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

Example 8: MCF-7 Cell Growth Inhibition Test (SRB Assay)

I. Assay Materials

Cell strains: MCF-7 (human breast cancer cell strains); SRB: 0.4% (w/v) working solution was formulated with 1% glacial acetic acid, reserved at 4° C.; antitumor compounds; compound A: 3'-pyrrolyldoxorubicin-14-oxo-succinic acid monoester; DMSO.

II. Reagents and Consumable Materials

Culture medium: 90% EMEM+10% FBS; Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;
2. The culture solution was sucked out. The plate was washed with 5 mL of PBS once or twice;
3. 1.5 mL of 0.25% pancreatin was added to the plate to infiltrate the cells;
4. The pancreatin was sucked out. The culture plate was placed in an incubator. Digestion was carried out for about 3 min at 37° C.;
5. 4 mL of complete culture solution was added to the culture plate to stop the digestion. The cells were carefully scoured with micropipette (1 mL) to give a uniform single cell suspension. The suspension was implanted into a 96-well cell culture plate by 10000 cells/100 µL per well. The culture plate was incubated overnight under 5% CO$_2$ at 37° C. In day 2, 100 µL of culture solution comprising a compound was added in each well. The plate was further incubated for 73 h under 5% CO$_2$ at 37° C.;
6. The culture solution was sucked out. 100 uL of TCA fixed cells which were diluted to 10% were added to each well. The plate was kept in a refrigerator for 1 h at 4° C.
7. TCA stationary liquid was sucked out. Each well was washed with 150 µL of ddH$_2$O five times;
8. After the stationary liquid was cleansed, the plate was dried in the air at the room temperature;
9. 60 µL of SRB staining solution was added in each well. The well was stained for 15 min at the room temperature;
10. The SRB staining solution was sucked out. Each well was washed with 150 µL of 1% glacial acetic acid five times;
11. After the SRB staining solution was cleansed, the plate was dried in the air at the room temperature;
12. 100 µL of 10 mM Tris was added in each well. The plate was vibrated to dissolve out SRB;
13. OD values were determined at 570 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 9

Growth Inhibition Activity of Some Compounds in Examples on MCF-7 Cells

| Compound | Inhibition Activity ($IC_{50}$/nM) | Compound | Inhibition Activity ($IC_{50}$/nM) | Compound | Inhibition Activity ($IC_{50}$/nM) |
|---|---|---|---|---|---|
| Compound A | 785 | Example 81 | 225 | Example 89 | 333 |

Example 9: NCI-446 Cell Growth Inhibition Test (MTT Assay)

I. Assay Materials

Cell strains: NCI-446 (human small cell lung cancer cell strains); MTT: nitroblue tetrazolium; antitumor compounds; compound A: 3'-pyrrolyldoxorubicin-14-oxo-succinic acid monoester; DMSO.

II. Reagents and Consumable Materials

Culture medium: 90% RPMI1640+10% FBS (fetal calf serum); Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 ml of PBS once or twice;

3. PBS was sucked out. 1.5 mL of 0.25% pancreatin was added to the plate to infiltrate the cells for 1 min;

4. The culture plate was placed in an incubator. Digestion was carried out for about 3 min at 37° C.;

5. 3 mL of complete culture solution was added to the culture plate to stop the digestion. The cells were carefully scoured with micropipette (1 mL) to give a uniform cell suspension. The suspension was implanted into a 96-well cell culture disc by 4000 cells/100 μL per well. The culture plate was incubated overnight under 5% $CO_2$ at 37° C. In day 2, 100 μL of culture solution comprising a compound was added in each well. The plate was further incubated for 72 h under 5% $CO_2$ at 37° C.;

6. The culture solution was sucked out;

7. 100 μL of serum-free culture solution containing 0.5 mg/mL MTT was added in each well. The plate was incubated for 3 h;

8. The culture solution was carefully sucked out;

9. 100 μL of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 10

Growth Inhibition Activity of Some Compounds in Examples on NCI-446 Cells

| Compound | Inhibition Activity ($IC_{50}$/nM) | Compound | Inhibition Activity ($IC_{50}$/nM) |
|---|---|---|---|
| Compound A | 234 | Example 89 | 140 |

Example 10: NCI-H460 Cell Growth Inhibition Test (MTT Assay)

I. Assay Materials

Cell strains: NCI-H460 (human large cell lung cancer cell strains); MTT: nitroblue tetrazolium; antitumor compounds; compound A: 3'-pyrrolyldoxorubicin-14-oxo-succinic acid monoester; DMSO.

II. Reagents and Consumable Materials

Culture medium: 90% RPMI1640+10% FBS (fetal calf serum); Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. PBS was sucked out. 1.5 mL of 0.25% pancreatin was added to the plate to infiltrate the cells for 1 min;

4. The culture plate was placed in an incubator. Digestion was carried out for about 3 min at 37° C.;

5. 3 mL of complete culture solution was added to the culture plate to stop the digestion. The cells were carefully scoured with micropipette (1 mL) to give a uniform cell suspension. The suspension was implanted into a 96-well cell culture disc by 2000 cells/100 μL per well. The culture plate was incubated overnight under 5% $CO_2$ at 37° C. In day 2, 100 μL of culture solution comprising a compound was added in each well. The plate was further incubated for 72 h under 5% $CO_2$ at 37° C.;

6. The culture solution was sucked out;

7. 100 μL of serum-free culture solution containing 0.5 mg/mL MTT was added in each well. The plate was incubated for 3 h;

8. The culture solution was carefully sucked out;

9. 100 μL of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 11

Growth Inhibition Activity of Some Compounds in Examples on NCI-460 Cells

| Compound | Inhibition Activity (IC$_{50}$/nM) | Compound | Inhibition Activity (IC$_{50}$/nM) |
|---|---|---|---|
| Compound A | 21 | Example 89 | 2.5 |

Example 11: B16 Cell Growth Inhibition Test (MTT Assay)

I. Assay Materials

Cell strains: B16 (mouse melanoma cell strains); MTT: nitroblue tetrazolium; antitumor compounds; compound A: 3'-pyrrolyldoxorubicin-14-oxo-succinic acid monoester; DMSO.

II. Reagents and Consumable Materials

Culture medium: 90% RPMI1640+10% FBS (fetal calf serum); Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. PBS was sucked out. 1.5 mL of 0.25% pancreatin was added to the plate to infiltrate the cells for 1 min;

4. The culture plate was placed in an incubator. Digestion was carried out for about 1 min at 37° C.;

5. 3 mL of complete culture solution was added to the culture plate to stop the digestion. The cells were carefully scoured with micropipette (1 mL) to give a uniform cell suspension. The suspension was implanted into a 96-well cell culture disc by 2500 cells/100 μL per well. The culture plate was incubated overnight under 5% CO$_2$ at 37° C. In day 2, 100 μL of culture solution comprising a compound was added in each well. The plate was further incubated for 72 h under 5% CO$_2$ at 37° C.;

6. The culture solution was sucked out;

7. 100 μl of serum-free culture solution containing 0.5 mg/mL MTT was added in each well. The plate was incubated for 3 h;

8. The culture solution was carefully sucked out;

9. 100 μL of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 12

Growth Inhibition Activity of Some Compounds in Examples on B16 Cells

| Compound | Inhibition Activity (IC$_{50}$/nM) | Compound | Inhibition Activity (IC$_{50}$/nM) | Compound | Inhibition Activity (IC$_{50}$/nM) |
|---|---|---|---|---|---|
| Compound A | 32 | Example 62 | 3 | Example 89 | 3 |

Example 12: 786-O Cell Growth Inhibition Test (MTT Assay)

I. Assay Materials

Cell strains: 786-O (human clear cell adenocarcinoma cell strains); MTT: nitroblue tetrazolium; antitumor compounds; compound A: 3'-pyrrolyldoxorubicin-14-oxo-succinic acid monoester; DMSO.

II. Reagents and Consumable Materials

Culture medium: 90% RPMI1640+10% FBS (fetal calf serum); Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. PBS was sucked out. 1.5 mL of 0.25% pancreatin was added to the plate to infiltrate the cells for 1 min;

4. The culture plate was placed in an incubator. Digestion was carried out for about 1 min at 37° C.;

5. 3 mL of complete culture solution was added to the culture plate to stop the digestion. The cells were carefully scoured with micropipette (1 mL) to give a uniform cell suspension. The suspension was implanted into a 96-well cell culture disc by 2000 cells/100 μL per well. The culture plate was incubated overnight under 5% CO$_2$ at 37° C. In day 2, 100 μL of culture solution comprising a compound was added in each well. The plate was further incubated for 72 h under 5% CO$_2$ at 37° C.;

6. The culture solution was sucked out;

7. 100 μL of serum-free culture solution containing 0.5 mg/mL MTT was added in each well. The plate was incubated for 3 h;

8. The culture solution was carefully sucked out;

9. 100 μL of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

TABLE 13

Growth Inhibition Activity of Some Compounds in Examples on 786-O Cells

| Compound | Inhibition Activity ($IC_{50}$/nM) | Compound | Inhibition Activity ($IC_{50}$/nM) | Compound | Inhibition Activity ($IC_{50}$/nM) |
|---|---|---|---|---|---|
| Compound A | 180 | Example 62 | 110 | Example 90 | 90 |

TABLE 14

Growth Inhibition Activity of Some Compounds in Examples on DU-145 Cells

| Compounds | Inhibition Activity ($IC_{50}$/nM) | Compounds | Inhibition Activity ($IC_{50}$/nM) | Compound | Inhibition Activity ($IC_{50}$/nM) |
|---|---|---|---|---|---|
| Compound A | 99 | Example 62 | 34 | Example 89 | 56 |
| Compound 90 | 30 | Example 92 | 61 | | |

Example 13: DU-145 Cell Growth Inhibition Test (MTT Assay)

I. Assay Materials

Cell strains: DU-145 (prostate cancer cell strains); MTT: nitroblue tetrazolium; antitumor compounds; compound A: 3'-pyrrolyldoxorubicin-14-oxo-succinic acid monoester; DMSO.

II. Reagents and Consumable Materials

Culture medium: 90% EMEM+10% FBS (fetal calf serum); Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. PBS was sucked out. 1.5 mL of 0.25% pancreatin was added to the plate to infiltrate the cells for 1 min;

4. The culture plate was placed in an incubator. Digestion was carried out for about 1 min at 37° C.;

5. 3 mL of complete culture solution was added to the culture plate to stop the digestion. The cells were carefully scoured with micropipette (1 mL) to give a uniform cell suspension. The suspension was implanted into a 96-well cell culture disc by 4000 cells/100 µL per well. The culture plate was incubated overnight under 5% $CO_2$ at 37° C. In day 2, 100 µL of culture solution comprising a compound was added in each well. The plate was further incubated for 72 h under 5% $CO_2$ at 37° C.;

6. The culture solution was sucked out;

7. 100 µL of serum-free culture solution containing 0.5 mg/mL MTT was added in each well. The plate was incubated for 3 h;

8. The culture solution was carefully sucked out;

9. 100 µL of DMSO was added in each well and vibrated to dissolve;

10. OD values were determined at 490 nM.

IV. Results and Treatments

1. Calculation of Relative Inhibition Ratio

The inhibition ratio of a compound on cell growth=(PC−n)/(PC−NC)×100% wherein:

PC: OD values of cells after normal growth in control wells without a compound;

n: OD values of cells after growth in test wells with a compound;

NC: Background OD values of blank wells without a compound and cells.

Example 14: Hep3B Cell Growth Inhibition Test (SRB Assay)

I. Assay Materials

Cell strains: Hep3B (liver cancer cell strains); SRB: 0.4% (w/v) working solution was formulated with 1% glacial acetic acid, reserved at 4° C.; antitumor compounds; compound A: 3'-pyrrolyldoxorubicin-14-oxo-succinic acid monoester; DMSO.

II. Reagents and Consumable Materials

Culture medium: 90% RPMI-1640+10% FBS; Pancreatin (0.25% (w/v) solution was formulated with PBS, 0.53 mM of EDTA was added in the formulation); PBS; 96-well culture plate.

III. Assay Process

1. A plate (10 cm) of cells in logarithmic growth phase that were normally cultured was collected;

2. The culture solution was sucked out. The plate was washed with 5 mL of PBS once or twice;

3. 1.5 mL of 0.25% pancreatin was added to the plate to infiltrate the cells;

4. The pancreatin was sucked out. The culture plate was placed in an incubator. Digestion was carried out for about 3 min at 37° C.;

5. 4 mL of complete culture solution was added to the culture plate to stop the digestion. The cells were carefully scoured with micropipette (1 mL) to give a uniform single cell suspension. The suspension was implanted into a 96-well cell culture plate by 5000 cells/100 µL per well. The culture plate was incubated overnight under 5% $CO_2$ at 37° C. In day 2, 100 µL of culture solution comprising a compound was added in each well. The plate was further incubated for 72 h under 5% $CO_2$ at 37° C.;

6. The culture solution was sucked out. 100 uL of TCA fixed cells which were diluted to 10% were added to each well. The plate was kept in a refrigerator for 1 h at 4° C.

7. TCA stationary liquid was sucked out. Each well was washed with 150 µL of dd$H_2$O five times;

8. After the stationary liquid was cleansed, the plate was dried in the air at the room temperature;

9. 60 µL of SRB staining solution was added in each well. The well was stained for 15 min at the room temperature;

10. The SRB staining solution was sucked out. Each well was washed with 150 µL of 1% glacial acetic acid five times;

11. After the SRB staining solution was cleansed, the plate was dried in the air at the room temperature;

12. 100 µL of 10 mM Tris was added in each well. The plate was vibrated to dissolve out SRB;

13. OD values were determined at 570 nM.

IV. Results and Treatments

1. Calculation of Relative Inhibition Ratio

The inhibition ratio of the compound on cell growth=(PC−n)/(PC−NC)×100% wherein:

PC: OD values of cells after normal growth in control wells without a compound;

n: OD values of cells after growth in test wells with a compound;
NC: Background OD values of blank wells without a compound and cells.

TABLE 15

Growth Inhibition Activity of Some Compounds in Examples on Hep3B Cells

| Compound | Inhibition Activity (IC$_{50}$/nM) | Compound | Inhibition Activity (IC$_{50}$/nM) | Compound | Inhibition Activity (IC$_{50}$/nM) |
|---|---|---|---|---|---|
| Compound A | 444 | Example 90 | 29 | Example 92 | 28 |

Example 15: SK-Br-3 Cell Growth Inhibition Test (SRB Assay)

I. Assay Materials
Cell strains: SK-Br-3 (human breast cancer cell strains); SRB: 0.4% (w/v) working solution was formulated with 1% glacial acetic acid, reserved at 4° C.; antitumor compounds; compound A: 3'-pyrrolyldoxorubicin-14-oxo-succinic acid monoester; DMSO.

II. Reagents and Consumable Materials
Culture medium: 85% DMEM+15% FBS; pancreatin (0.25% (w/v) solution was formulated with PBS, 0.53 mM of EDTA was added in the formulation); PBS; 96-well culture plate.

III. Assay Process
1. A plate (10 cm) of cells in logarithmic growth phase that were normally cultured was collected;
2. The culture solution was sucked out. The plate was washed with 5 mL of PBS once or twice;
3. 1.5 mL of 0.25% pancreatin was added to the plate to infiltrate the cells;
4. The pancreatin was sucked out. The culture plate was placed in an incubator. Digestion was carried out for about 2 min at 37° C.;
5. 4 mL of complete culture solution was added to the culture plate to stop the digestion. The cells were carefully scoured with micropipette (1 mL) to give a uniform single cell suspension. The suspension was implanted into a 96-well cell culture plate by 10000 cells/100 μL per well. The culture plate was incubated overnight under 5% CO$_2$ at 37° C. In day 2, 100 μL of culture solution comprising a compound was added in each well. The plate was further incubated for 72 h under 5% CO$_2$ at 37° C.;
6. The culture solution was sucked out. 100 uL of TCA fixed cells which were diluted to 10% were added to each well. The plate was kept in a refrigerator for 1 h at 4° C.
7. TCA stationary liquid was sucked out. Each well was washed with 150 μL of ddH$_2$O five times;
8. After the stationary liquid was cleansed, the plate was dried in the air at the room temperature;
9. 60 μL of SRB staining solution was added in each well. The well was stained for 15 min at the room temperature;
10. The SRB staining solution was sucked out. Each well was washed with 150 μL of 1% glacial acetic acid five times;
11. After the SRB staining solution was cleansed, the plate was dried in the air at the room temperature;
12. 100 μL of 10 mM Tris was added in each well. The plate was vibrated to dissolve out SRB;
13. OD values were determined at 570 nM.

IV. Results and Treatments
1. Calculation of Relative Inhibition Ratio
The inhibition ratio of a compound on cell growth=(PC−n)/(PC−NC)×100% wherein:
PC: OD values of cells after normal growth in control wells without a compound;
n: OD values of cells after growth in test wells with a compound;
NC: Background OD values of blank wells without a compound and cells.

TABLE 16

Growth Inhibition Activity of Some Compounds in Examples on SK-Br-3 Cells

| Compound | Inhibition Activity (IC$_{50}$/nM) | Compound | Inhibition Activity (IC$_{50}$/nM) |
|---|---|---|---|
| Compound A | 93 | Example 98 | 15 |

Assay on MTD (Maximum Tolerated Dose) In Vivo of Mice

Assay on Maximum Tolerated Dose of Compound
Assay animals: mice of ICR strain with a weight of 18-22 g, purchased from Beijing Vital River Laboratories Limited, License SCXK (jing) 2007-0001.

Administration Regimen: each experimental animal was administered with corresponding dosage of tested substance once by injection of caudal vain every three days. Each dosage was initially designed as 5 times of administration. The specific time of administration depended on the conditions of the animals. It should be carefully observed the behavior conditions of the animals within 2 hours after administration. The animal's behavior was observed every 4 hours in the day of administration. The survival conditions and weight of animals were recorded every day and observed for whether abnormality occurred on the body surface thereof. The experimental animals were sacrificed on 14 day after administration and dissected for observation.

1. Tested Substance 1: 3'-Pyrrolyldoxorubicin
1) Administration Groups
I group: (20 mg/kg) group;
II group: (25 mg/kg) group;
III group: (30 mg/kg) group;
IV group: solvent control group;
There were four groups in total. Each group consisted of five male mice and five female mice.

2) Assay Results
(1) The effects on weights of experimental animals are shown in FIG. 1.
(2) The effects on survival ratio of experimental animals are shown in Table 17.

TABLE 17

| Dosage (mg/kg) | Times of Administration | Total Dosage (mg/kg) | Number of Animals per Group ♂/♀ | Number of Dead Animals ♂/♀ | Mortality Rate (%) |
|---|---|---|---|---|---|
| 20 | 4 | 80 | 5/5 | 5/5 | 100 |
| 25 | 4 | 100 | 5/5 | 5/5 | 100 |
| 30 | 3 | 90 | 5/5 | 5/5 | 100 |
| Control | 4 | 0 | 5/5 | 0/0 | 0 |

Note:
♂: male mouse;
♀: female mouse

3) Assay Results and Discussions

The experimental animals in the solvent control group exhibited normally increased weight without death. Death occurred in succession in the experimental animals after administration with 20 mg/kg or 25 mg/kg four times. Death occurred in succession in the experimental animals after administration with 30 mg/kg three times. The mortality rate is 100%. The MTD of the tested compound 1 is less than 20 mg/kg (0.0338 mmol/kg) according to the q4d×5 administration regimen.

2. Tested Compound 2: The Compound of Example 96

1) Administration Groups

I group: (40 mg/kg) group;
II group: (45 mg/kg) group;
III group: (50 mg/kg) group;
IV group: (55 mg/kg) group;
V group: (60 mg/kg) group;

There were five groups in total. Each group consisted of six male mice and six female mice.

Figure 2:
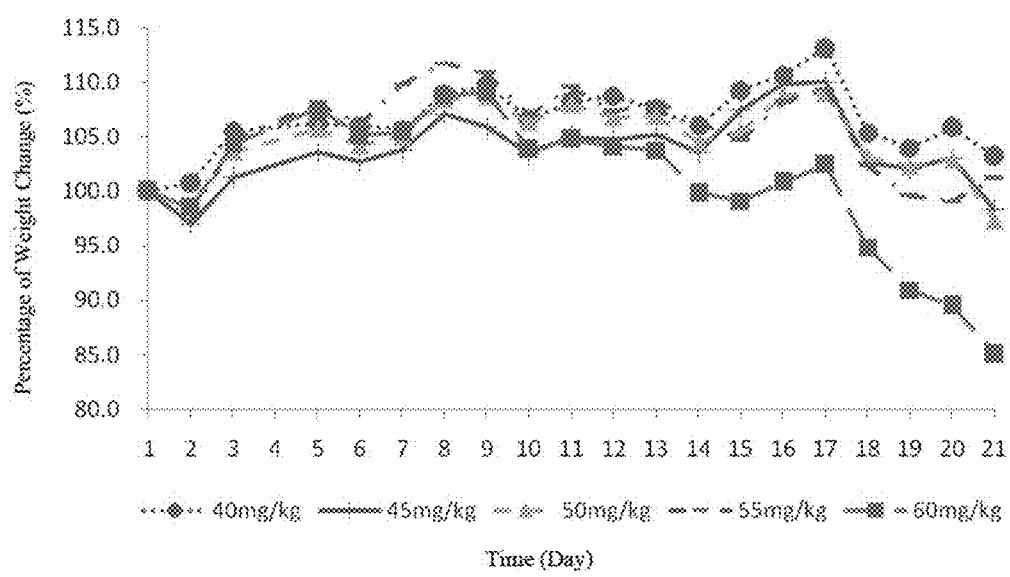
FIG. 2 shows effects of the compound in Example 96 according to the present application on the body weight of experimental animals.

2) Assay Results (1) The effects on weights of experimental animals are shown in FIG. 2.

(2) The effects on survival ratio of experimental animals are shown in Table 18.

TABLE 18

| Dosage (mg/kg) | Times of Administration | Total Dosage (mg/kg) | Number of Animals per Group ♂/♀ | Number of Dead Animals ♂/♀ | Mortality Rate (%) |
| --- | --- | --- | --- | --- | --- |
| 40 | 5 | 200 | 6/6 | 0/1 | 8.33 |
| 45 | 5 | 225 | 6/6 | 0/0 (1/2a) | 0 |
| 50 | 5 | 250 | 6/6 | 0/0 (1/1a) | 0 |
| 55 | 5 | 275 | 6/6 | 5/4 (5/3a) | 25 |
| 60 | 5 | 300 | 6/6 | 3/4 | 53.85 |

Note:
♂: male mouse;
♀: female mouse a represents that the experimental animal died immediately after the injection of drug rather than death caused by cytotoxicity. The animal which died immediately after administration was not counted in the calculation of mortality rate (mortality rate=the number of experimental animals which did not die immediately after injection/(the number of animals in group—the number of experimental animals died immediately)×100%).

3) Assay Results and Discussions

There was one dead animal in the 40 mg/kg dosage group. The mortality rate is 8.33%. The dead animal was dissected for observation of various organs. The organs did not exhibit obvious abnormality. However, there was several bite marks on the surface of the skin of the dead animal. This animal did not have significant weight loss. Therefore, it is presumed that the death is caused by cytotoxicity factor rather than drug. Two experimental animals died immediately after the fifth administration in the 50 mg/kg dosage group. The two dead animals did not have significant weight loss. It is presumed that the death is caused by cytotoxicity factor rather than drug. The MTD of the tested compound 2 is 50-55 mg/kg (0.0525-0.0578 mmol/kg) according to the q4d×5 administration regimen.

3. Tested Substance 3: 3'-Pyrrolyldoxorubicin-14-Oxo-Succinic Acid Monoester

1) Administration Groups

I group: (30 mg/kg) group;
II group: (40 mg/kg) group;
III group: (50 mg/kg) group;
IV group: (60 mg/kg) group;

There were four groups in total. Each group consisted of five male mice and five female mice.

Figure 3:
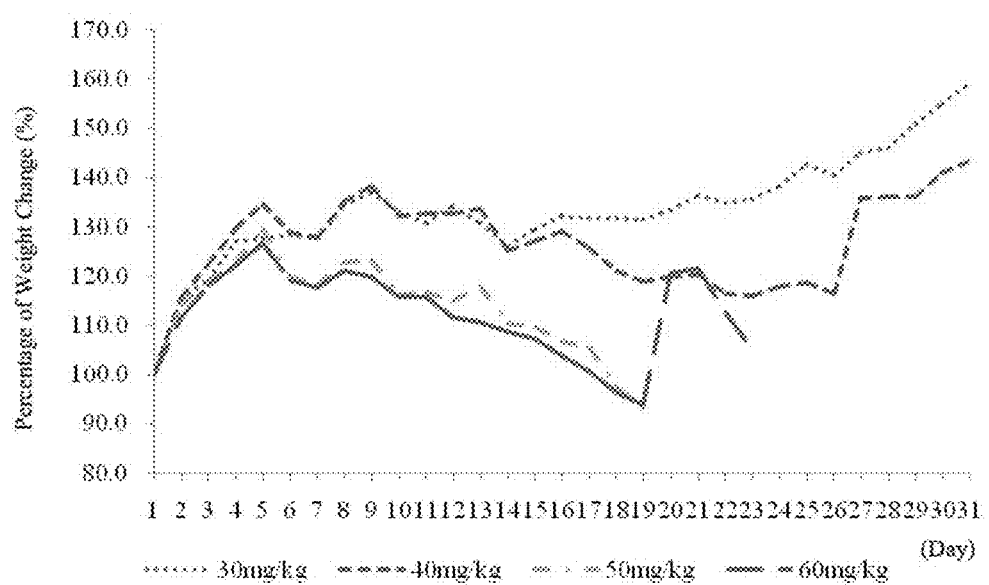
FIG. 3 shows effects of 3'-pyrrolyldoxorubicin-14-oxo-succinic acid monoester on the body weight of experimental animals.

2) Assay Results (1) The effects on weights of experimental animals are shown in FIG. 3.

(2) The effects on survival ratio of experimental animals are shown in Table 19.

TABLE 19

| Dosage (mg/kg) | Times of Administration | Total Dosage (mg/kg) | Number of Animals per Group ♂/♀ | Number of Dead Animals ♂/♀ | Mortality Rate (%) |
| --- | --- | --- | --- | --- | --- |
| 30 | 5 | 150 | 5/5 | 0/1 | 10 |
| 40 | 5 | 200 | 5/5 | 3/2 | 50 |
| 50 | 5 | 250 | 5/5 | 5/5 | 100 |
| 60 | 5 | 300 | 5/5 | 5/5 | 100 |

Note:
♂: male mouse;
♀: female mouse

3) Assay Results and Discussions

The lethality rates of mice of ICR strain are 10%, 50%, 100%, 100% respectively, according to the administration regimens of 30 mg/kg, 40 mg/kg, 50 mg/kg, 60 mg/k of compounds. One experimental animal dried without significant weight loss in the animals of 30 mg/kg group, indicating that this dead animal in 30 mg/kg group does not exclude the cause of animal's individual difference. The MTD of the tested compound 3 is approximately 30 mg/kg (0.0433 mmol/kg) according to the q4d×5 administration regimen.

The above general description regarding the invention disclosed herein and the description of the specific embodiments thereof cannot be construed as the limitation to the technical solutions of the invention. One of ordinary skill in the art can add, delete or combine the technical features disclosed in the above general description and/or specific embodiments (including Examples) to form other technical solutions within the invention according to the disclosure herein without departing from the constitutive elements of the invention.

What is claimed is:

1. A method for treating-tumor and/or cancer, comprising administering to a subject in need thereof a therapeutically effective amount of a compound represented by formula (I) or a pharmaceutically acceptable salt thereof, or a formulation comprising a compound represented by formula (I) or a pharmaceutically acceptable salt thereof, and a pharmaceutically acceptable carrier,

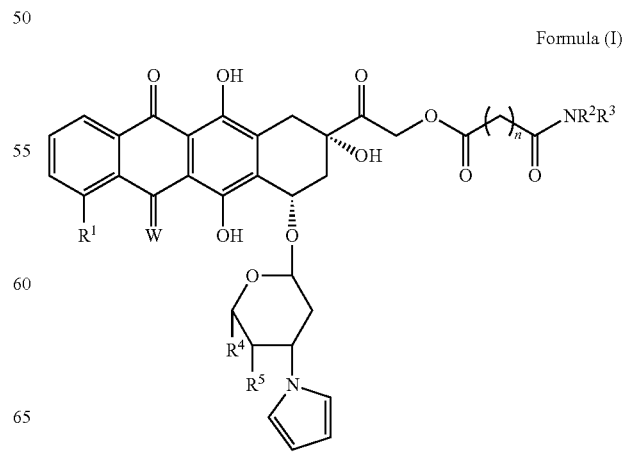

Formula (I)

wherein:
R¹ is selected from the group consisting of H, optionally substituted alkyl, and optionally substituted alkoxy;
R² is selected from the group consisting of H, optionally substituted aryl, optionally substituted heteroaryl, optionally substituted (alkyleneoxy)$_m$alkyl, optionally substituted heterocyclyl, optionally substituted alkyl, and optionally substituted —S(=O)$_2$R;
R³ is selected from the group consisting of H, optionally substituted aryl, optionally substituted heteroaryl, optionally substituted (alkyleneoxy)$_m$alkyl, optionally substituted heterocyclyl, optionally substituted alkyl, and optionally substituted —S(=O)$_2$R;
or NR²R³ represents optionally substituted heterocyclyl;
wherein R comprises optionally substituted alkyl, optionally substituted cyclohydrocarbyl, optionally substituted heterocyclyl, optionally substituted aryl, or optionally substituted heteroaryl;
m is selected from the group consisting of 0, 23, 2, 3, 4, 5, 6, 7, 8, 9, 10, and 11;
W is selected from the group consisting of O and NH;
R⁴ is selected from the group consisting of H, F, and optionally substituted alkyl;
R⁵ is selected from the group consisting of H, F, optionally substituted alkyl and OR⁶, wherein R⁶ is selected from the group consisting of H and tetrahydropyran-2-yl; and
n is selected from the group consisting of 23, 2 and 3;
wherein the tumor and/or cancer is selected from the group consisting of gastric cancer, intestine cancer, head and neck cancer, cervical cancer, brain glioma, various leukemia, lymphoma, and multiple bone marrow cancer.

2. The method of claim 1, wherein R¹ is selected from the group consisting of H and OCH₃.

3. The method of claim 1, wherein W is O.

4. The method of claim 1, wherein R⁴ is CH₃.

5. The method of claim 1, wherein R⁵ is selected from the group consisting of OH and (tetrahydropyran-2-yl)oxy.

6. The method of claim 1, wherein R² is selected from the group consisting of H, methyl, ethyl, (morpholinylmethyl)phenyl, 4-((morpholin-1-yl)methyl)phenyl, (dimethylaminomethyl)phenyl, 4-((dimethylamino)methyl)phenyl, 2-(2-(dimethylamino)ethoxy)ethyl, morpholin-1-yl, piperidin-1-yl, tetrahydropyrrol-1-yl, 4-(2-hydroxyethyl)piperazin-1-yl, (4-methylpiperazin)-1-yl, (4-ethylpiperazin)-1-yl, 2-(tetrahydropyrrol-1-yl)ethyl, 3-(tetrahydropyrrol-1-yl)propyl, (2-(morpholin-1-yl)pyridin)-4-yl, (2-(morpholin-1-yl)pyridin)-5-yl, pyridin-2-yl, pyridin-3-yl, pyridin-4-yl, (pyridin-4-yl)methyl, (pyridin-3-yl)methyl, (pyridin-2-yl)methyl, 2-(pyridin-4-yl)ethyl, 2-(pyridin-3-yl)ethyl, 2-(pyridin-2-yl)ethyl, 2-(pyridin-4-yl)propyl, 2-(pyridin-3-yl)propyl, 2-(pyridin-2-yl)propyl, 2-((4-sulfamido)phenyl)ethyl, (3-(dimethylamino)propyl)piperazin-1-yl, 3-((4-sulfamido)phenyl)propyl, 3-((4-methyl)piperazin-1-yl)propyl, 3-((4-ethyl)piperazin-1-yl)propyl, 3-((4-propyl)piperazin-1-yl)propyl, 2-((4-methyl)piperazin-1-yl)ethyl, 2-((4-ethyl)piperazin-1-yl)ethyl, 2-((4-propyl)piperazin-1-yl)ethyl, 2-dimethylamino)ethyl, 2-(diethylamino)ethyl, 2-(dipropylamino)ethyl, 2-(piperidin-1-yl)ethyl, 2-(morpholin-1-yl)ethyl, 2-(tetrahydropyrrol-1-yl)ethyl, 3-(dimethylamino)propyl, 3-(diethylamino)propyl, 3-(dipropylamino)propyl, 3-(piperidin-1-yl)propyl, 3-(morpholin-1-yl)propyl, 3-(tetrahydropyrrol-1-yl)propyl, 4-(dimethylamino)butyl, 4-(diethylamino)butyl, 4-(dipropylamino)butyl, 4-(piperidin-1-yl)butyl, 4-(morpholin-1-yl)butyl, 4-(tetrahydropyrrol-1-yl)butyl, 2-(2-(2-(2-(dimethylamino)ethoxy)ethoxy)ethoxy)ethyl, 2-(2-(2-(2-(diethylamino)ethoxy)ethoxy)ethoxy)ethyl, 2-(2-(2-(2-(dipropylamino)ethoxy)ethoxy)ethoxy)ethyl, 2-(2-(2-(2-(piperidin-1-yl)ethoxy)ethoxy)ethoxy)ethyl, 2-(2-(2-(2-(morpholin-1-yl)ethoxy)ethoxy)ethoxy)ethyl, 2-(2-(2-(2-(tetrahydropyrrol-1-yl)ethoxy)ethoxy)ethoxy)ethyl, 2-(2-(2-(dimethylamino)ethoxy)ethoxy)ethyl, 2-(2-(2-(diethylamino)ethoxy)ethoxy)ethyl, 2-(2-(2-(dipropylamino)ethoxy)ethoxy)ethyl, 2-(2-(2-(piperidin-1-yl)ethoxy)ethoxy)ethyl, 2-(2-(2-(morpholin-1-yl)ethoxy)ethoxy)ethyl, 2-(2-(2-(tetrahydropyrrol-1-yl)ethoxy)ethoxy)ethyl, 6-purinyl, mesyl, benzenesulfonyl, pyrazin-2-yl, pyrimidin-2-yl, 2-hydroxyethyl, 2-(2-hydroxyethoxy)ethyl, 2-(2-(2-(2-(2-(2-(2-(2-(2-(2-hydroxyethoxy)ethoxy)ethoxy)ethoxy)ethoxy)ethoxy)ethoxy)ethoxy)ethoxy)ethyl, 2-(2-(2-(2-(2-(2-(2-(2-(2-hydroxyethoxy)ethoxy)ethoxy)ethoxy)ethoxy)ethoxy)ethoxy)ethoxy)ethyl, 2-(2-(2-(2-(2-(2-(2-hydroxyethoxy)ethoxy)ethoxy)ethoxy)ethoxy)ethoxy)ethyl, 2-(2-(2-(2-(2-(2-(2-(2-methoxyethoxy)ethoxy)ethoxy)ethoxy)ethoxy)ethoxy)ethoxy)ethyl, and 2-(2-(2-(2-hydroxyethoxy)ethoxy)ethoxy)ethyl.

7. The method of claim 1, wherein R³ is selected from the group consisting of H, methyl, ethyl, (morpholinylmethyl)phenyl, 4-((morpholin-1-yl)methyl)phenyl, (dimethylaminomethyl)phenyl, 4-((dimethylamino)methyl)phenyl, 2-(2-(dimethylamino)ethoxy)ethyl, morpholin-1-yl, piperidin-1-yl, tetrahydropyrrol-1-yl, 4-(2-hydroxyethyl)piperazin-1-yl, (4-methylpiperazin)-1-yl, (4-ethylpiperazin)-1-yl, 2-(tetrahydropyrrol-1-yl)ethyl, 3-(tetrahydropyrrol-1-yl)propyl, (2-(morpholin-1-yl)pyridin)-4-yl, (2-(morpholin-1-yl)pyridin)-5-yl, pyridin-2-yl, pyridin-3-yl, pyridin-4-yl, (pyridin-4-yl)methyl, (pyridin-3-yl)methyl, (pyridin-2-yl)methyl, 2-(pyridin-4-yl)ethyl, 2-(pyridin-3-yl)ethyl, 2-(pyridin-2-yl)ethyl, 2-(pyridin-4-yl)propyl, 2-(pyridin-3-yl)propyl, 2-(pyridin-2-yl)propyl, 2-((4-sulfamido)phenyl)ethyl, (3-(dimethylamino)propyl)piperazin-1-yl, 3-((4-sulfamido)phenyl)propyl, 3-((4-methyl)piperazin-1-yl)propyl, 3-((4-ethyl)piperazin-1-yl)propyl, 3-((4-propyl)piperazin-1-yl)propyl, 2-((4-methyl)piperazin-1-yl)ethyl, 2-((4-ethyl)piperazin-1-yl)ethyl, 2-((4-propyl)piperazin-1-yl)ethyl, 2-(dimethylamino)ethyl, 2-(diethylamino)ethyl, 2-(dipropylamino)ethyl, 2-(piperidin-1-yl)ethyl, 2-(morpholin-1-yl)ethyl, 2-(tetrahydropyrrol-1-yl)ethyl, 3-(dimethylamino)propyl, 3-(diethylamino)propyl, 3-(dipropylamino)propyl, 3-(piperidin-1-yl)propyl, 3-(morpholin-1-yl)propyl, 3-(tetrahydropyrrol-1-yl)propyl, 4-(dimethylamino)butyl, 4-(diethylamino)butyl, 4-(dipropylamino)butyl, 4-(piperidin-1-yl)butyl, 4-(morpholin-1-yl)butyl, 4-(tetrahydropyrrol-1-yl)butyl, 2-(2-(2-(2-(dimethylamino)ethoxy)ethoxy)ethoxy)ethyl, 2-(2-(2-(2-(diethylamino)ethoxy)ethoxy)ethoxy)ethyl, 2-(2-(2-(2-(dipropylamino)ethoxy)ethoxy)ethoxy)ethyl, 2-(2-(2-(2-(piperidin-1-yl)ethoxy)ethoxy)ethoxy)ethyl, 2-(2-(2-(2-(morpholin-1-yl)ethoxy)ethoxy)ethoxy)ethyl, 2-(2-(2-(2-(tetrahydropyrrol-1-yl)ethoxy)ethoxy)ethoxy)ethyl, 2-(2-(2-(dimethylamino)ethoxy)ethoxy)ethyl, 2-(2-(2-(diethylamino)ethoxy)ethoxy)ethyl, 2-(2-(2-(dipropylamino)ethoxy)ethoxy)ethyl, 2-(2-(2-(piperidin-1-yl)ethoxy)ethoxy)ethyl, 2-(2-(2-(morpholin-1-yl)ethoxy)ethoxy)ethyl, 2-(2-(2-(tetrahydropyrrol-1-yl)ethoxy)ethoxy)ethyl, 6-purinyl, mesyl, benzenesulfonyl, pyrazin-2-yl, pyrimidin-2-yl, 2-hydroxyethyl, 2-(2-hydroxyethoxy)ethyl, 2-(2-(2-(2-(2-(2-(2-(2-(2-(2-hydroxyethoxy)ethoxy)ethoxy)ethoxy)ethoxy)ethoxy)ethoxy)ethoxy)ethoxy)ethyl, 2-(2-(2-(2-(2-(2-(2-(2-(2-hydroxyethoxy)ethoxy)ethoxy)ethoxy)ethoxy)ethoxy)ethoxy)ethoxy)ethyl, 2-(2-(2-(2-(2-(2-(2-hydroxyethoxy)ethoxy)ethoxy)ethoxy)ethoxy)ethoxy)ethyl, 2-(2-(2-(2-(2-(2-(2-

(2-methoxyethoxy)ethoxy)ethoxy)ethoxy)ethoxy)ethoxy)ethoxy)ethyl, and 2-(2-(2-(2-hydroxyethoxy)ethoxy)ethoxy)ethyl.

8. The method of claim 1, wherein $NR^2R^3$ is selected from the group consisting of piperidin-1-yl, morpholin-1-yl, tetrahydropyrrol-1-yl, (4-(2-hydroxyethyl))piperazin-1-yl, (4-methyl)piperazin-1-yl, (4-ethyl)piperazin-1-yl, (4-propyl)piperazin-1-yl, 4-(3-hydroxypropyl)piperazin-1-yl, 3-(morpholin-1-yl)propyl, adenine-1-yl, (4-(3-(dimethylamino)propyl)piperazin)-1-yl, (4-(2-(dimethylamino)ethyl)piperazin)-1-yl, (4-(3-(diethylamino)propyl)piperazin)-1-yl, (4-(2-(diethylamino)ethyl)piperazin)-1-yl, (4-(2-(piperidin-1-yl)ethyl)piperazin)-1-yl, (4-(3-(piperidin-1-yl)propyl)piperazin)-1-yl, (4-(2-(morpholin-1-yl)ethyl)piperazin)-1-yl, (4-(3-(morpholin-1-yl)propyl)piperazin)-1-yl, (4-(2-(tetrahydropyrrol-1-yl)ethyl)piperazin)-1-yl, and (4-(3-(tetrahydropyrrol-1-yl)propyl)piperazin)-1-yl.

9. The method of claim 1, wherein the compound is selected from the group consisting of:

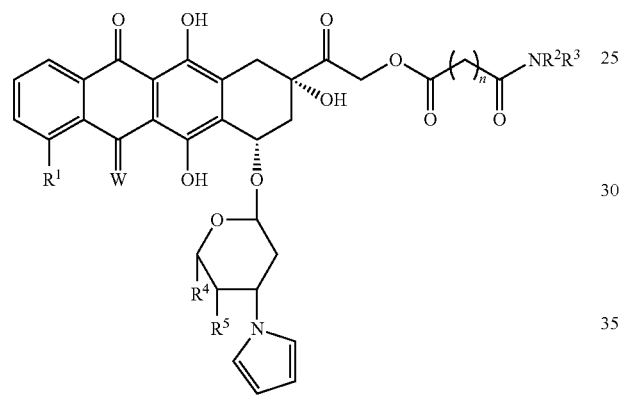

wherein W is O, $R^1$ is $OCH_3$, $R^4$ is $CH_3$, $R^5$ is OH, n and $NR^2R^3$ are shown in the following table:

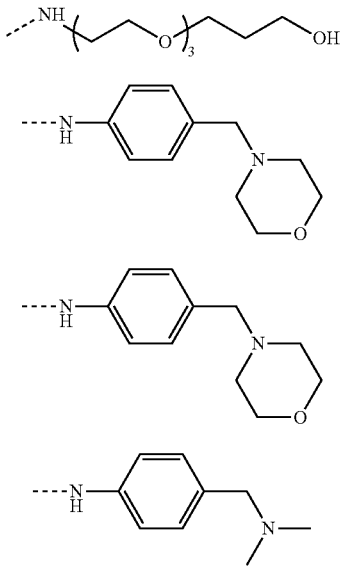

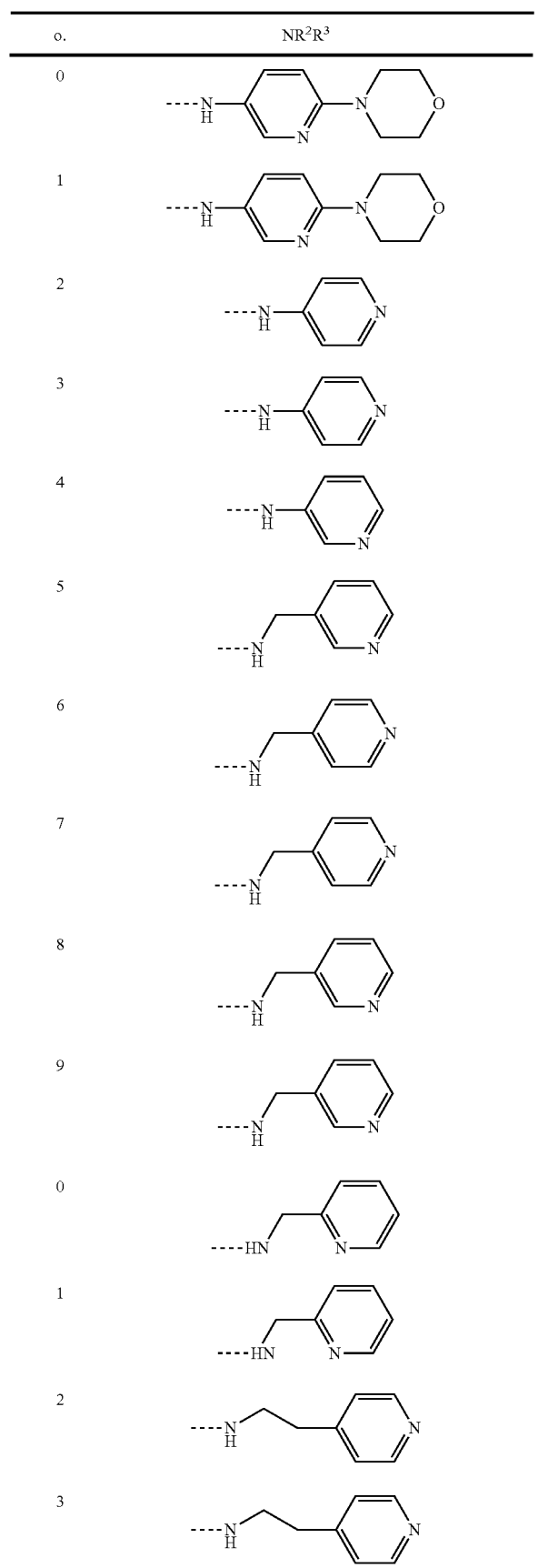
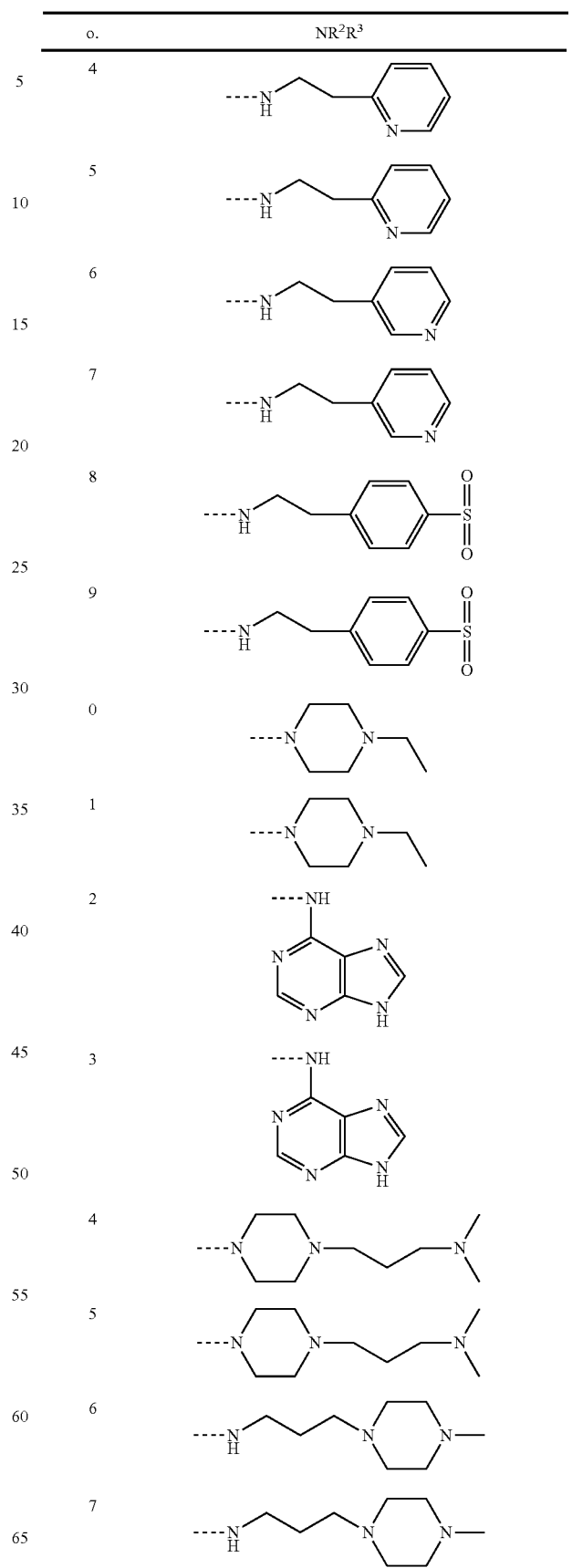

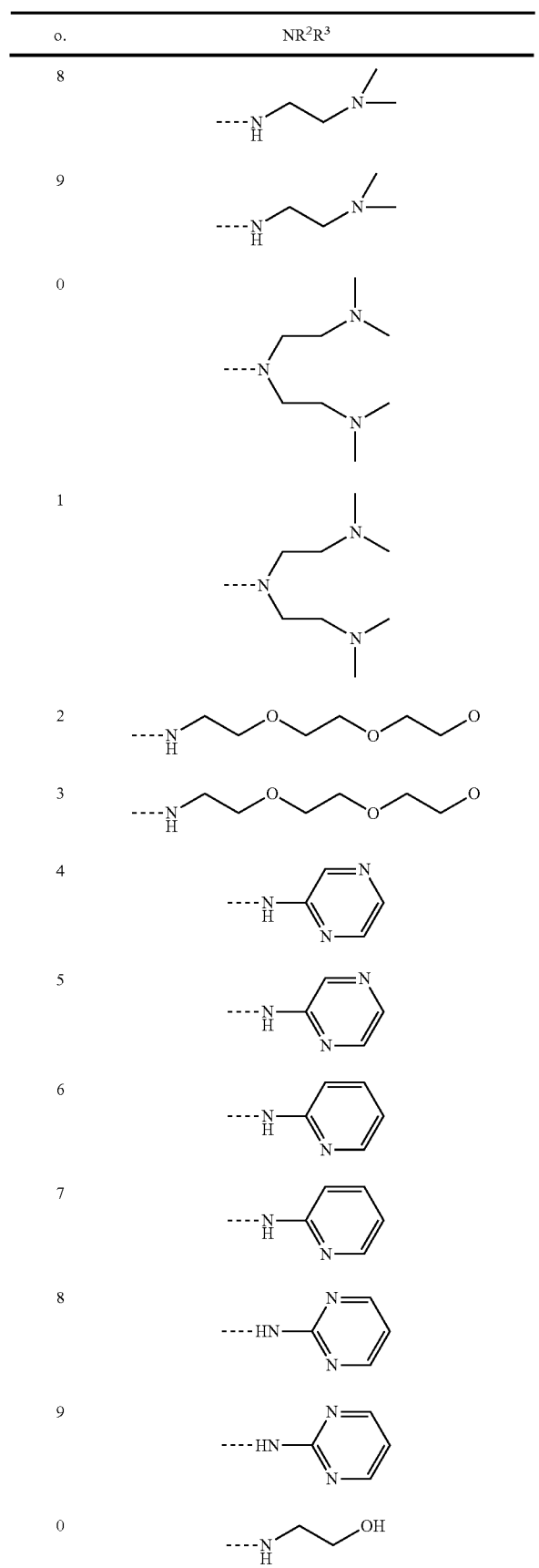
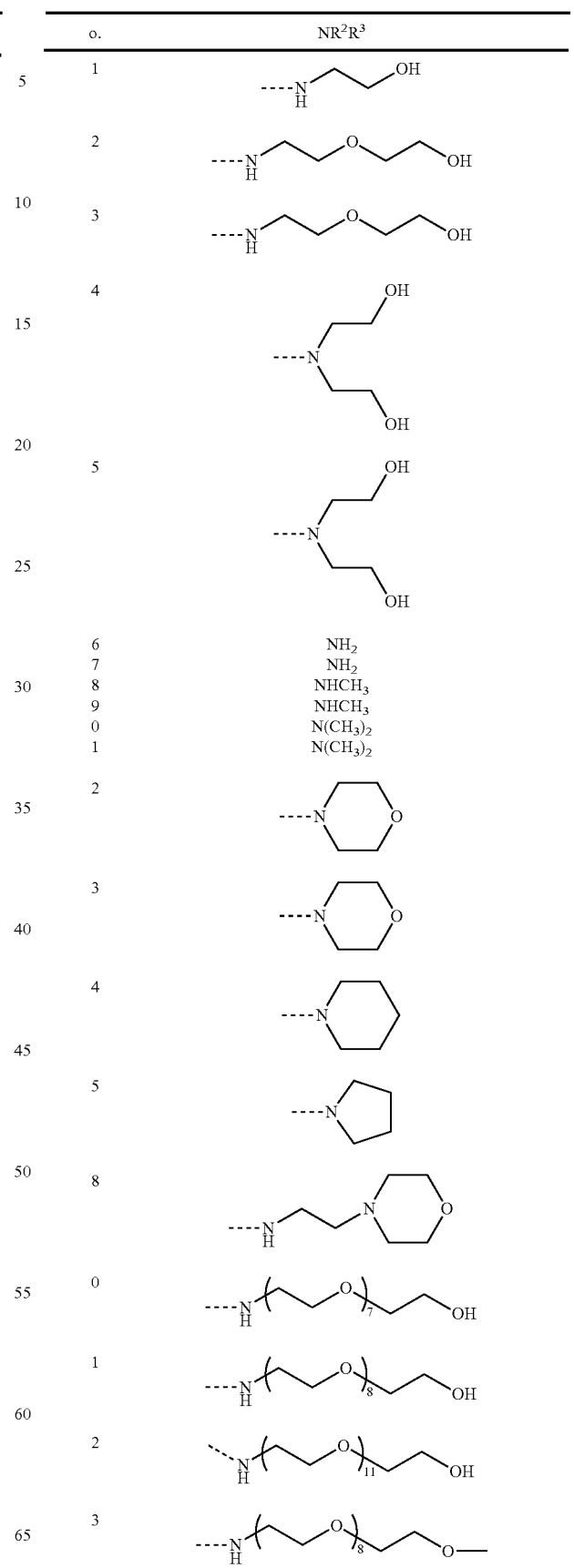

-continued

| o. | NR²R³ |
|---|---|
| 4 | 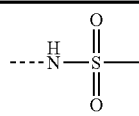 |
| 5 | 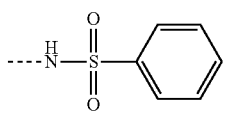 |

77) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((4-(2-hydroxy)ethyl)piperazin-1-yl)-4-oxo-butyrato)-1-methoxy-5,12-naphthalenedione acetate;

78) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((3-(morpholin-1-yl)propyl)amino)-4-oxo-butyrato)-1-methoxy-5,12-naphthalenedione acetate;

79) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((4-methyl)piperazin-1-yl)amino)-4-oxo-butyrato)-1-methoxy-5,12-naphthalenedione acetate;

80) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(4-ethylpiperazin-1-yl)-4-oxo-butyrato)-1-methoxy-5,12-naphthalenedione acetate;

81) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((3-(4-methylpiperazin-1-yl)propyl)amino)-4-oxo-butyrato)-1-methoxy-5,12-naphthalenedione acetate;

82) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((pyridin-4-yl)methyl)amino)-4-oxo-butyrato)-1-methoxy-5,12-naphthalenedione acetate;

83) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((pyridin-3-yl)methyl)amino)-4-oxo-butyrato)-1-methoxy-5,12-naphthalenedione acetate;

84) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-2-yl)ethyl)amino)-4-oxo-butyrato)-1-methoxy-5,12-naphthalenedione acetate;

85) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-3-yl)ethyl)amino)-4-oxo-butyrato)-1-methoxy-5,12-naphthalenedione acetate;

86) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(2-(pyridin-4-yl)ethyl)amino)-4-oxo-butyrato)-1-methoxy-5,12-naphthalenedione acetate;

87) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-(4-(3-(dimethylamino)propyl)piperazin-1-yl)-4-oxo-butyrato)-1-methoxy-5,12-naphthalenedione acetate;

89) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione acetate;

96) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione phosphate; and 99) 10-((3'-(pyrrol-1-yl)-2',3',6'-trideoxy-alpha-L-lyxo-hexylpyranyl)oxy)-7,8,9,10-tetrahydro-6,8,11-trihydroxy-13-oxo-14-(4-((2-(morpholin-1-yl)ethyl)amino)-4-oxo-butyrato)-1-methoxy-5,12-naphthalenedione hydrochloride.

10. The method of claim 1, wherein the formulation is a formulation for injection.

* * * * *

UNITED STATES PATENT AND TRADEMARK OFFICE
CERTIFICATE OF CORRECTION

PATENT NO. : 10,294,260 B2
APPLICATION NO. : 15/587884
DATED : May 21, 2019
INVENTOR(S) : Hesheng Zhang, Aihong Huo and Zhenzhong Li Page 1 of 11

It is certified that error appears in the above-identified patent and that said Letters Patent is hereby corrected as shown below:

In the Claims

Column 93, Line 15, Claim 1 delete "comprises" and insert --is selected from the group consisting of--

Column 93, Line 19, Claim 1 after "consisting of" delete "23" and insert --1--

Column 93, Line 28, Claim 1 after "consisting of" delete "23" and insert --1--

Column 95, Line 46, Claim 9 replace the entire table which ends at Column 101, Line 14 with:

| No. | n | $NR^2R^3$ |
|---|---|---|
| 1 | 3 | 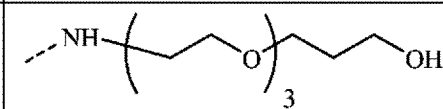 |
| 2 | 2 | 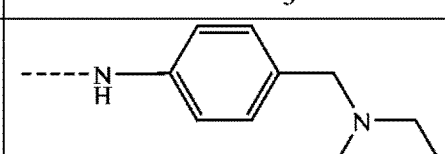 |
| 3 | 3 | 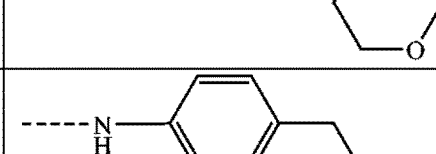 |

Signed and Sealed this
Fourteenth Day of January, 2020

Andrei Iancu
*Director of the United States Patent and Trademark Office*

| | | |
|---|---|---|
| <u>4</u> | <u>2</u> | 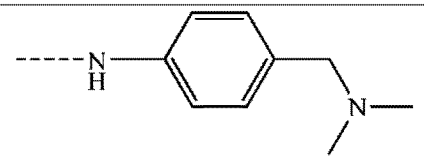 |
| <u>5</u> | <u>3</u> | 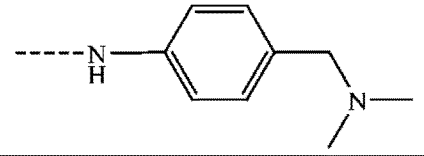 |
| <u>6</u> | <u>2</u> | 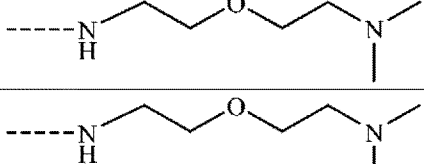 |
| <u>7</u> | <u>3</u> | 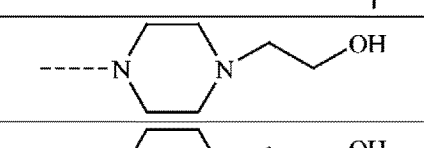 |
| <u>8</u> | <u>2</u> | 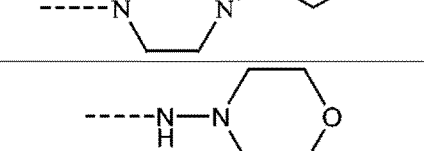 |
| <u>9</u> | <u>3</u> | 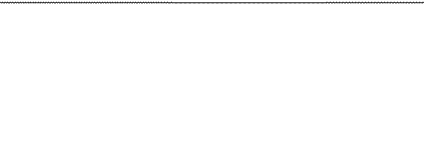 |
| <u>10</u> | <u>2</u> |  |

| 11 | 3 | 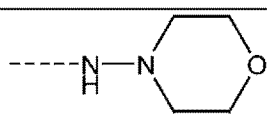 |
| 12 | 2 | 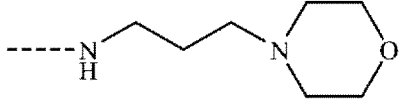 |
| 13 | 3 | 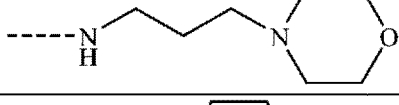 |
| 14 | 2 | 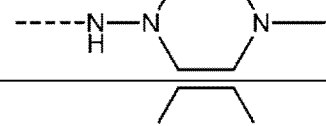 |
| 15 | 3 | 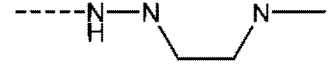 |
| 16 | 2 | 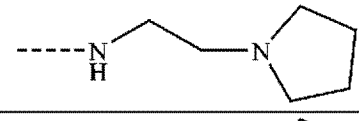 |
| 17 | 3 | 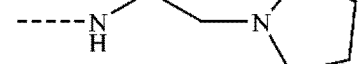 |
| 18 | 2 | 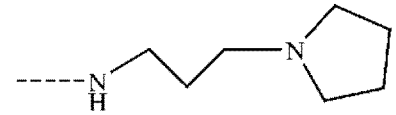 |

| 19 | 3 | 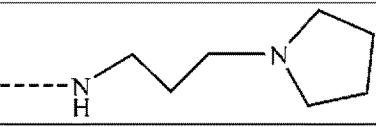 |
| --- | --- | --- |
| 20 | 2 | 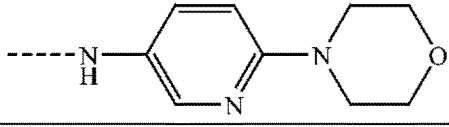 |
| 21 | 3 | 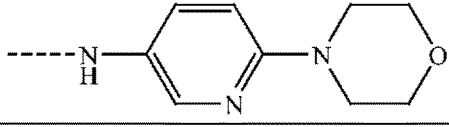 |
| 22 | 2 | 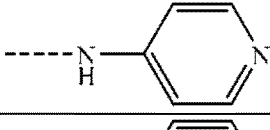 |
| 23 | 3 | 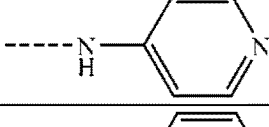 |
| 24 | 2 | 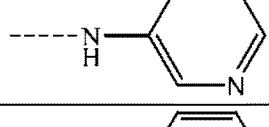 |
| 25 | 3 | 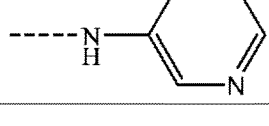 |

| 26 | 2 | -----NH-CH₂-(pyridin-4-yl) |
| 27 | 3 | -----NH-CH₂-(pyridin-4-yl) |
| 28 | 2 | -----NH-CH₂-(pyridin-3-yl) |
| 29 | 3 | -----NH-CH₂-(pyridin-3-yl) |
| 30 | 2 | -----HN-CH₂-(pyridin-2-yl) |
| 31 | 3 | -----HN-CH₂-(pyridin-2-yl) |
| 32 | 2 | -----NH-CH₂CH₂-(pyridin-4-yl) |

| 33 | 3 | 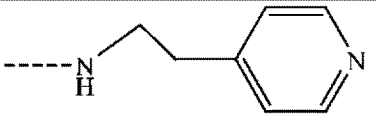 |
| 34 | 2 | 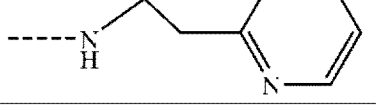 |
| 35 | 3 | 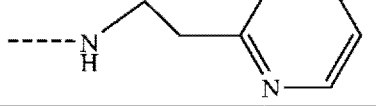 |
| 36 | 2 | 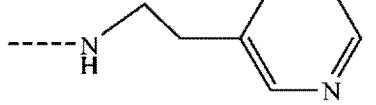 |
| 37 | 3 | 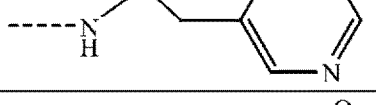 |
| 38 | 2 | 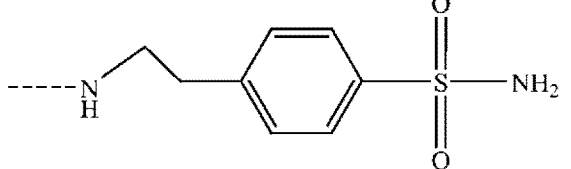 |

| | | |
|---|---|---|
| 39 | 3 | 4-(2-aminoethyl)benzenesulfonamide group (–NH–CH₂CH₂–C₆H₄–SO₂NH₂) |
| 40 | 2 | 4-ethylpiperazin-1-yl |
| 41 | 3 | 4-ethylpiperazin-1-yl |
| 42 | 2 | 9H-purin-6-ylamino (–NH–purine) |
| 43 | 3 | 9H-purin-6-ylamino (–NH–purine) |
| 44 | 2 | 4-(2-(dimethylamino)ethyl)piperazin-1-yl |
| 45 | 3 | 4-(2-(dimethylamino)ethyl)piperazin-1-yl |
| 46 | 2 | –NH–(CH₂)₃–(4-methylpiperazin-1-yl) |
| 47 | 3 | –NH–(CH₂)₃–(4-methylpiperazin-1-yl) |
| 48 | 2 | –NH–CH₂CH₂–N(CH₃)₂ |
| 49 | 3 | –NH–CH₂CH₂–N(CH₃)₂ |

| | | |
|---|---|---|
| 50 | 2 | 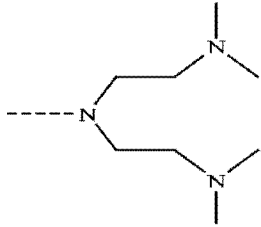 |
| 51 | 3 | 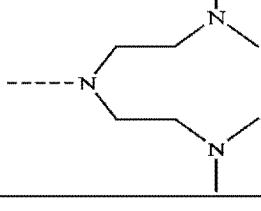 |
| 52 | 2 | 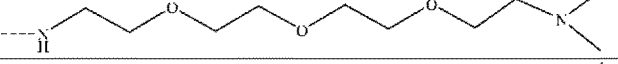 |
| 53 | 3 | 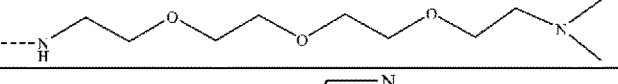 |
| 54 | 2 | 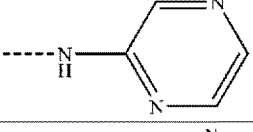 |
| 55 | 3 | 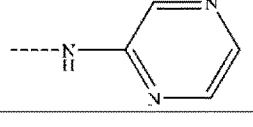 |

| 56 | 2 | |
| 57 | 3 | |
| 58 | 2 | |
| 59 | 3 | |
| 60 | 2 | -----NH-CH$_2$CH$_2$-OH |
| 61 | 3 | -----NH-CH$_2$CH$_2$-OH |
| 62 | 2 | -----NH-CH$_2$CH$_2$-O-CH$_2$CH$_2$-OH |
| 63 | 3 | -----NH-CH$_2$CH$_2$-O-CH$_2$CH$_2$-OH |

| 64 | 2 | ----N(CH₂CH₂OH)₂ |
|---|---|---|
| 65 | 3 | ----N(CH₂CH₂OH)₂ |
| 66 | 2 | NH₂ |
| 67 | 3 | NH₂ |
| 68 | 2 | NHCH₃ |
| 69 | 3 | NHCH3 |
| 70 | 2 | N(CH3)2 |
| 71 | 3 | N(CH3)2 |
| 72 | 2 | (azetidinyl) |
| 73 | 3 | (azetidinyl) |

| | | |
|---|---|---|
| 74 | 2 | 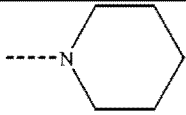 |
| 75 | 2 | 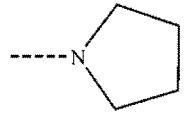 |
| 88 | 2 | 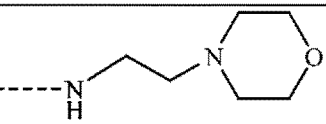 |
| 90 | 2 | 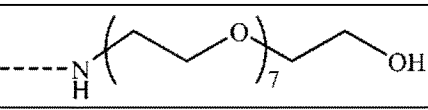 |
| 91 | 2 | 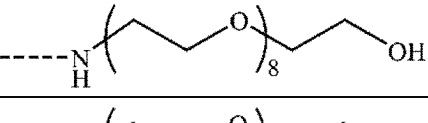 |
| 92 | 2 | 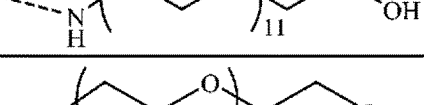 |
| 93 | 2 | 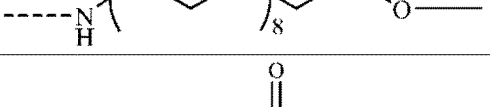 |
| 94 | 2 | 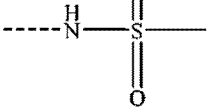 |
| 95 | 2 | 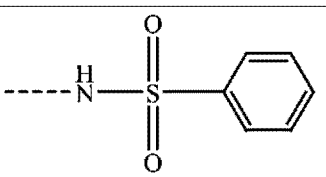 |